United States Patent
Murase et al.

(10) Patent No.: US 6,805,978 B2
(45) Date of Patent: Oct. 19, 2004

(54) PYRROMETHENE METAL COMPLEX AND LIGHT EMITTING DEVICE COMPOSITION AND LIGHT EMITTING DEVICES USING THE SAME

(75) Inventors: Seiichiro Murase, Shiga (JP); Tsuyoshi Tominaga, Shiga (JP); Akira Kohama, Shiga (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 10/126,652

(22) Filed: Apr. 22, 2002

(65) Prior Publication Data

US 2003/0082406 A1 May 1, 2003

(30) Foreign Application Priority Data

Apr. 25, 2001 (JP) .......................................... 2001-127311
May 28, 2001 (JP) .......................................... 2001-158325

(51) Int. Cl.$^7$ .................... H05B 33/114; C07D 231/00; C07D 207/00
(52) U.S. Cl. ...................... 428/690; 428/704; 428/917; 313/504; 313/506; 252/301.16; 252/301.31; 252/301.32; 252/301.35; 548/110; 548/405
(58) Field of Search ................................. 428/690, 704, 428/917; 313/504, 506; 252/301.16, 310.31, 301.32, 301.35; 548/110, 405, 301.7, 302.7

(56) References Cited

U.S. PATENT DOCUMENTS 5,248,782 A 9/1993 Haugland et al.

FOREIGN PATENT DOCUMENTS

| EP | 0 619 520 | 10/1994 |
|----|-----------|---------|
| EP | 1 000 998 A1 | 5/2000 |
| JP | 11-043491 | 2/1999 |
| JP | 11-97180 | 4/1999 |
| JP | 2000-208262 | 7/2000 |
| JP | 2000-250206 | 9/2000 |
| JP | 2001-240761 | 9/2001 |
| JP | 2001-242622 | 9/2001 |
| JP | 2001-242623 | 9/2001 |
| JP | 2001-297881 | 10/2001 |
| WO | WO 01/16141 | 3/2001 |

Primary Examiner—Deborah Jones
Assistant Examiner—Ling Xu
(74) Attorney, Agent, or Firm—Morrison & Foerster LLP

(57) ABSTRACT

A pyrromethene metal complex is used as a fluorescent dye to form a light emitting device. The light emitting device has a substance which brings about light emission between an anode and a cathode. By applying electrical energy, the device generates emission having an emission peak wavelength of 580 to 720 nm. The device contains at least one of: a diketopyrrolo[3,4-c]pyrrole derivative and an organic fluorescent material having a fluorescent peak wavelength of 580 to 720 nm; and a light emitting device composition containing a pyrromethene metal complex.

9 Claims, No Drawings

PYRROMETHENE METAL COMPLEX AND LIGHT EMITTING DEVICE COMPOSITION AND LIGHT EMITTING DEVICES USING THE SAME

BACKGROUND OF THE INVENTION

1. Field of the Invention

The present invention relates to pyrromethene metal complexes for use as fluorescent dye and to light emitting devices (LEDs) using the same.

2. Description of the Related Art

Organic thin-film LEDs, from which light is emitted when electrons injected from a cathode are recombined with holes injected from an anode in an organic fluorescent material between the cathode and the anode, have recently been studied with great interest. These devices are of interest because they can be formed in a thin structure, can emit light with high luminance under a low driving voltage, and can emit multicolored light depending on the fluorescent materials used.

Many research organizations have studied these elements since C. W. Tang et al of Kodak disclosed that an organic thin-film LED emits light with high luminance (Appl. Phys. Lett. 51 (12) 21, p. 913, 1987). A typical organic thin-film LED developed by Kodak comprises a hole transporting diamine compound, 8-hydroxyquinoline aluminum serving as a emissive layer, and a Mg—Ag cathode, in that order, on an ITO glass substrate. This LED was able to emit green light with a luminance of 1000 cd/m$^2$ under a driving voltage of about 10 V. Some existing organic thin-film LEDs are have undergone certain modifications. For example, an electron transporting layer may be additionally disposed in a device.

Research in green emissive materials is the most advanced for multicolored emission. Red and blue emissive materials are still required to be more durable and to have high luminance and chromatic purity, and have been studied more intensely.

Exemplary red emissive materials include perylenes such as bis(diisopropylphenyl)perylene, perynone, porphyrin, and Eu complexes (Chem. Lett., 1267(1991)).

Also, a method has been studied in which a host material is doped with a red fluorescent material to generate red emission. Exemplary host materials include quinolinol metal complexes such as tris(8-quinolinolato)aluminum, bis(10-benzoquinolinate)beryllium, diarylbutadienes, stilbenes, and benzothiazoles. These host materials are doped with 4-(dicyanomethylene)-2-methyl-6-(p-dimethylaminostyryl)-4H-pyran, metal phthalocyanine complexes such as MgPc and AlPcCl, squaliriums, and violanthrones to generate red luminescence.

Unfortunately, some of the known emissive materials including host materials and dopants have low luminance efficiency and thus have a high power consumption, and others are not durable and thus result in a short lifetime of the LED. Also, concentration quenching and exciplex and excimer formations often lower the fluorescence intensity when the materials are in a thin-film state although the materials have high fluorescence when they are in a solution. Thus, many of the materials cannot provide high luminance suitable for LEDs. It is a big problem that particularly most of the red emissive materials including host materials and dopants cannot provide both high chromatic purity and high luminance, simultaneously.

In Japanese Unexamined Patent Application Publication No. 2000-208270, a diketopyrrolo[3,4-c]pyrrole derivative and an organic fluorescent material having a peak fluorescent wavelength of 580 to 720 nm are used to generate a red emission, but cannot lead to high luminance.

SUMMARY OF THE INVENTION

Accordingly, an object of the present invention is to solve the above-described problem and to provide a new pyrromethene metal complex capable of resulting in an LED having high luminance efficiency and high chromatic purity and an LED using the same.

The present invention is directed to a pyrromethene metal complex.

The present invention is also directed to an LED material comprising the pyrromethene metal complex.

The present invention is also directed to an LED generating a emission having an emission peak wavelength in the range of 580 to 720 nm by electrical energy. The device comprises at least one of: an LED material comprising a diketopyrrolo[3,4-c]pyrrole derivative and an organic fluorescent material having a fluorescent peak wavelength of 580 to 720 nm; and an LED material comprising a pyrromethene metal complex.

According to the present invention, the pyrromethene metal complex has highly fluorescent properties and therefore can be used for LEDs. By using the pyrromethene metal complex, an LED having a high energy efficiency, a high luminance, and a high chromatic purity can be achieved.

DESCRIPTION OF THE PREFERRED EMBODIMENTS

Pyrromethene metal complexes represented by the chemical formula (1) will now be described in detail.

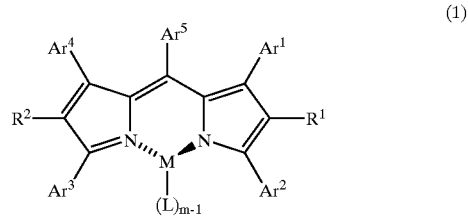

(1)

$R^1$, $R^2$, and L are each a substituent selected from the group consisting of hydrogen, alkyl, cycloalkyl, aralkyl, alkenyl, cycloalkenyl, alkynyl, hydroxyl, mercapto, alkoxy, alkylthio, aryl ether, aryl thioether, aryl, heterocyclic, halogen, haloalkane, haloalkene, haloalkyne, cyano, aldehyde, carbonyl, carboxyl, ester, carbamoyl, amino, nitro, silyl, siloxanyl, and a fused aromatic ring and an alicyclic ring formed with adjacent substituents. $R^1$, $R^2$, and L may be the same as or different from one another. M represents a metal having a valence of m and is selected from the group consisting of boron, beryllium, magnesium, chromium, iron, nickel, copper, zinc, and platinum. $Ar^1$ to $Ar^5$ represent aryl.

In these substituents, alkyl means saturated aliphatic hydrocarbon substituents such as methyl, ethyl, propyl, and butyl. Cycloalkyl means saturated alicyclic ring substituents such as cyclopropyl, cyclohexyl, norbornyl, and adamantyl. Aralkyl means substituents formed with aromatic hydrocarbons having an aliphatic hydrocarbon therebetween, such as benzyl and phenylethyl. Alkenyl means unsaturated aliphatic hydrocarbon substituents having a double bond, such as vinyl, allyl, and butadienyl. Cycloalkenyl means unsaturated alicyclic ring substituents having a double bond, such as cyclopentenyl, cyclopentadienyl, and cyclohexene. Alkynyl means unsaturated aliphatic hydrocarbon substituents having a triple bond, such as acetylenyl. Alkoxy means substituents formed with aliphatic hydrocarbons having an ether linkage therebetween, such as methoxy. Alkylthio means substituents in which sulfur is substituted for oxygen in the ether linkage of alkoxy. Aryl ethers mean substituents formed with aromatic hydrocarbons having an ether linkage therebetween, such as phenoxy. Aryl thioethers mean substituents in which sulfur is substituted for oxygen in the ether linkage of aryl ethers. Aryl means aromatic hydrocarbon substituents, such as phenyl, naphthyl, biphenyl, phenanthryl, terphenyl, and pyrenyl. Heterocyclic means cyclic substituents having an atom other than carbon, such as furyl, thienyl, oxazolyl, pyridyl, quinolyl, and carbazolyl. Halogens mean fluorine, chlorine, bromine, and iodine. Haloalkane, haloalkene, and haloalkyne mean substituents in which halogens are substituted for part or entirety of the above-described alkyl, alkenyl, or alkynyl. Aldehyde, carbonyl, ester, carbamoyl, and amino includes substituents having an aliphatic hydrocarbon, an alicyclic ring, an aromatic hydrocarbon, a heterocycle, and the like therein. Silyl means silicon compounds such as trimethylsilyl. Each above-described substituent may have a substituent therein or not. The fused aromatic ring and the alicyclic ring may have a substituent or not.

Boron complexes represented by the following chemical formula (2) have higher fluorescence quantum yield in the metal complexes represented by the chemical formula (1).

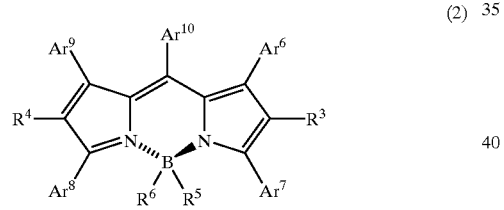

(2)

$R^3$ to $R^6$ may be the same as or different from one another, and are each a substituent selected from the group consisting of hydrogen, alkyl, cycloalkyl, aralkyl, alkenyl, cycloalkenyl, alkynyl, hydroxyl, mercapto, alkoxy, alkylthio, aryl ethers, aryl thioethers, aryl, heterocyclic, halogens, haloalkane, haloalkene, haloalkyne, cyano, aldehyde, carbonyl, carboxyl, esters, carbamoyl, amino, nitro, silyl, siloxanyl, and a fused aromatic ring and an alicyclic ring formed with adjacent substituents. $Ar^6$ to $Ar^{10}$ represent aryl groups. These substituents are the same as in the chemical formula (1).

By substituting alkyl having a carbon number of 4 or more for at least one of $Ar^1$ to $Ar^4$ of the formula (1) and at least one of $Ar^6$ to $Ar^9$, of the formula (2) the dispersibility of the material is improved and thus high luminance can be obtained. Preferably, both R5 and R6 of the formula (2) are fluorine in view of the availability and the synthesis of primary materials. Exemplary pyrromethene metal complexes are represented by the following formulas.

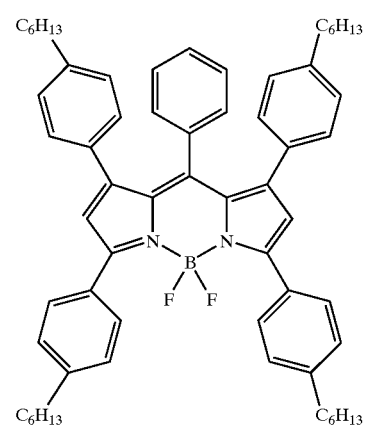

[1]

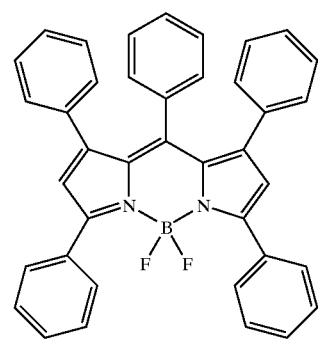

[2]

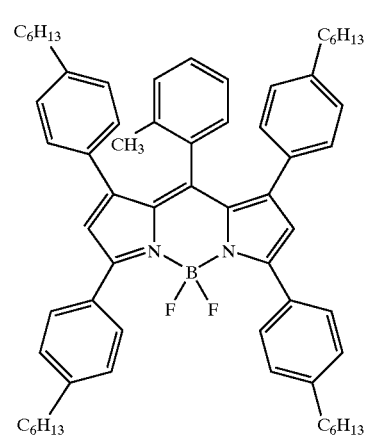

[3]

-continued
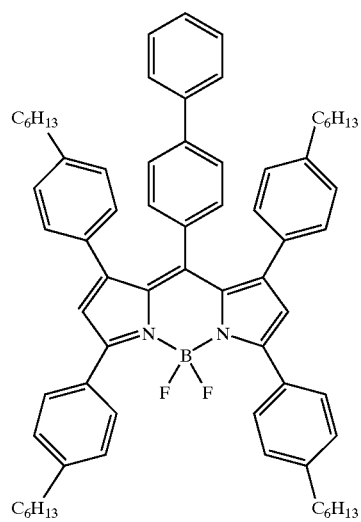
[4]
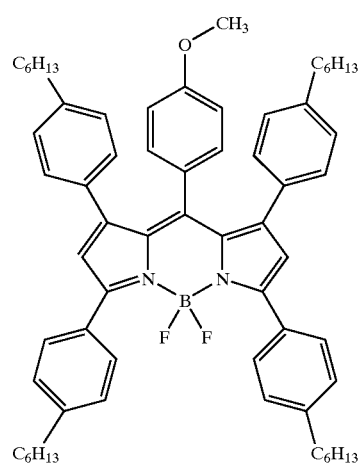
[5]
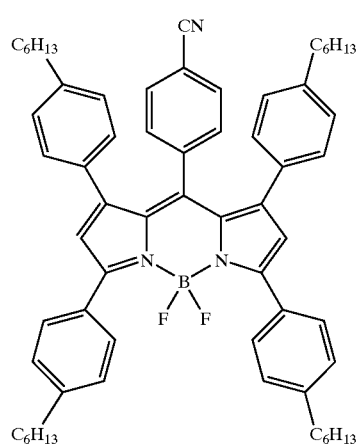
[6]
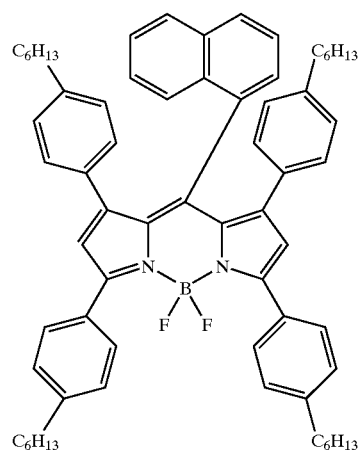
[7]
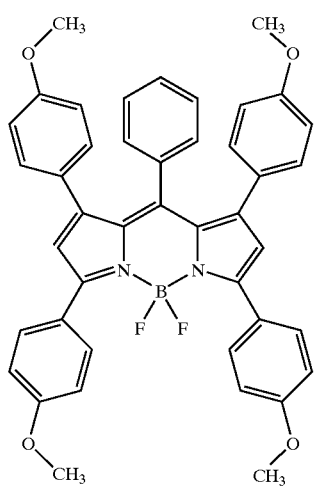
[8]
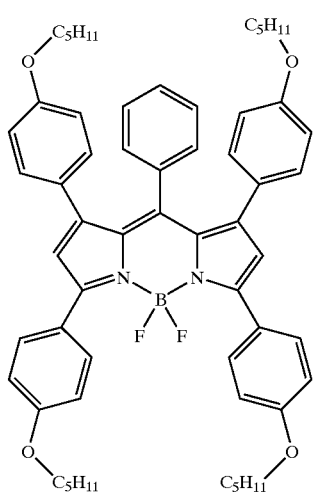
[9]

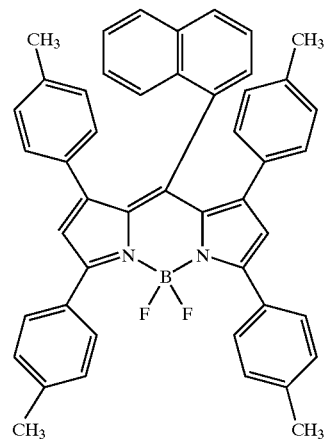
[10]
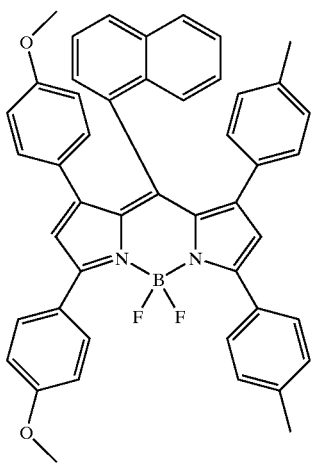
[13]
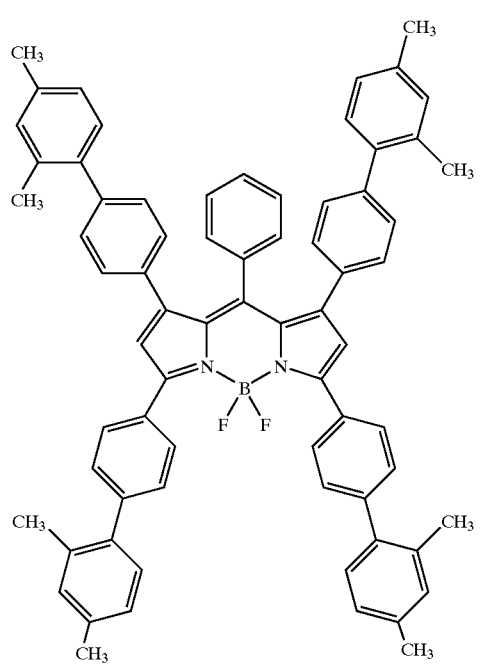
[11]
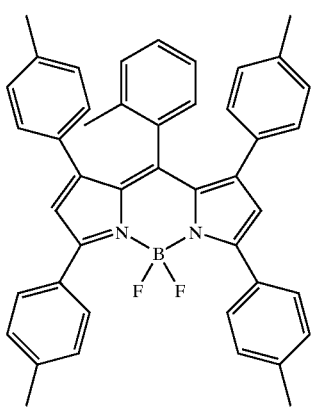
[14]
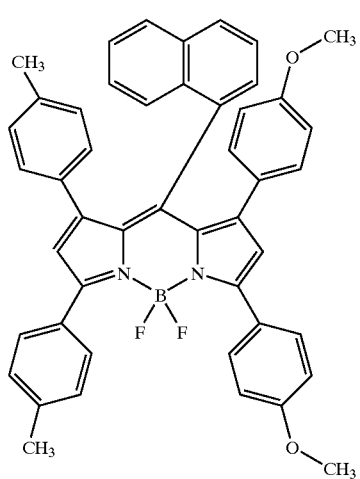
[12]
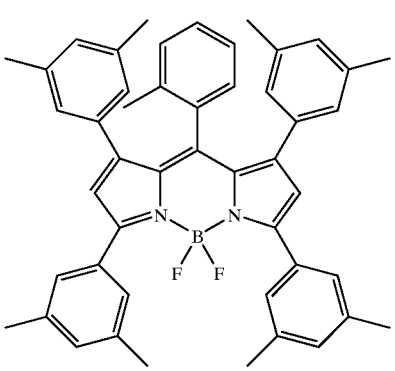
[15]

[16]
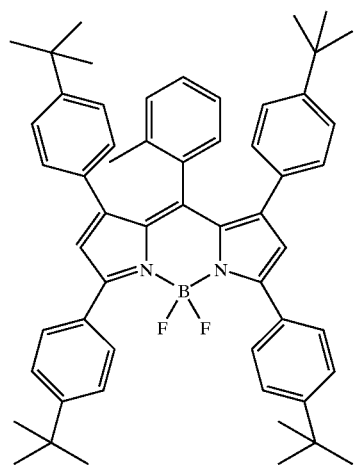
[17]
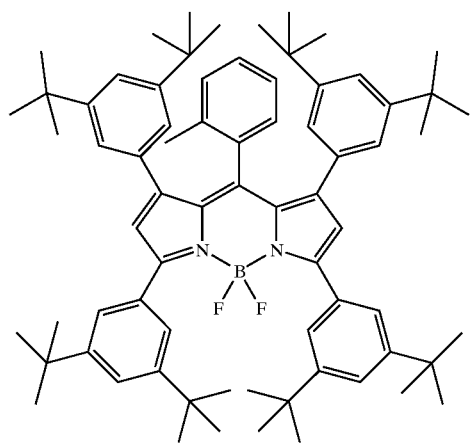
[18]
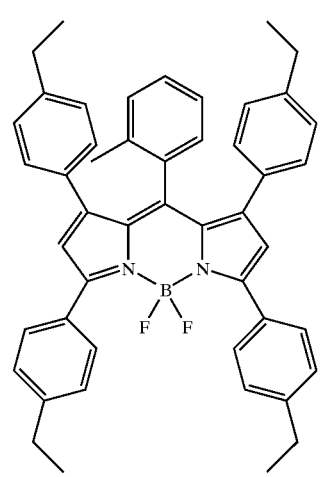
[19]
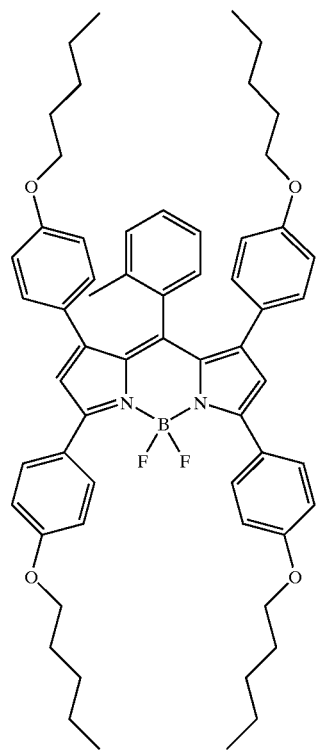
[20]
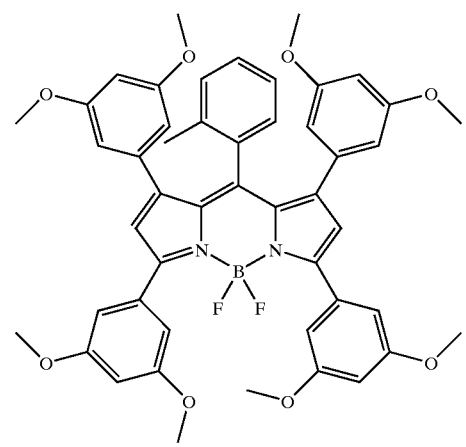
[21]
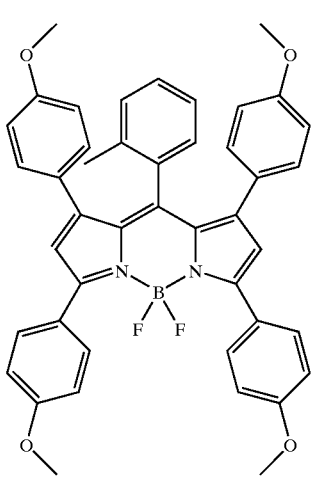

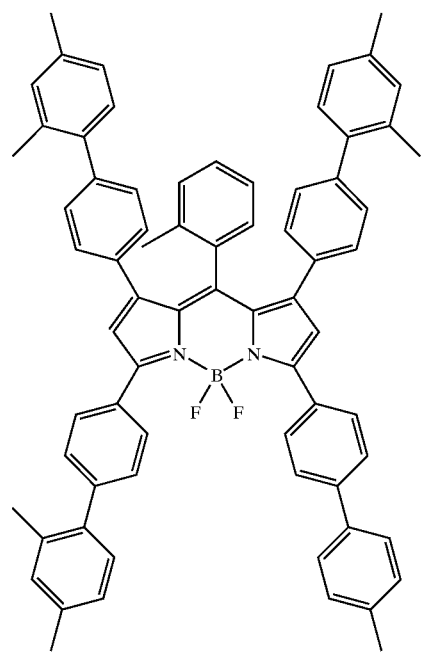
[22]
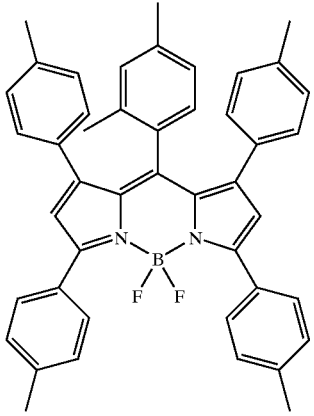
[25]
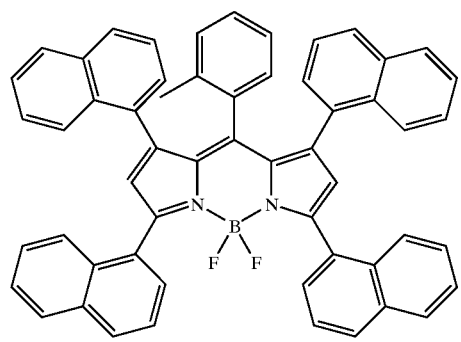
[23]
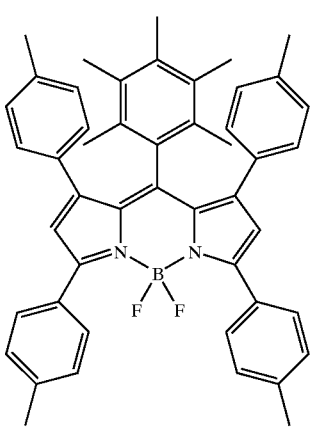
[26]
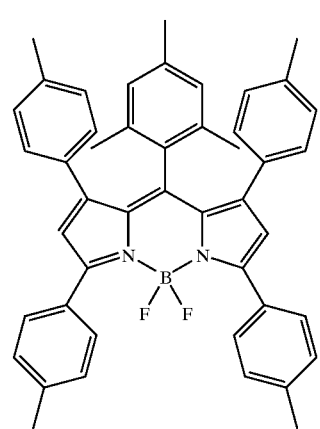
[24]
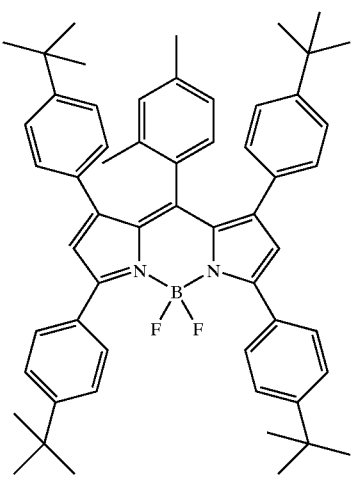
[27]

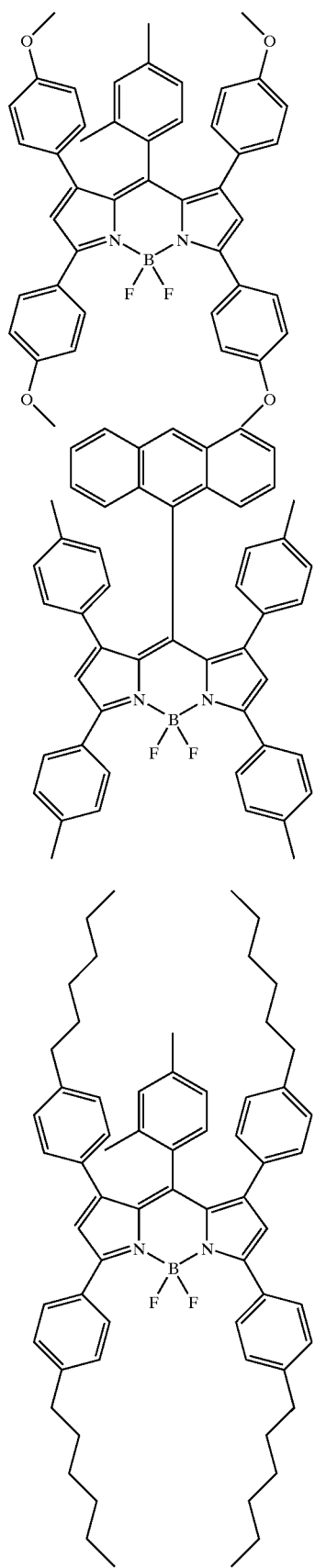
[28]
[29]
[30]
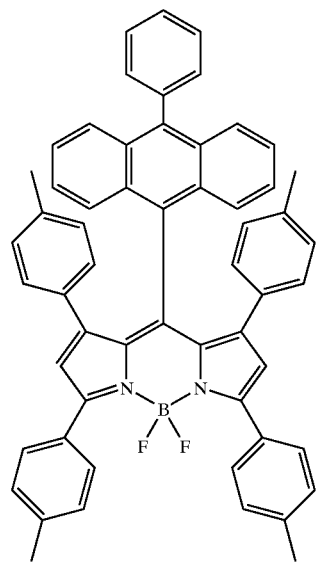
[31]
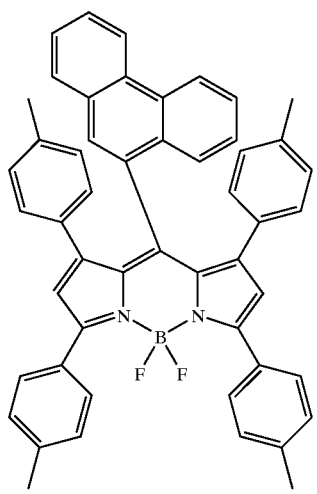
[32]
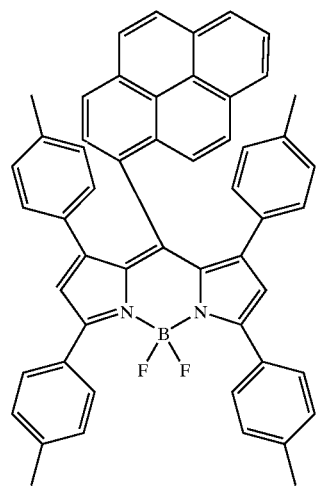
[33]

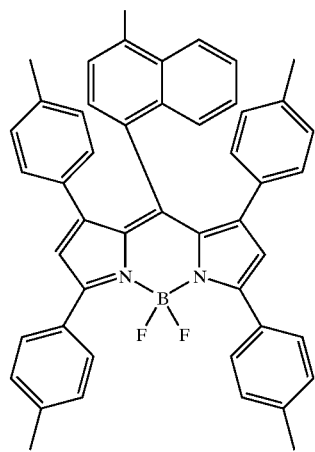
[34]
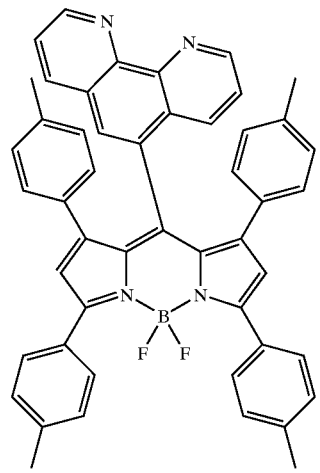
[37]
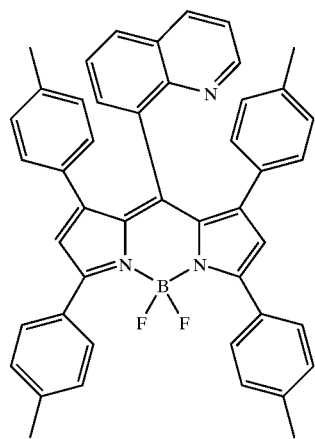
[35]
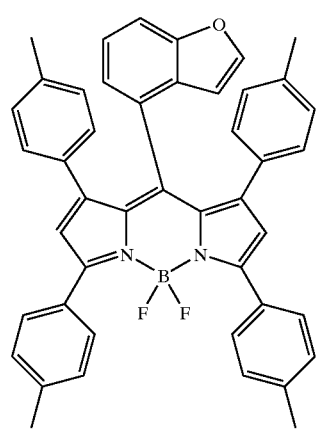
[38]
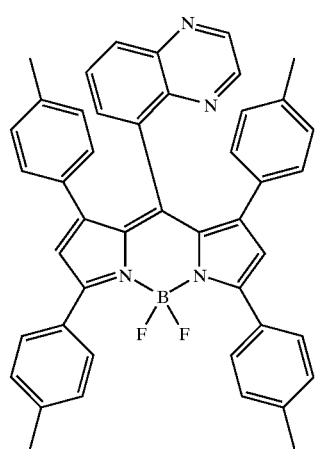
[36]
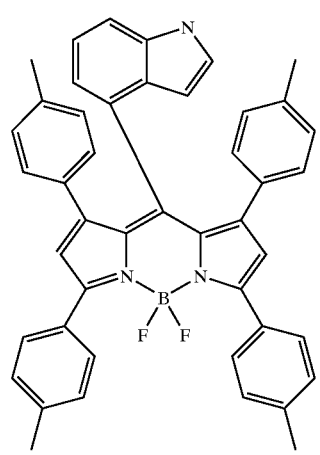
[39]

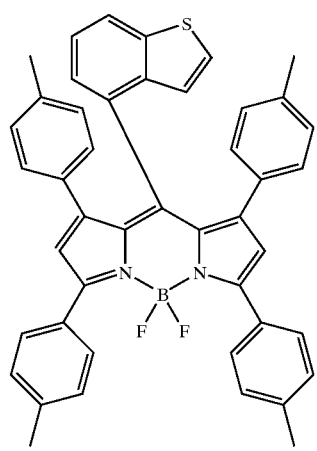
[40]
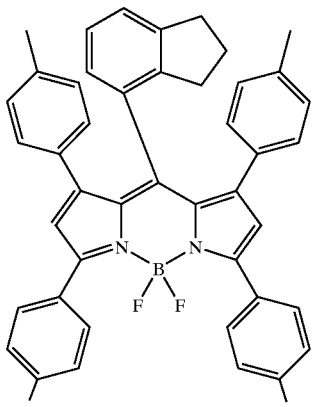
[43]
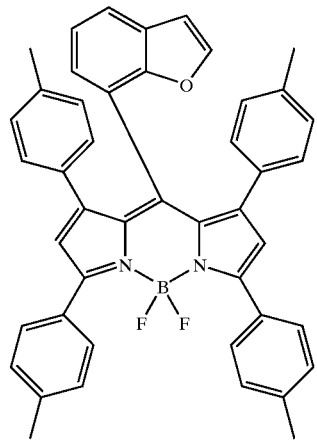
[41]
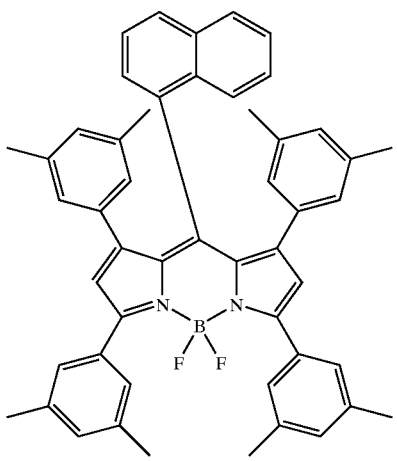
[44]
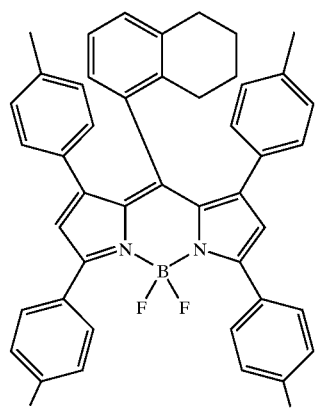
[42]
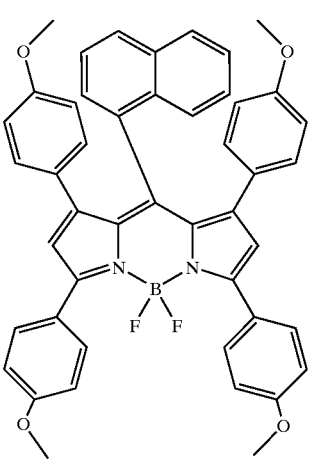
[45]

[46]
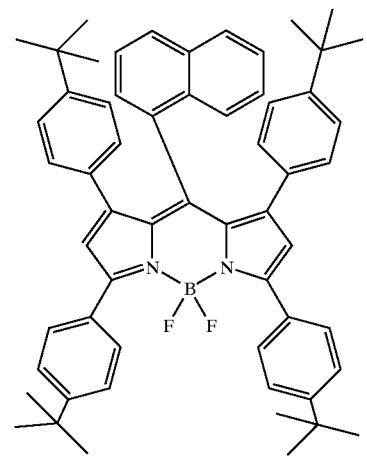
[47]
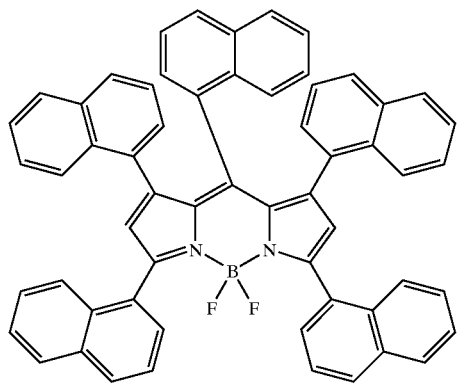
[47]
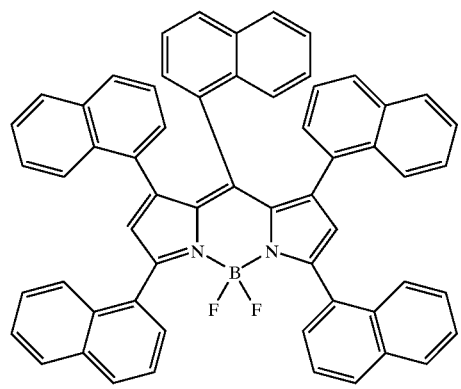
[48]
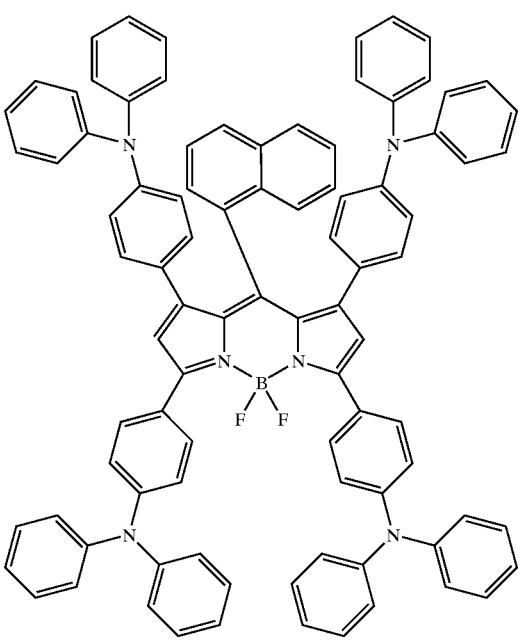
[48]
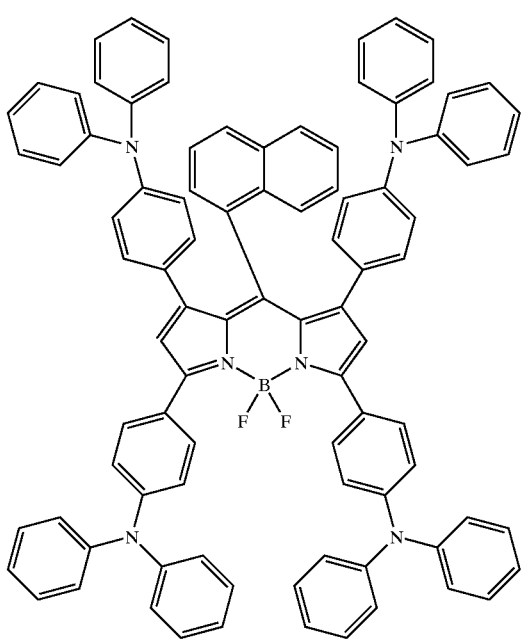
[49]
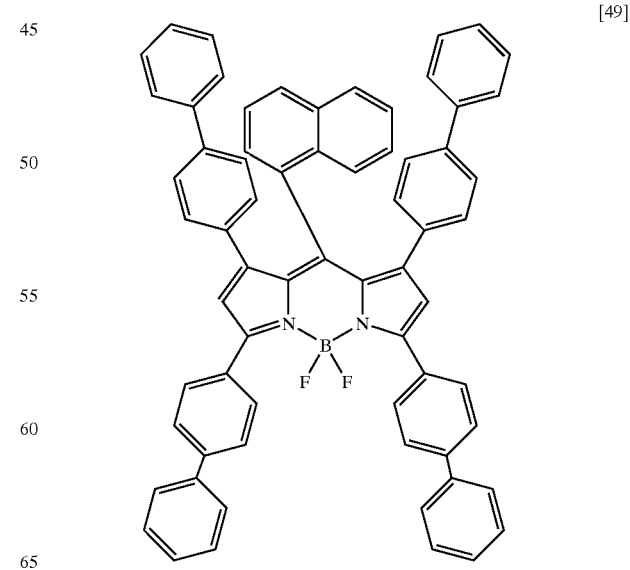

[50]
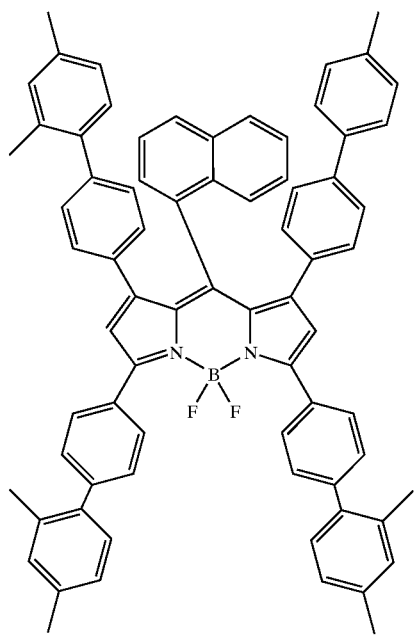
[51]
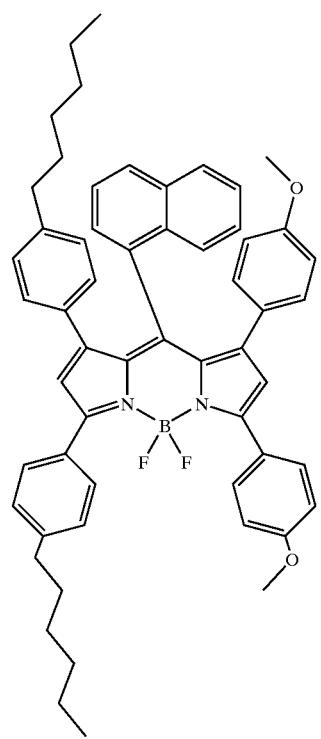
[52]
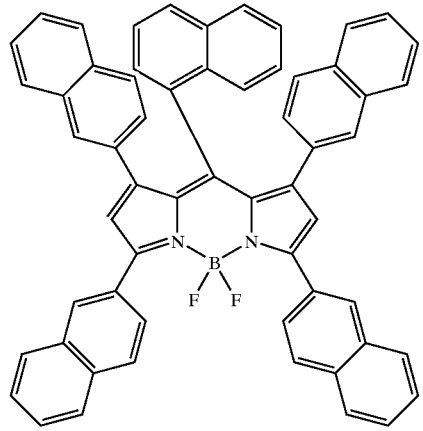
[53]
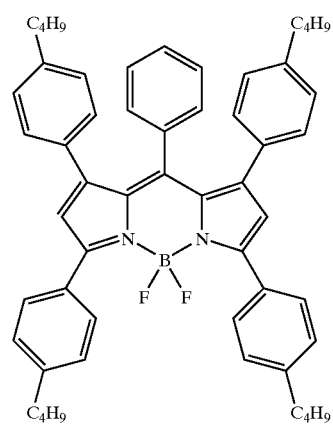
[54]
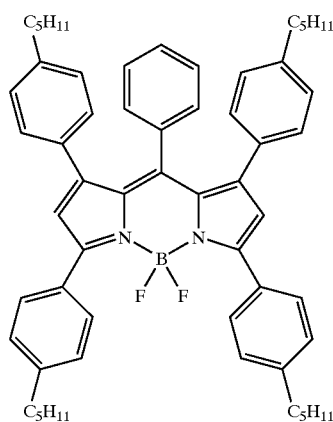

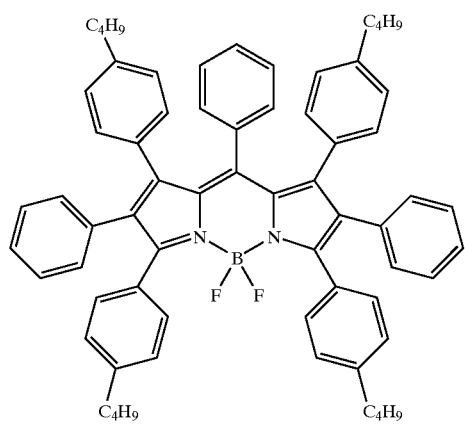
[55]
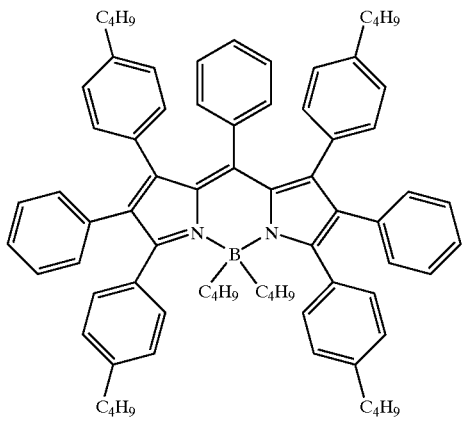
[58]
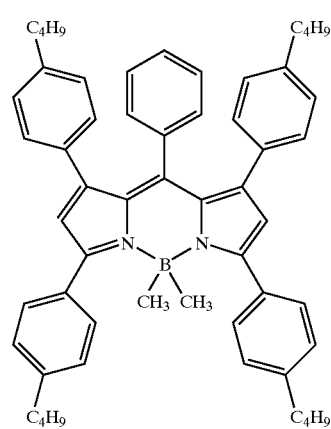
[56]
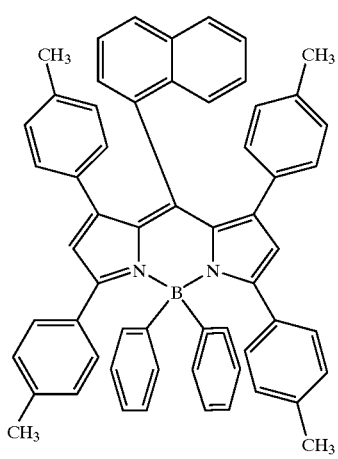
[59]
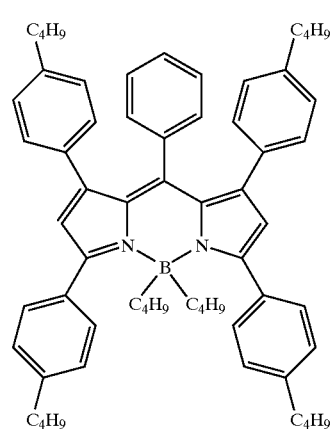
[57]
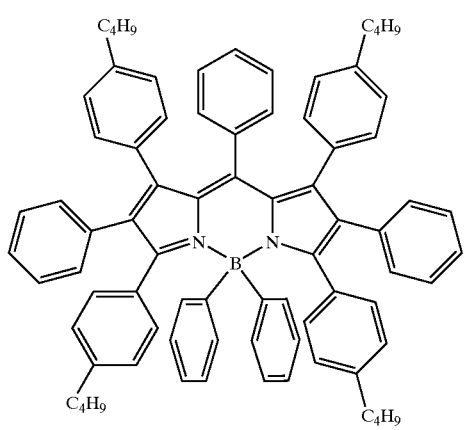
[60]

-continued

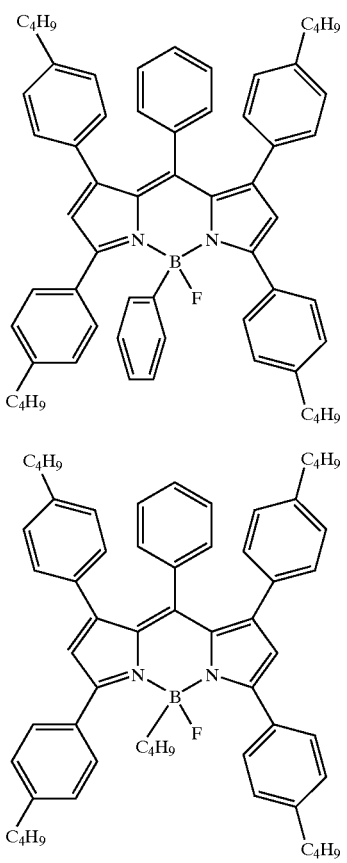

The pyrromethene metal complexes of the present invention may be prepared in accordance with the following procedure.

Compounds represented by the formulas (7) and (8) are heated with phosphorus oxychloride in 1,2-dichloroethane, and are followed by reacting a compound represented by the formula (9) in the presence of triethylamine. Thus, a metal complex represented by formula (1) is obtained. $Ar^1$ to $Ar^5$, $R^1$ and $R^2$, M, L, and m are the same as in the description above. J represents a halogen.

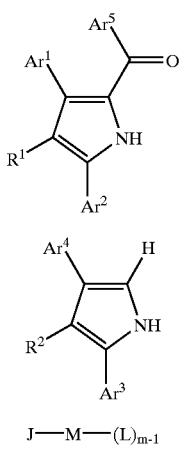

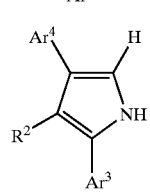

Thus the prepared pyrromethene metal complex of the present invention is suitable for an LED material. An LED of the present invention will now be described in detail.

An anode is formed of a transparent material to transmit light. Exemplary materials of the anode include conductive metal oxides such as tin oxide, indium oxide, and indium tin oxide (ITO); metals such as gold, silver, and chromium; conductive inorganic compounds such as copper iodide and copper sulfide; and conductive polymers such as polythiophene, polypyrrole, and polyaniline. In particular, ITO glass and Nesa glass are preferably used. The resistance of the transparent anode is not limited as long as current can be supplied to ensure that light is emitted from the device, but preferably, it is low with respect to power consumption of the device. For example, a substrate with ITO having a resistance of 300 Ω/□ or less is used for the anode. The thickness of ITO is set according to the resistance thereof and often set in the range of 100 to 300 nm. A glass substrate is formed of soda-lime glass, alkali-free glass, or the like. The thickness of the glass substrate is 0.5 or more to ensure the mechanical strength of the device. Preferably, alkali-free glass is used because few ions are eluted therefrom. Alternatively, soda-lime glass coated with $SiO_2$ may be used. However, the substrate is not limited to being formed of glass as long as the anode can be ensured the stable function thereof, and may be formed of a plastic. ITO may be deposited by an electron beam, sputtering, a chemical reaction method, or the like and is not limited to being formed by these methods.

A cathode is preferably formed of a material capable of efficiently injecting electrons into an organic layer. Exemplary cathode materials include platinum, gold, silver, copper, iron, tin, aluminum, indium, chromium, lithium, sodium, potassium, calcium, magnesium, cesium, and strontium. In order to increase the electron-injection efficiency to improve the performance of the device, metals having a low work function, such as lithium, sodium, potassium, calcium, cesium, and magnesium, and alloys containing these metals are advantageously used. However, generally speaking, these metals having a low work function are generally unstable in the air, so for example the method of using a highly stable electrode and doping the organic layer with a small amount of lithium, magnesium, or cesium (1 nm or less in thickness when measured by a thickness meter on vacuum deposition) can be given as a preferred example. Alternatively, inorganic salts such as lithium fluoride may be used. In order to protect the cathode, preferably, a metal such as platinum, gold, silver, copper, iron, tin, aluminum, or indium or an alloy of these metals, an inorganic substance such as silica, titania, or silicon nitride, and a polymer such as polyvinyl alcohol, polyvinyl chloride, or a hydrocarbon are further laminated. Preferably, the cathode is formed by a method in which the conductivity can be ensured, such as resistance heating, electron beam, sputtering, ion plating, or coating.

The substance which brings about light emission in the present invention may comprise: (1) a hole transporting layer and a emissive layer; (2) a hole transporting layer, a emissive layer, and an electron transporting layer; (3) a emissive layer and an electron transporting layer; (4) a hole transporting layer, a emissive layer, and a hole-blocking layer; (5) a hole transporting layer, a emissive layer, a hole-blocking layer, and an electron transporting layer; (6) a emissive layer, a hole-blocking layer, and an electron transporting layer; or (7) a monolayer containing some of the materials of the above-described layers. Hence, the LED may have a multilayer structure of (1) to (6) or a monolayer structure composed of an LED material alone or including an LED material and a material of the hole transporting layer, the hole-blocking layer, or the electron transporting layer. The substance which brings about light emission, in the present invention, means substances and layers contributing to the light emission of the device, and may emit light itself or may help to emit light.

The substances of the present invention comprise a diketopyrrolo[3,4-c]pyrrole derivative having a specific structure and an organic fluorescent material having a fluorescent peak wavelength of 580 to 720 nm. Alternatively, the substances comprise a pyrromethene metal complex. These substances may be contained in any layer of the above-described layers, and preferably, are contained in the emissive layer because both substances are fluorescent.

The hole transporting layer serves to transport holes injected from the anode. Exemplary hole transporting materials include: triphenylamines, such as N,N'-diphenyl-N,N'-bis(3-methylphenyl)-4,4'-dipheny-1,1'-diamine and N,N'-bis(1-naphthyl)-N,N'-diphenyl-4,4'-dipheny-1,1'-diamine; bis(N-arylcarbazole) and bis(N-alkylcarbazole) derivatives; and pyrazolines, stilbenes, distyryl derivatives, hydrazones, heterocyclic compounds, such as oxadiazoles, phthalocyanines, and porphyrins; and polymers, such as polycarbonates and styrenes having a monomer of the above-described compounds as a side chain group, polyvinyl carbazole, and polysilanes. However, the hole transporting materials are not limited to these as long as they can be formed into a thin film and does not inhibit the transporting of holes injected from the anode. The hole transporting layer may be formed of one of the above-described materials alone, or may be formed of a plurality of materials.

The emissive layer is provided with an LED material. The LED of the present invention emits light having a peak wavelength of 580 to 720 nm by electrical energy. A light having a peak wavelength less than 580 nm cannot lead to red emission with excellent chromatic purity even if the peak width thereof is small. On the other hand, a light having a peak wavelength greater than 720 nm leads to a degraded luminous efficacy and therefore, cannot provide red emission with a high luminance. The emissive material comprises at least one of the following (a) and (b).

(a) A diketopyrrolo[3,4-c]pyrrole derivative represented by formula (3) and an organic fluorescent material having a peak fluorescent wavelength of 580 to 720 nm.

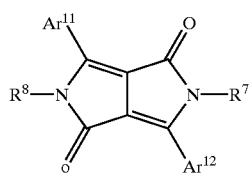

(3)

$R^7$ and $R^8$ are each a substituent selected from the group consisting of alkyl having carbon numbers of 1 to 25 and substituents represented by formula (4), and may be the same or different.

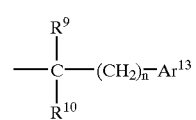

(4)

$R^9$ and $R^{10}$ are each a substituent selected from the group consisting of hydrogen, alkyl having carbon numbers of 1 to 4, phenyl having no substituent or having alkyl having a carbon number of 1 to 3 therein, and $R^9$ and $R^{10}$ may be the same or different. $Ar^{13}$ is a substituent selected from the group consisting of phenyl and naphthyl having alkyl or alkoxy or halogen or phenyl, and naphthyl. n represents a whole number of 0 to 4. $Ar^{11}$ and $Ar^{12}$ a substituent selected from the group consisting of phenyl, naphthyl, styryl, and carbazolyl.

(b) A pyrromethene metal complex represented by the above-described formula (1).

In the case of (a), a diketopyrrolo[3,4-c]pyrrole derivative represented by formula (3) and an organic fluorescent material having a peak fluorescent wavelength of 580 to 720 nm are used as both a dopant and a host. Preferably, the diketopyrrolo[3,4-c]pyrrole derivative is used as a host and the organic fluorescent material is used as a dopant.

The compounds represented by formulas (3) and (4) will now be described in detail. Substituents $R^7$ and $R^8$, which are alkyl having a carbon number of 1 to 25, may have a straight chain or a side chain. Specifically, $R^7$ and $R^8$ may be methyl, ethyl, n-propyl, isopropyl, n-butyl, sec-butyl, isobutyl, tert-butyl, n-pentyl, 2-pentyl, 3-pentyl, 2,2-dimethylpropyl, n-hexyl, n-heptyl, n-octyl, 1,1,3,3-tetramethylbutyl, 2-ethylhexyl, n-nonyl, decyl, undecyl, dodecyl, tetradecyl, pentadecyl, hexadecyl, heptadecyl, octadecyl, eicosyl, heneicosyl, docosyl, tetracosyl, and pentacosyl. Preferably, $R^7$ and $R^8$ are methyl, ethyl, n-propyl, isopropyl, n-butyl, sec-butyl, isobutyl, tert-butyl, n-pentyl, 2-pentyl, 3-pentyl, 2,2-dimethylpropyl, n-hexyl, n-heptyl, n-octyl, 1,1,3,3-tetramethylbutyl, and 2-ethylhexyl, which have carbon numbers of 1 to 8. More preferably, $R^7$ and $R^8$ are methyl, ethyl, n-propyl, isopropyl, n-butyl, sec-butyl, isobutyl, and tert-butyl, which have carbon numbers of 1 to 4.

The alkyl groups having carbon numbers of 1 to 4 represented by $R^9$ and $R^{10}$ include methyl, ethyl, n-propyl, isopropyl, n-butyl, sec-butyl, isobutyl, and tert-butyl. The phenyl groups represented by $R^9$ and $R^{10}$ may have alkyl with a carbon number of 1 to 3, and this alkyl includes methyl, ethyl, n-propyl, and isopropyl. The phenyl groups represented by $Ar^{13}$ have at least one of alkyl, alkoxy, halogen, and phenyl and may have these substituents at up to three bonding sites, whether the substituents are the same as or different from one another. In this instance, preferably, alkyl has a carbon number of 1 to 8. Specifically this alkyl includes methyl, ethyl, n-propyl, isopropyl, n-butyl, sec-butyl, isobutyl, tert-butyl, n-pentyl, 2-pentyl, 3-pentyl, 2,2-dimethylpropyl, n-hexyl, n-heptyl, n-octyl, 1,1,3,3-tetramethylbutyl, and 2-ethylhexyl. The alkoxy, preferably, has a carbon number of 1 to 8, and specifically may be methoxy, ethoxy, n-propoxy, isopropoxy, n-butoxy, sec-butoxy, isobutoxy, tert-butoxy, n-pentoxy, 2-pentoxy, 3-pentoxy, 2,2-dimethylpropoxy, n-hexoxy, n-heptoxy, n-octoxy, 1,1,3,3-tetramethylbutoxy, and 2-ethylhexoxy. Halogen mean fluorine, chlorine, bromine, and iodine. The phenyl which the phenyl groups represented by $Ar^{13}$ have therein further has alkyl or alkoxy having a carbon number of 1 to 8. These alkyl and alkoxy are the same as in the above. Naphthyl groups represented by $Ar^{13}$ include 1-napohthyl and 2-naphtyl, and may have any substituent and preferably the same substituents as in the above-described phenyl groups.

$Ar^{11}$ and $Ar^{12}$ are substituents selected from the group consisting of phenyl, naphthyl, styryl, and carbazolyl. The naphthyl, styryl and carbazolyl groups may be combined with diketopyrrolo[3,4-c]pyrrole skeleton at any bonding site thereof. These phenyl, naphthyl, styryl, and carbazolyl groups may have a substituent selected from the group consisting of hydrogen, cyano, halogen, alkyl, cycloalkyl, aralkyl, alkoxy, alkylthio, aryloxy, aryl thioether, aryl, heterocyclic, amino, silyl, and a fused aromatic ring and an alicyclic ring formed with adjacent substituents. Halogen is the same as in the above description. The alkyl groups may have a straight chain or a side chain and preferably have a carbon number of 1 to 25, more preferably of 1 to 8. Exemplary alkyl groups are the same as in the above description. The cycloalkyl groups, preferably, have a carbon number in the range of 5 to 12, and specifically include cyclopentyl, cyclohexyl, cycloheptyl, cyclooctyl, cyclononyl, cyclodecyl, cycloundecyl, and cyclododecyl. More preferably, the cycloalkyl include cyclopentyl, cyclohexyl, cycloheptyl, and cyclooctyl. The aralkyl groups are not limited in these carbon numbers, but preferably they have a carbon number of 7 to 24. Specifically, they include benzyl, 2-benzyl-2-propyl, β-phenyl-ethyl, α,α-dimethylbenzyl, ω-phenyl-butyl, ω,ω-dimetyl-ω-phenyl-butyl, ω-phenyl-dodecyl, ω-phenyl-octadecyl, ω-phenyl-eicosyl, ω-phenyl-docosyl groups. Preferably, they are benzyl, 2-benzyl-propyl, β-phenyl-ethyl, α,α-dimethylbenzyl, ω-phenyl-butyl, ω,ω-dimetyl-ω-phenyl-butyl, ω-phenyl-dodecyl, and ω-phenyl-octadecyl groups, and more specifically are benzyl, 2-benzyl-propyl, β-phenyl-ethyl, α,α-dimethylbenzyl, ω-phenyl-butyl, and ω,ω-dimetyl-ω-phenyl-butyl groups. Alkylthio groups are substituents in which oxygen in the ether linkage of an alkoxy group is replaced with sulfur. An aryloxy group generally means a substituent formed with aromatic hydrocarbons having an ether linkage therebetween. In addition, in the present invention, aryloxy groups include substituents formed with an aromatic hydrocarbon having a carbon number of 6 to 24 and a saturated or unsaturated heterocycle which have an ether linkage therebetween. This hydrocarbon and heterocycle may have no substituent or have alkyl or alkoxy having a carbon number of 1 to 8 therein. The aryl thioether groups are substituents in which oxygen in the ether linkage of an aryloxy group is replaced with sulfur. The aryl groups, preferably, have a carbon number of 6 to 24, and specifically include phenyl, 1-naphthyl, 2-naphthyl, 4-biphenyl, phenanthryl, 2-fluorenyl, 9-fluorenyl, 2-anthracenyl, and 9-anthracenyl. More preferably, the aryl groups include phenyl, 1-naphthyl, 2-naphthyl, and 4-biphenyl. These aryl groups may further have alkyl or alkoxy having a carbon number of 1 to 8 therein. The heterocyclic groups have a cyclic structure having an atom other than carbon, such as nitrogen, oxygen, or sulfur. They may be saturated or unsaturated and preferably unsaturated. Specifically, they include thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, quinolyl, isoquinolyl, phthalazinyl, naphthyridinyl, quinoxalinyl, quinazolinyl, quinolinyl, phthalizinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl, and phenoxazinyl. These heterocycle groups may further have alkyl or alkoxy having a carbon number of 1 to 8 therein. In the amino groups, at least one hydrogen of two hydrogens thereof may be replaced with alkyl having a carbon number of 1 to 25, cycloalkyl having a carbon number of 5 to 12, aryloxy including aromatic hydrocarbons having a carbon number of 6 to 24, aryl having a carbon number of 6 to 24, heterocyclic, or the like. In this instance, aryl having a carbon number of 6 to 24 and heterocyclic may further have alkyl or alkoxy having a carbon number of 1 to 8 therein. In the silyl groups, at least one of hydrogen of three hydrogens thereof may be replaced with alkyl having a carbon number of 1 to 25, cycloalkyl having a carbon number of 5 to 12, aryloxy including aromatic hydrocarbons having a carbon number of 6 to 24, aryl having a carbon number of 6 to 24, a heterocyclic group, or the like. The aryl having a carbon number of 6 to 24 and the heterocyclic may further have alkyl or alkoxy having a carbon number of 1 to 8 therein. The fused aromatic ring and alicyclic ring formed with adjacent substituents may have a substituent or not.

Preferred diketopyrrolo[3,4-c]pyrrole derivatives include the following.

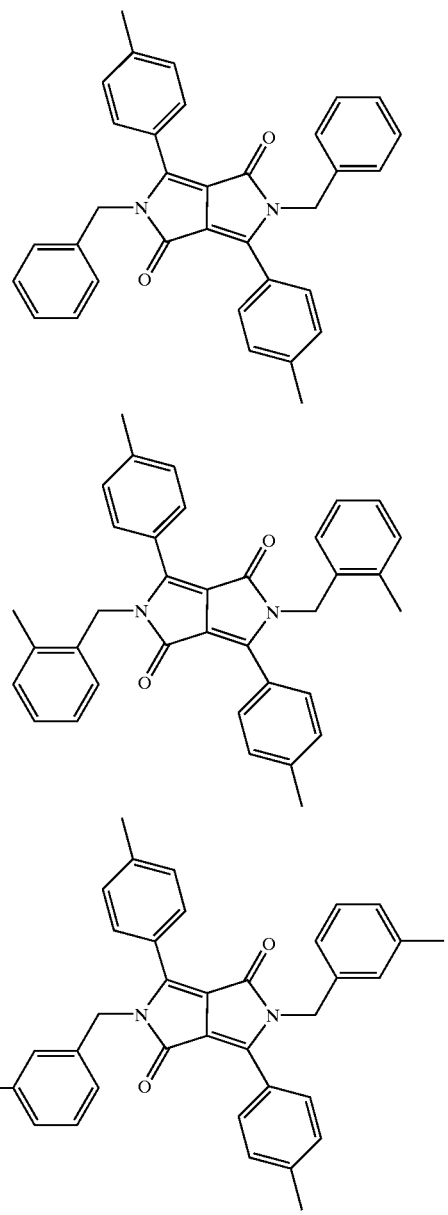

31
-continued
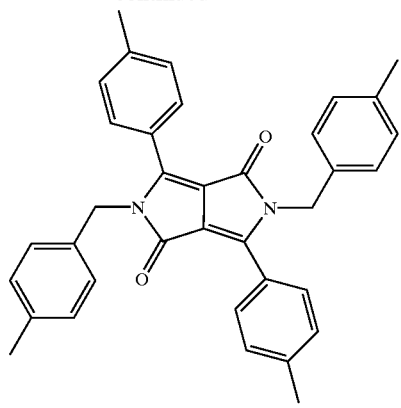
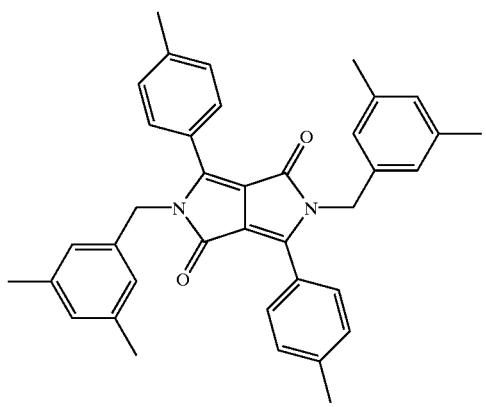
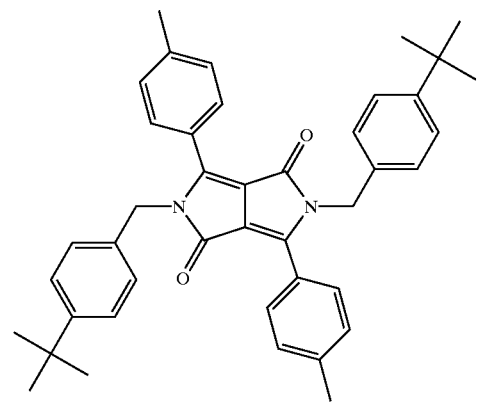
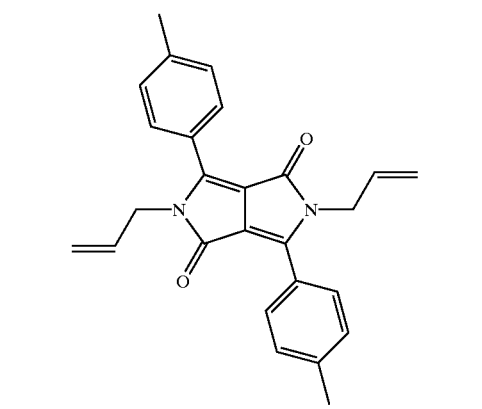
32
-continued
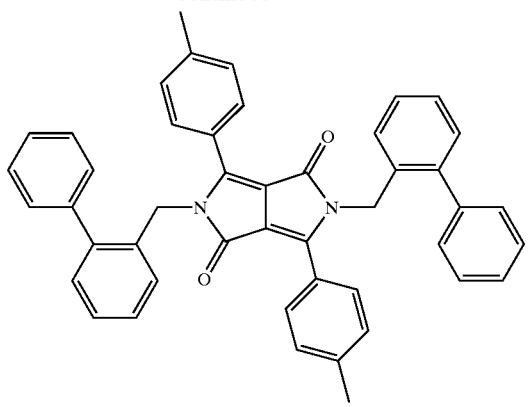
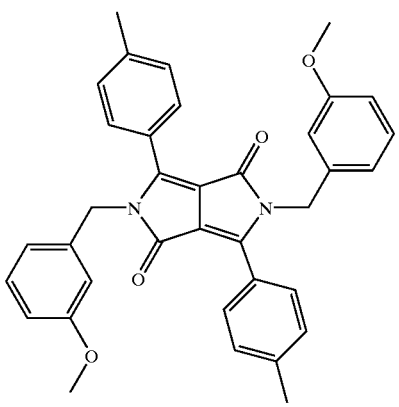
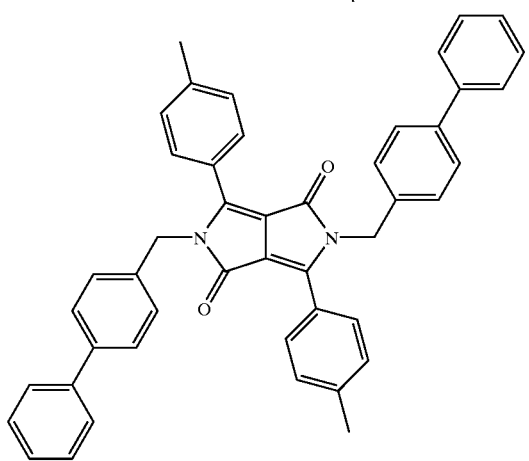
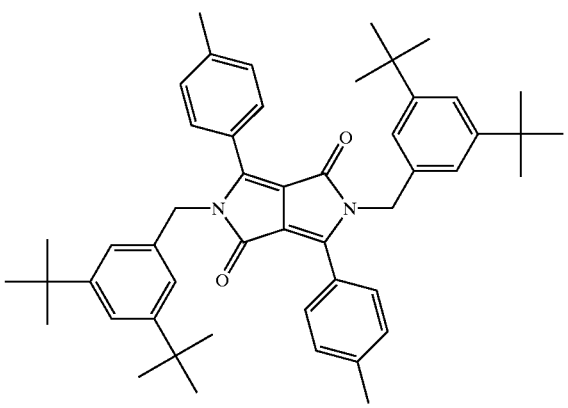

33
-continued
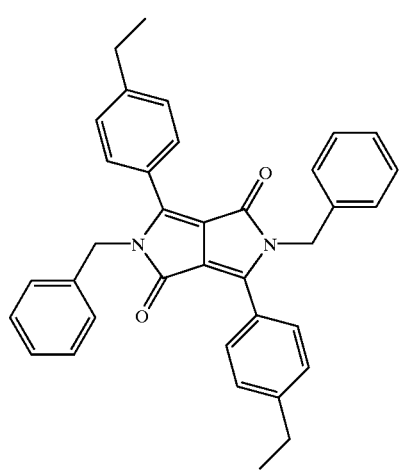
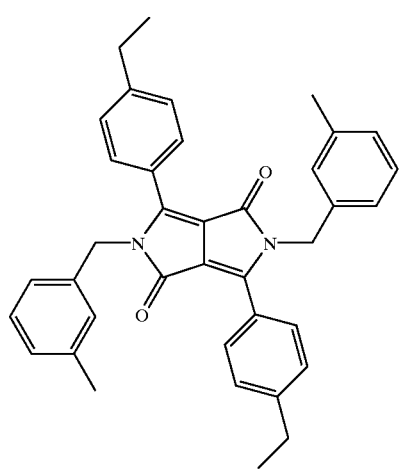
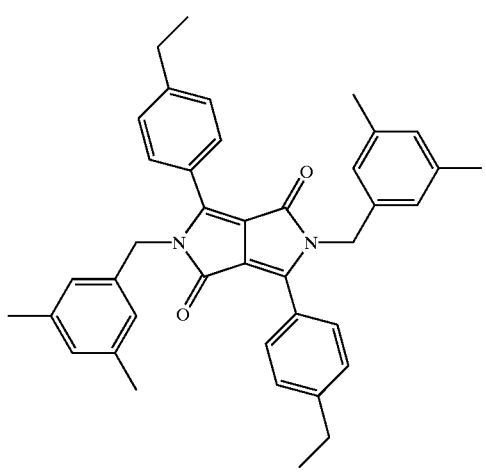
34
-continued
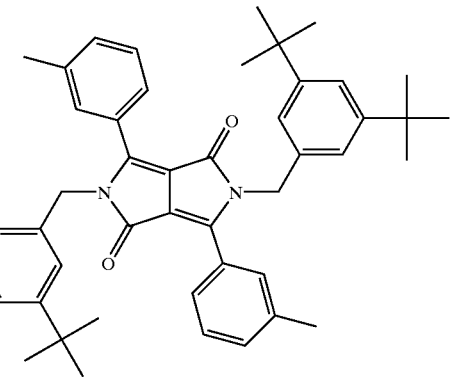
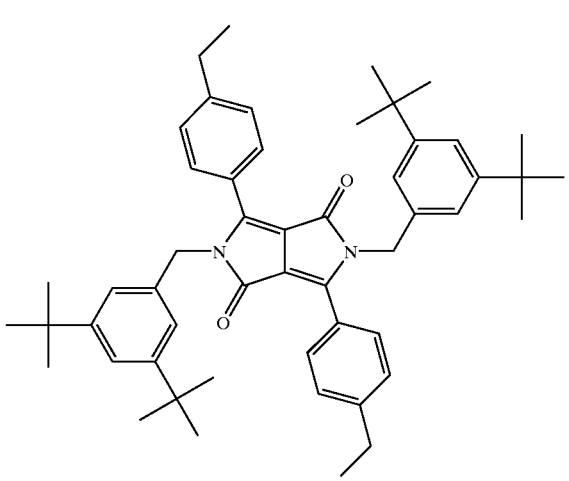
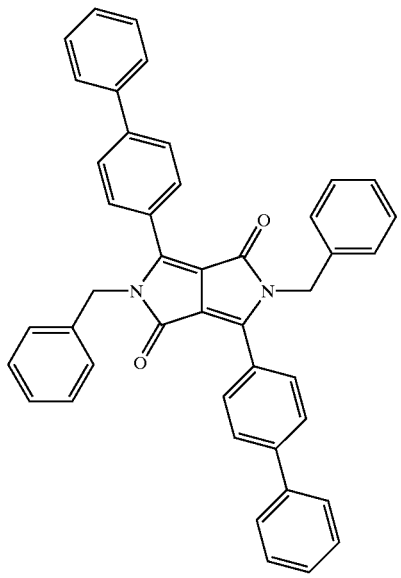

35
-continued
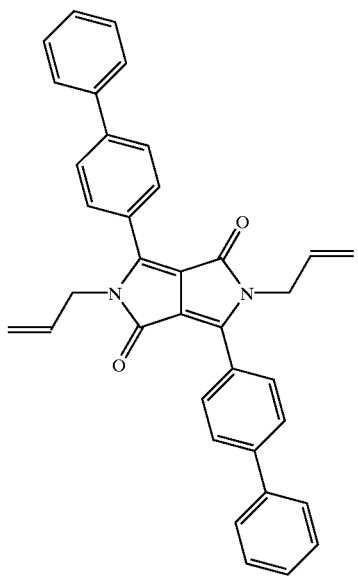
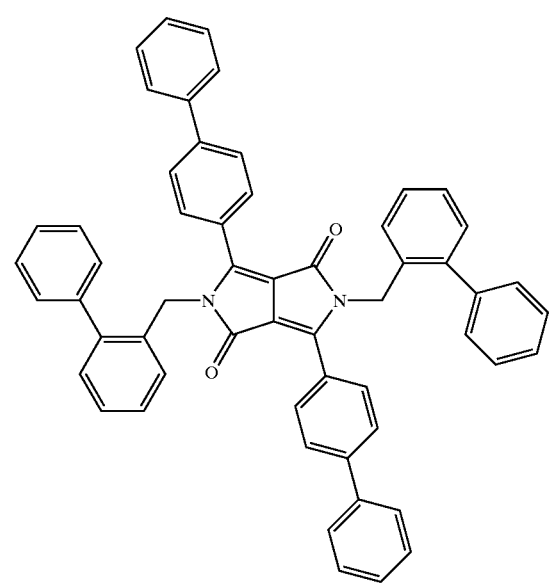
36
-continued
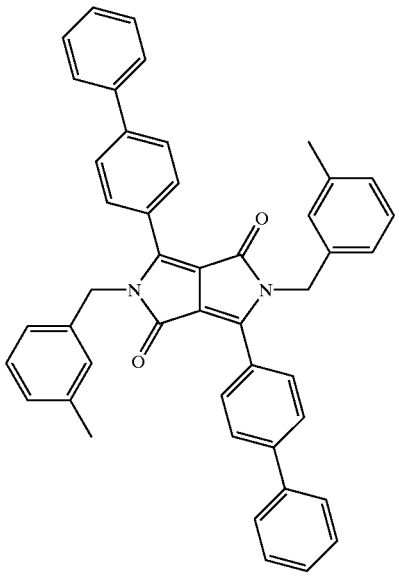
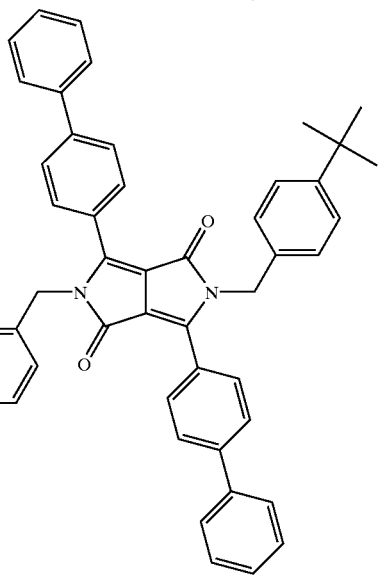
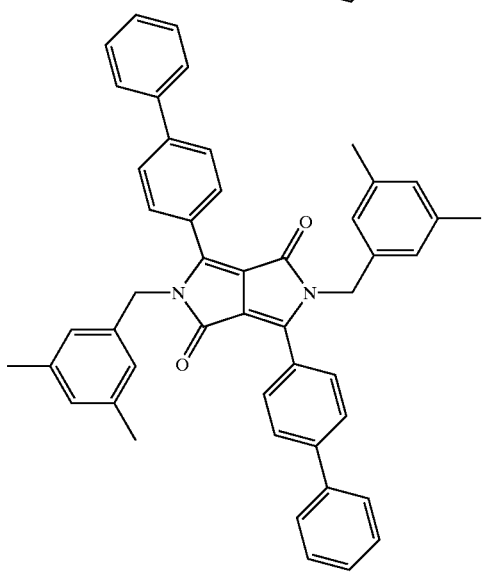

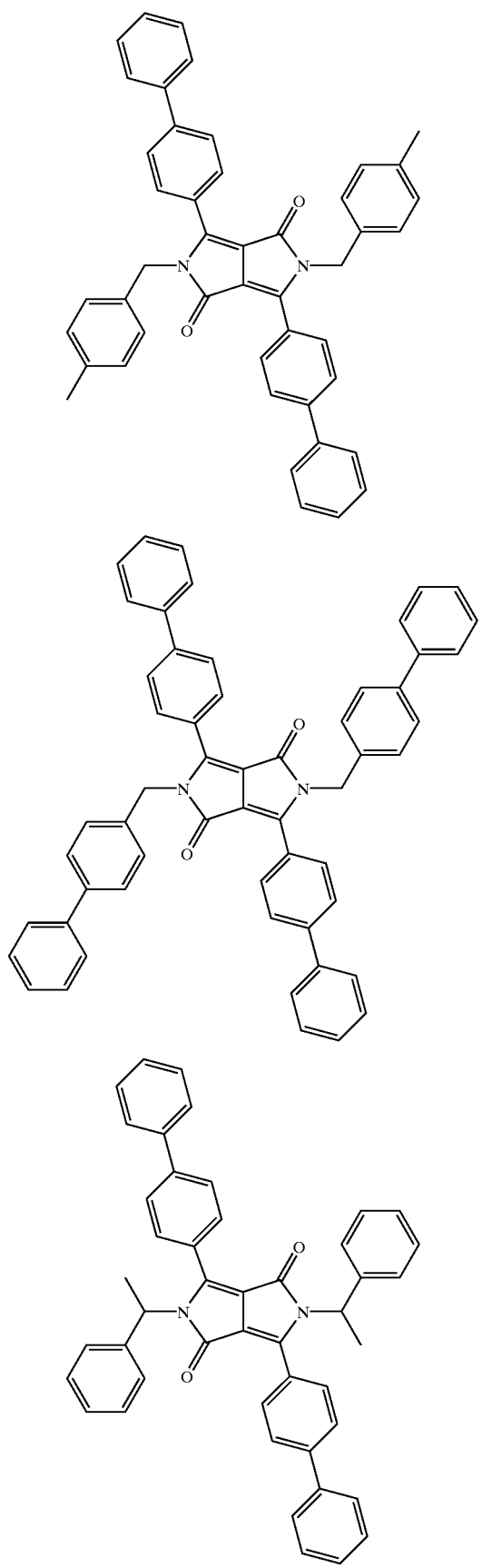
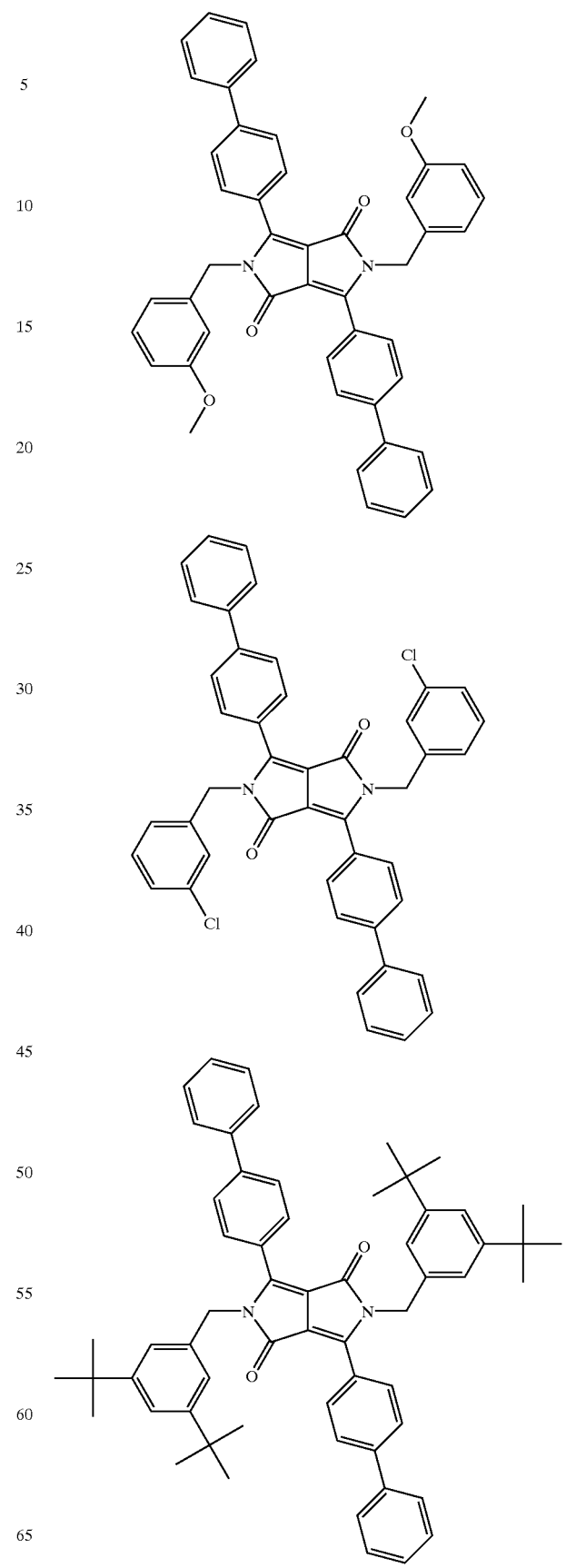

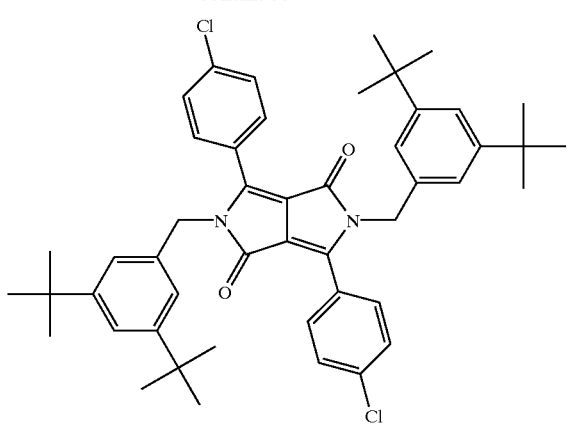
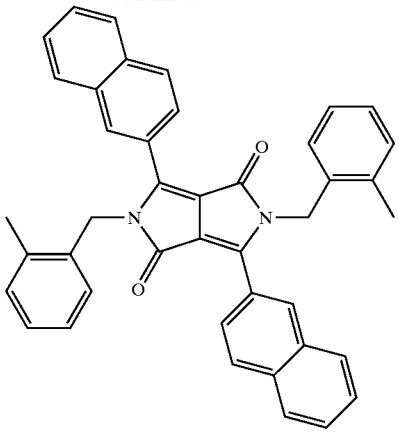
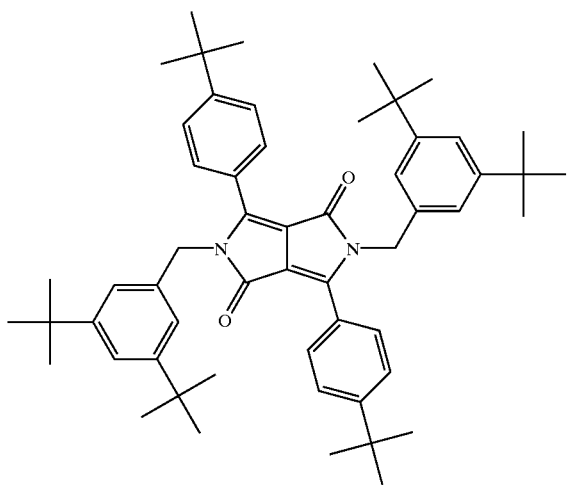
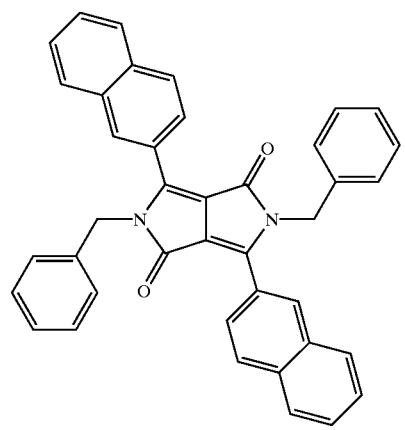
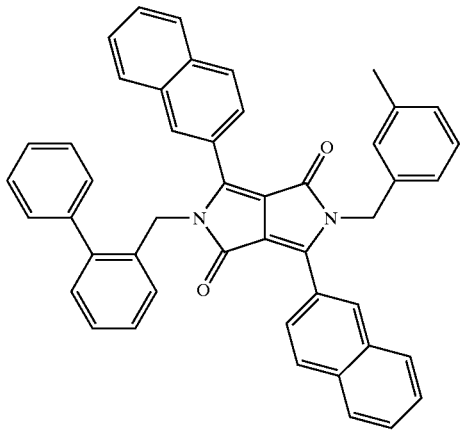

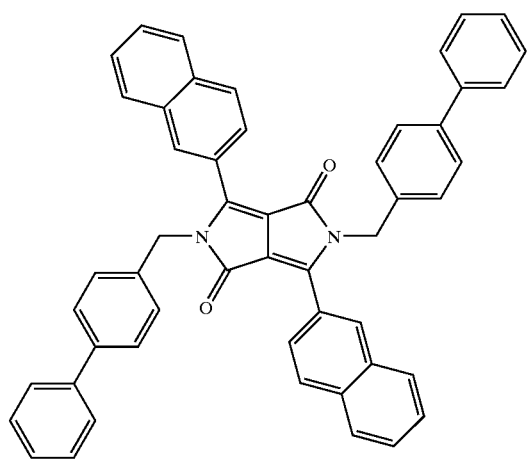
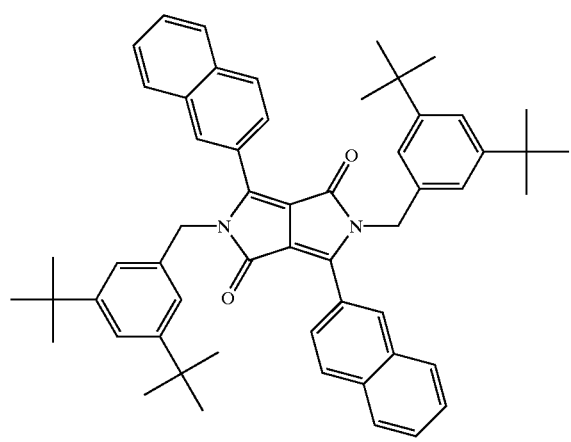
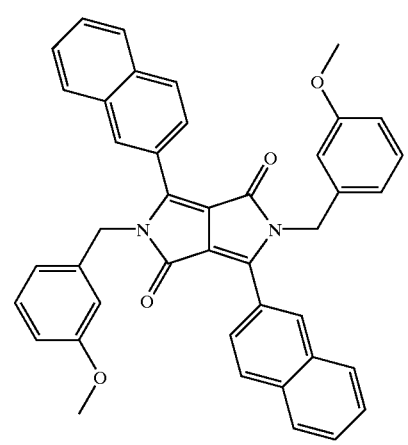
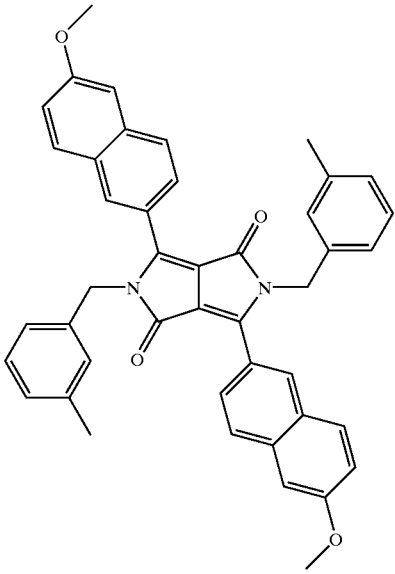
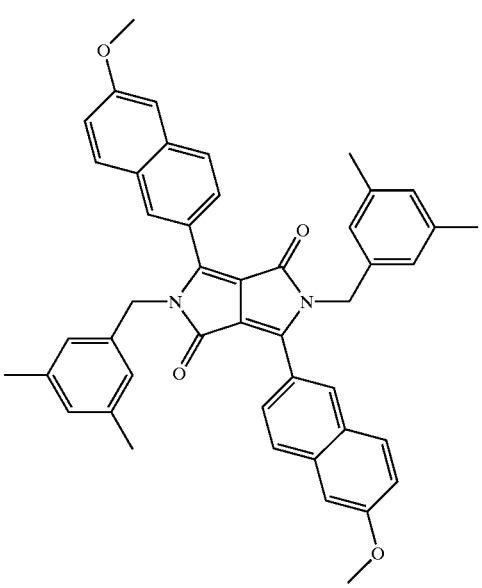
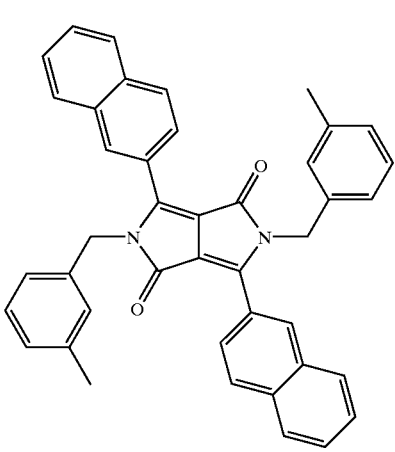

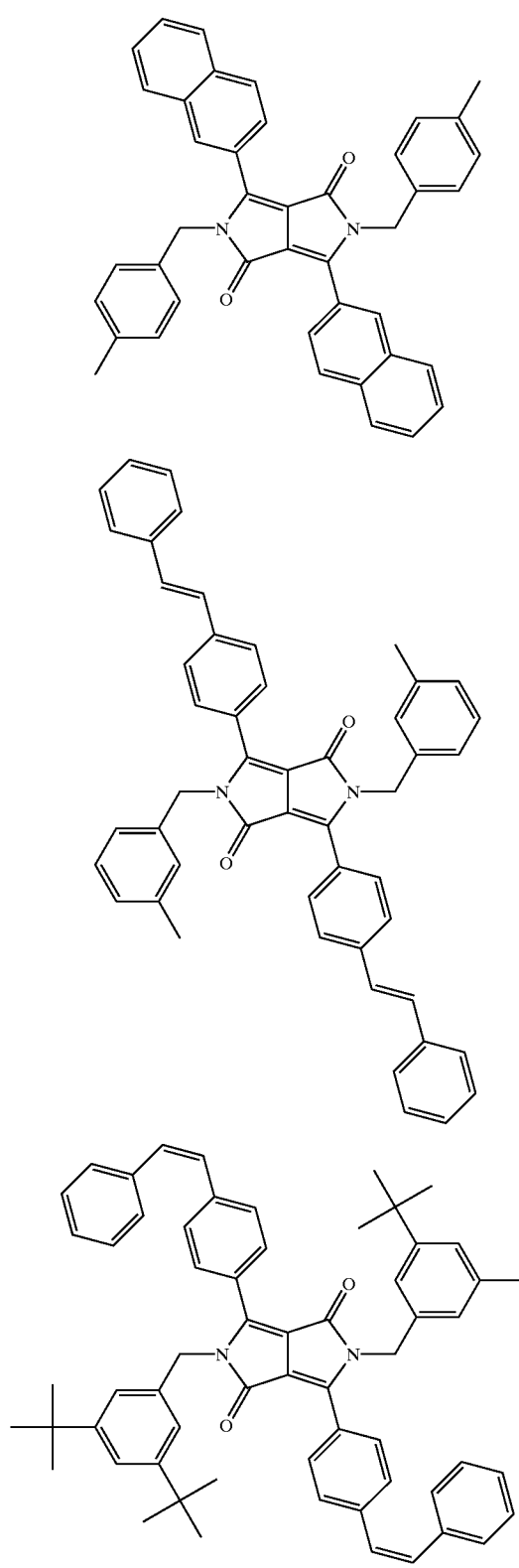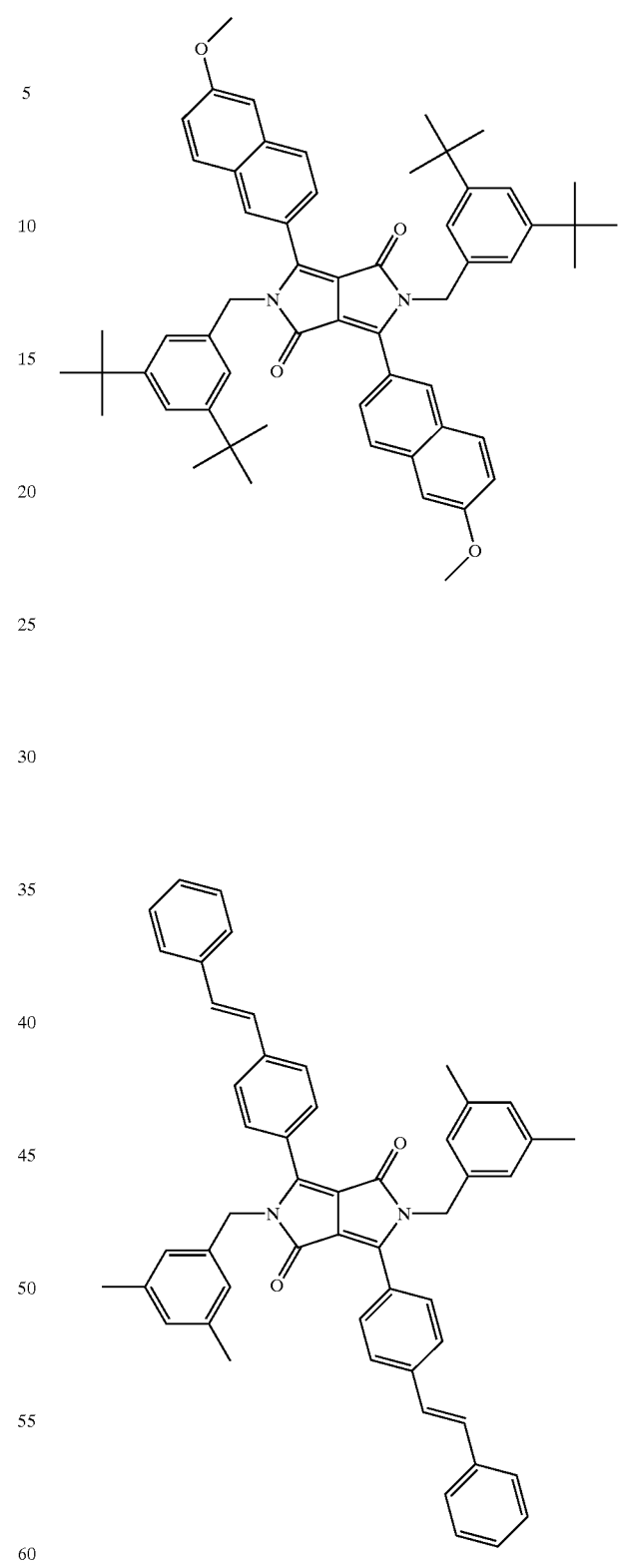

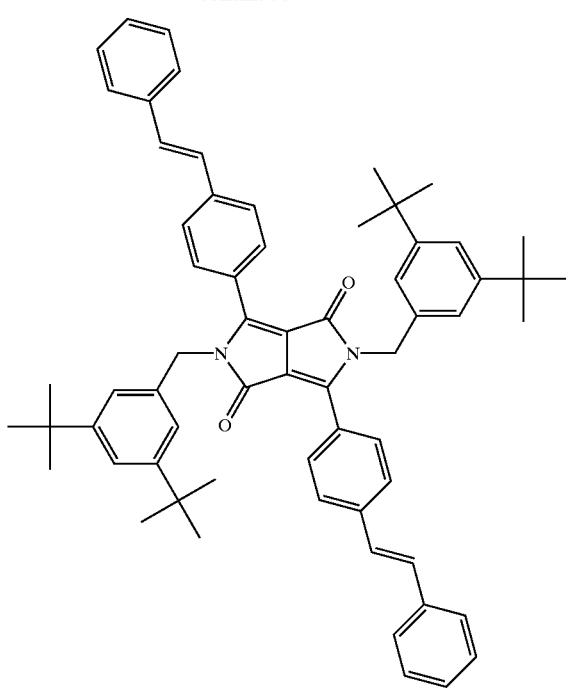
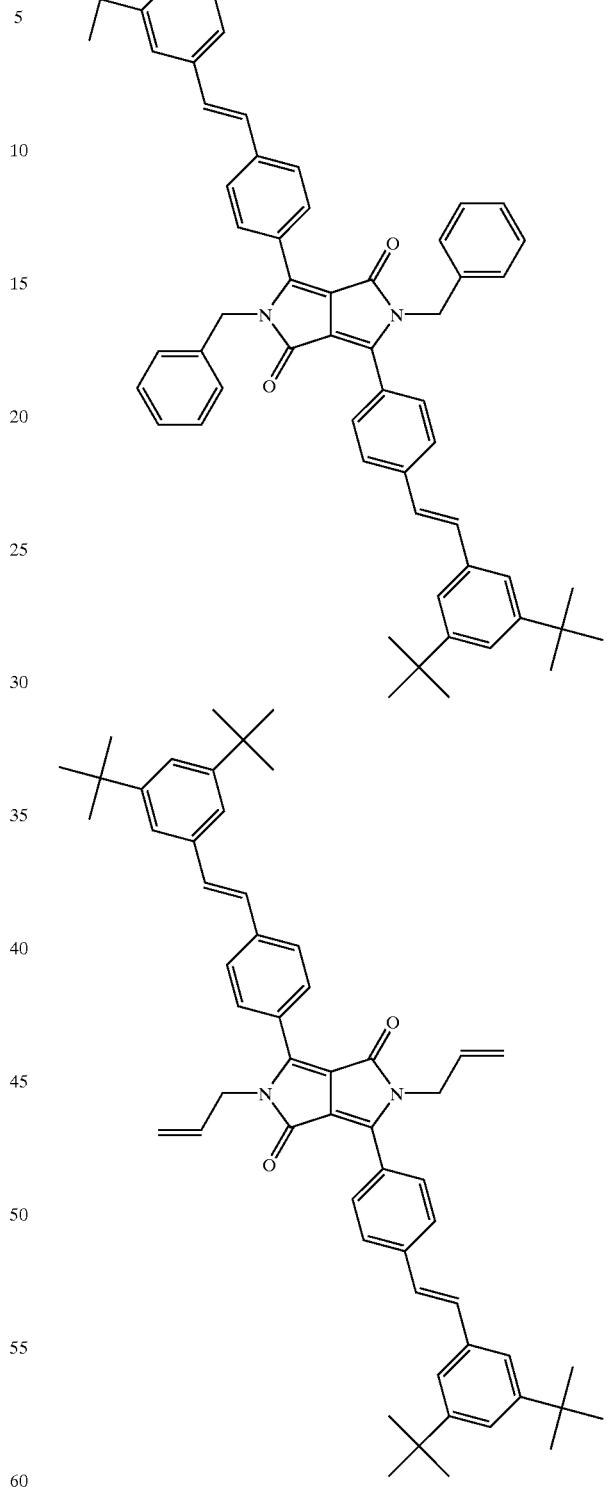

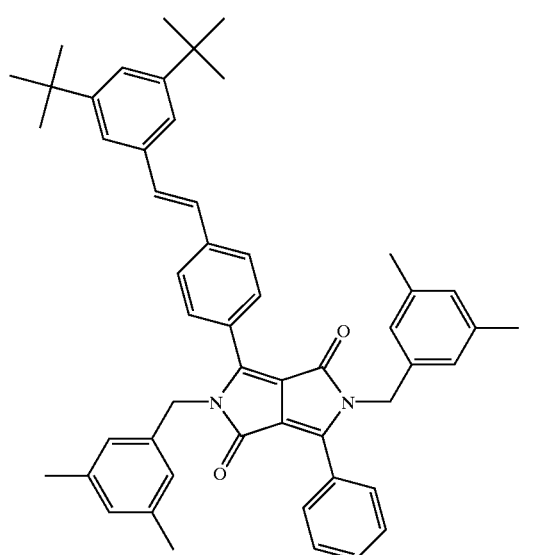
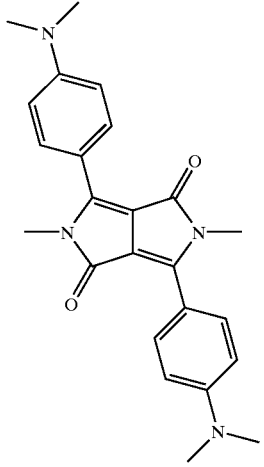
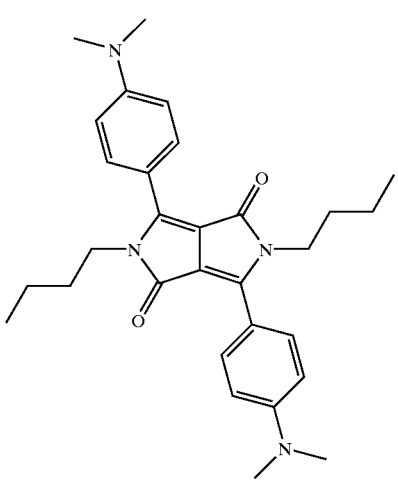
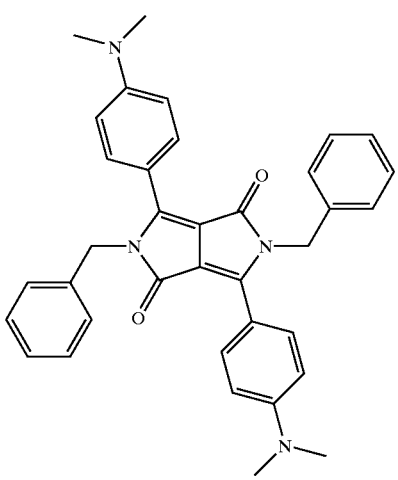

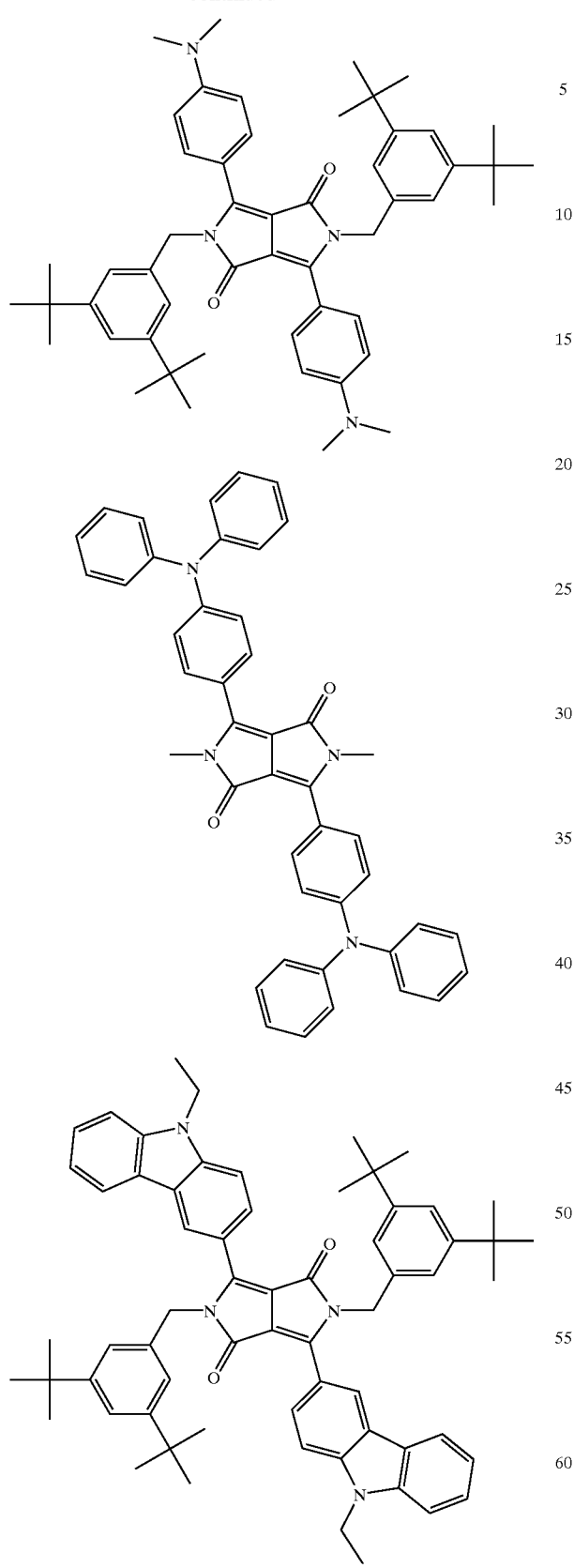
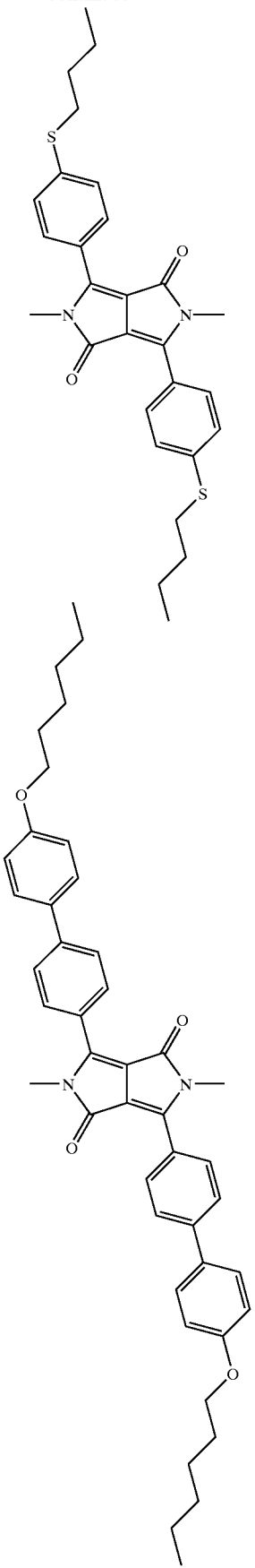

51
-continued
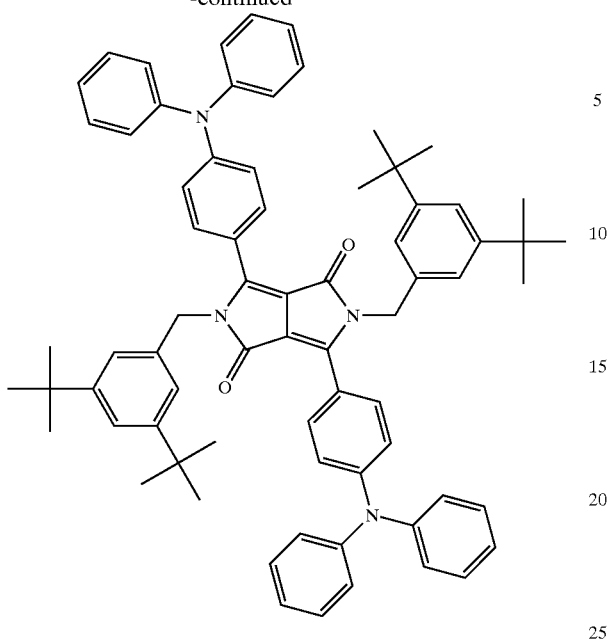
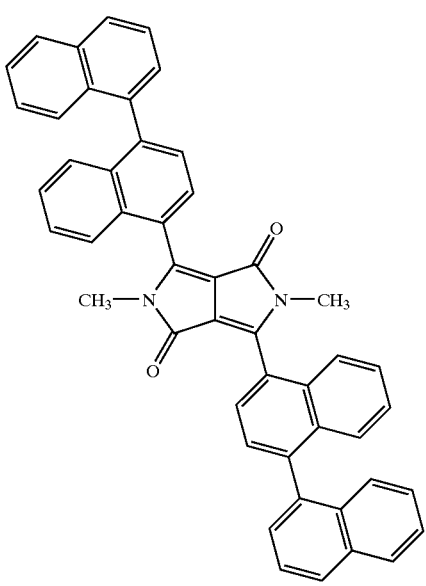
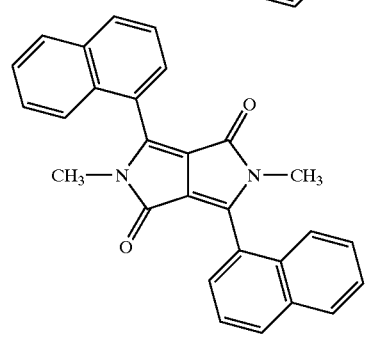
52
-continued
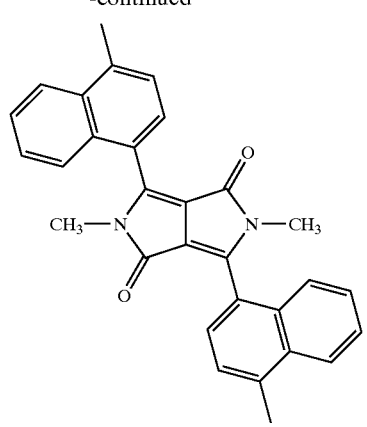
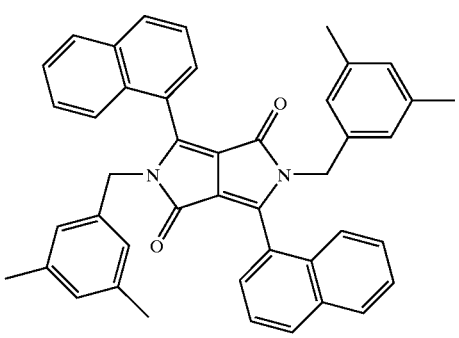
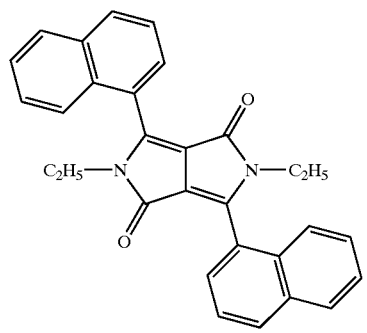

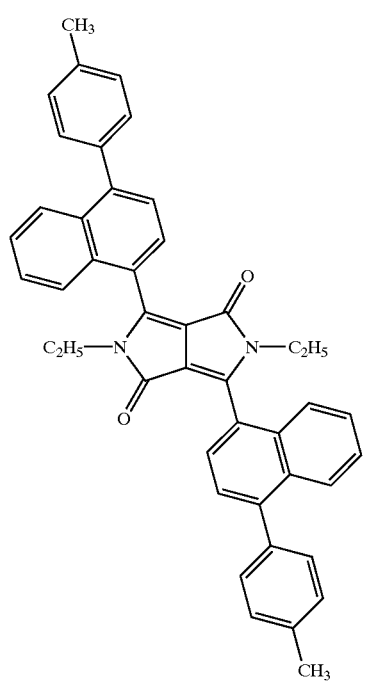
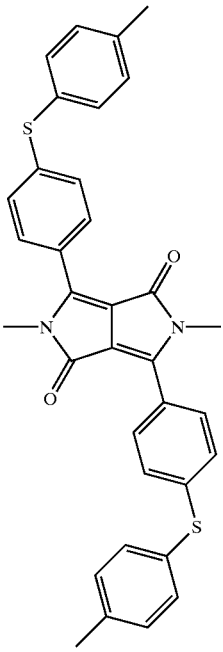
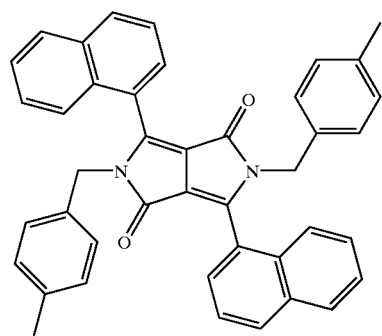
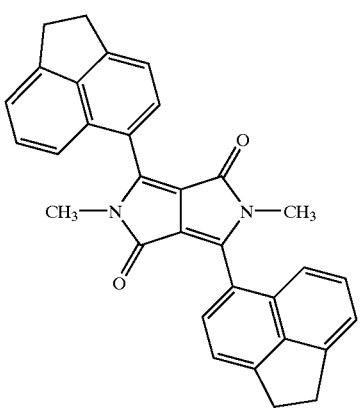
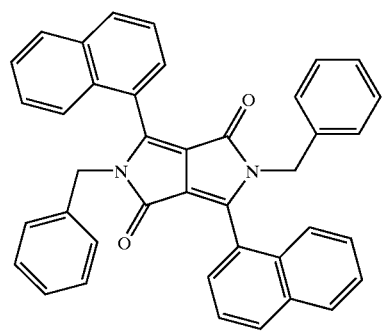
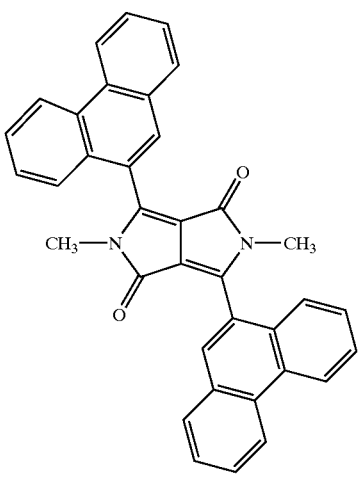

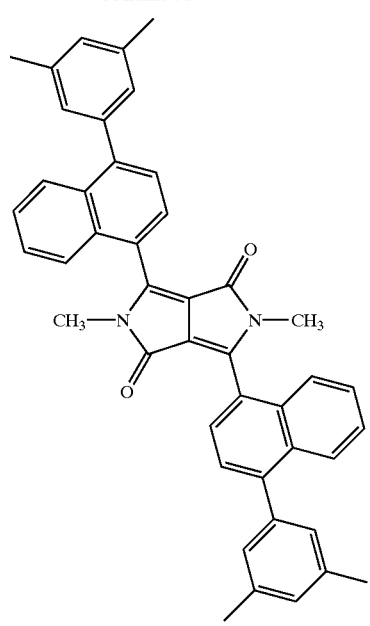
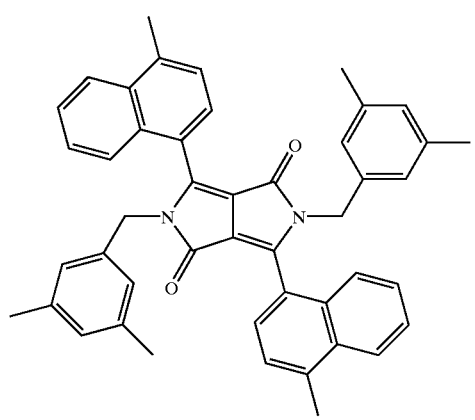
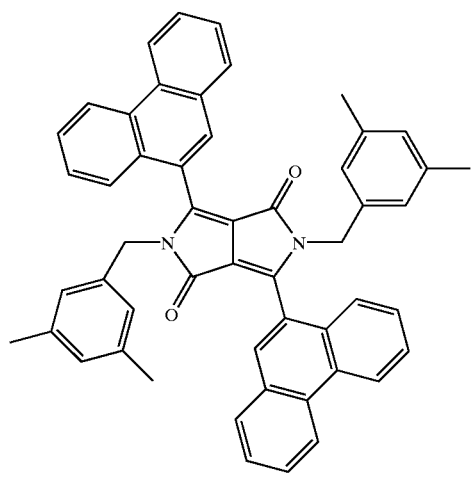
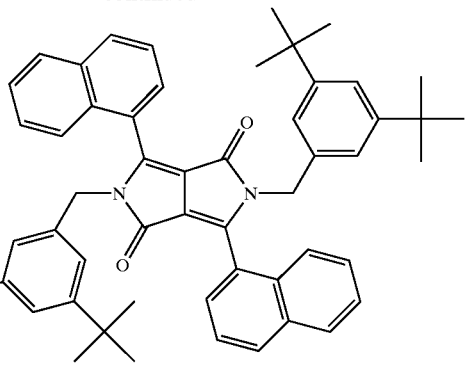
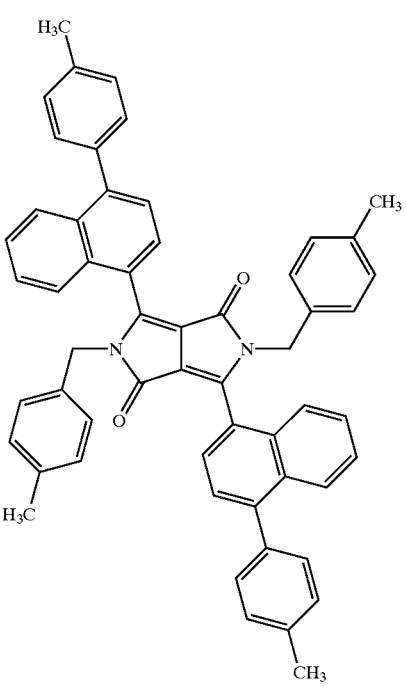
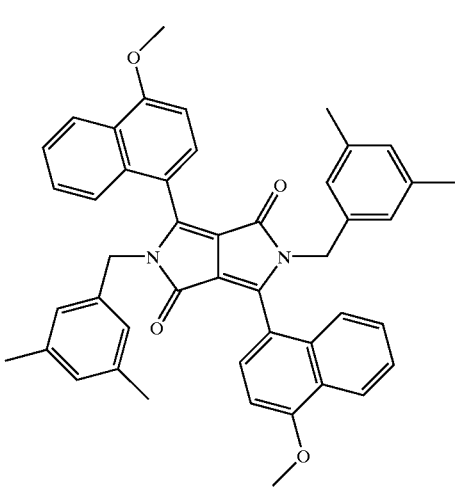

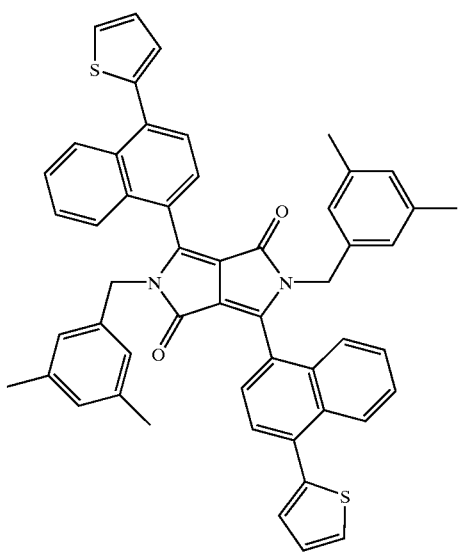
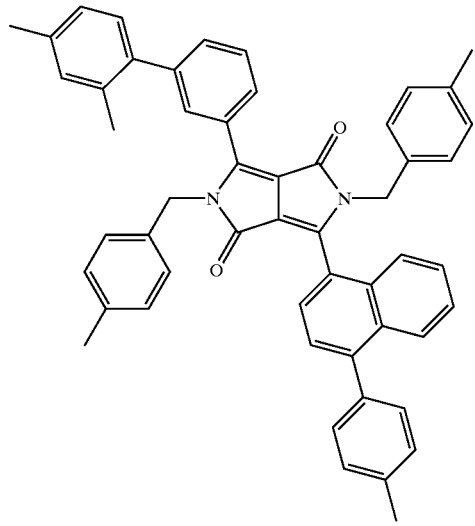
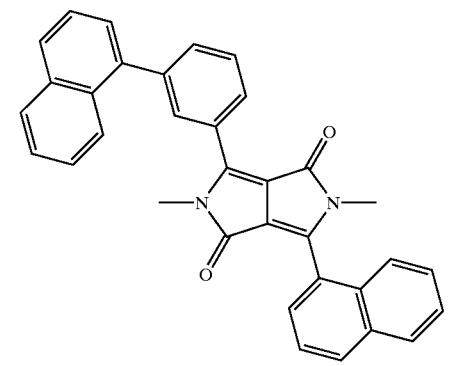
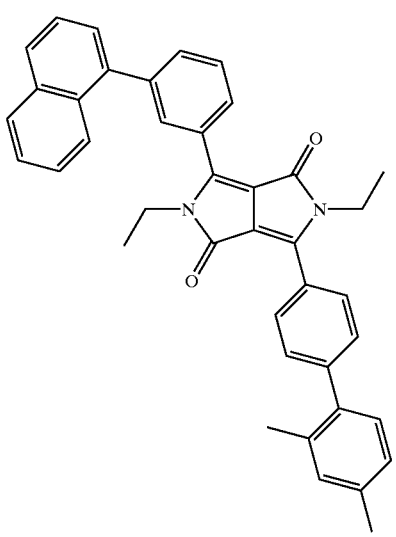
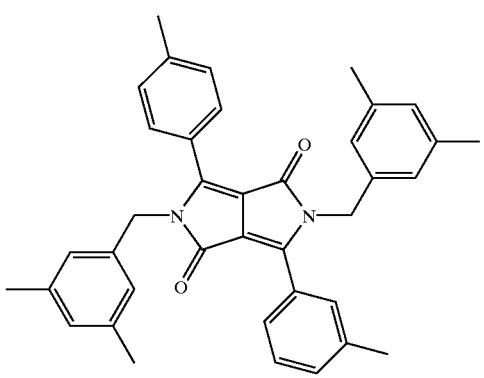
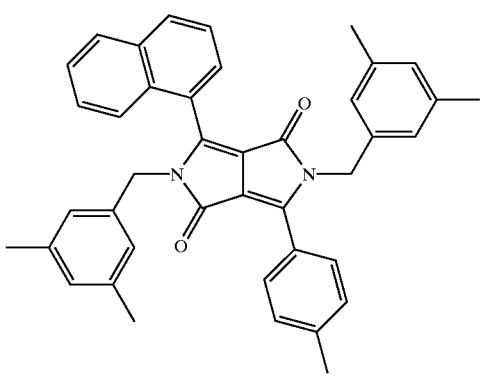
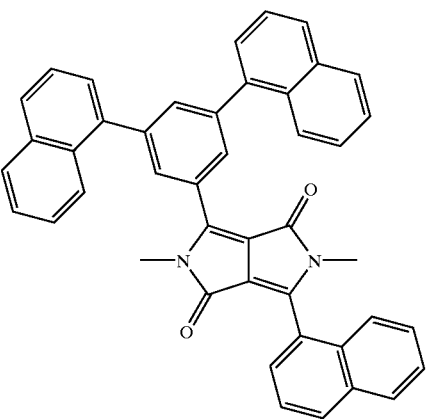

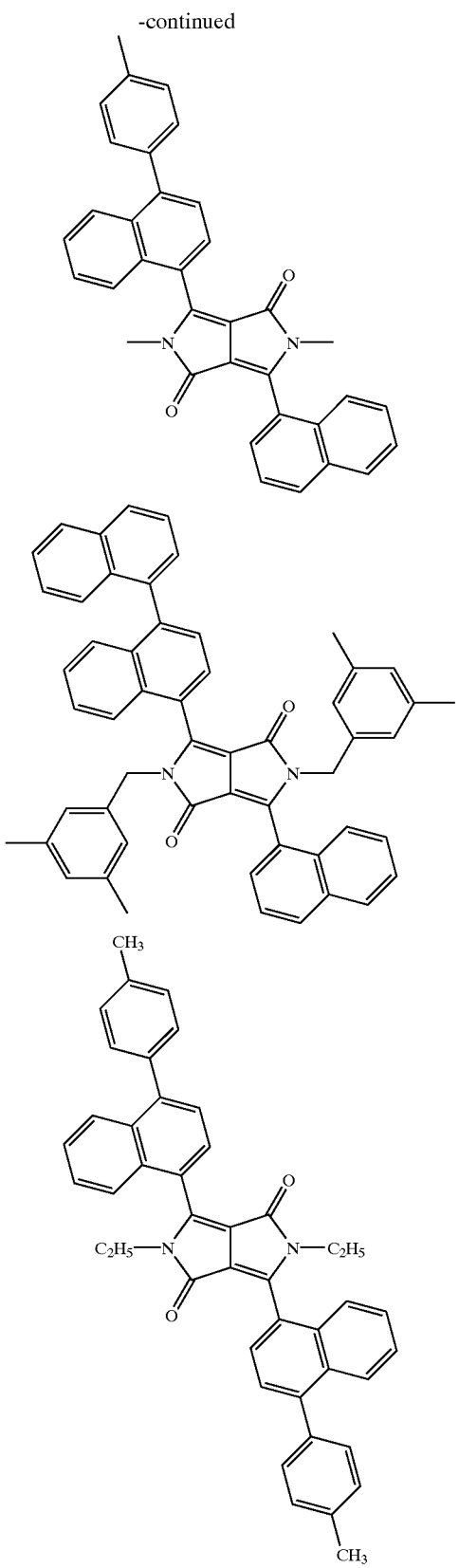

The diketopyrrolo[3,4-c]pyrrole derivatives are prepared in accordance with, for example, embodiments of EP Unexamined Patent Application Publication Nos. 0094911 and 0133156. Aromatic nitrile and diisopropyl succinate are heated together in t-amyl alcohol in the presence of potassium-t-butoxide to prepare a diketopyrrolopyrrole precursor. The diketopyrrolopyrrole precursor is heated with an alkyl halide in dimethylformamide (DMF) in the presence of potassium-t-butoxide and is followed by a general processing, Thus, the diketopyrrolo[3,4-c]pyrrole is obtained.

The diketopyrrolo[3,4-c]pyrrole derivatives of the present invention are fluorescent, and most of the derivatives have a fluorescence quantum efficiency of 0.3 or more in toluene or DMF or have a molar absorptivity of 5000 or more.

In the present invention, organic fluorescent materials having a peak wavelength of 580 to 720 nm are used to generate red emission. Specifically, the organic fluorescent materials include fused derivatives of aromatic hydrocarbons such as terylene; fused heterocyclics such as pyridinothiadiazole, pyrazolopyridine, and diketopyrrolopyrrole; naphthalimido derivatives such as bis(diisopropylphenyl)perylenetetracarboxylic imido; perynones; rare earth complexes such as Eu complexes of which the ligand is acetylacetone or benzoylacetone and phenanthroline; 4-(dicyanomethylene)-2-methyl-6-(p-dimethylaminostyryl)-4H-pyran and the analogues thereof; metal phthalocyanine derivatives such as magnesium phthalocyanine and aluminum chlorophthalocyanine; metalloporphyrin derivatives such as zinc porphyrin; thiophenes; pyrroles; rhodamines; deazaflavin derivatives; coumarin derivatives; oxazines; phenoxazines; phenoxazones; quinacridones; benzothioxanthene and the analogues thereof; and dicyanoethenylarenes.

Preferably, the organic fluorescent materials have a pyrromethene skeleton represented by formula (5) or a metal complex thereof to generate a red emission having excellent chromatic purity.

(5)

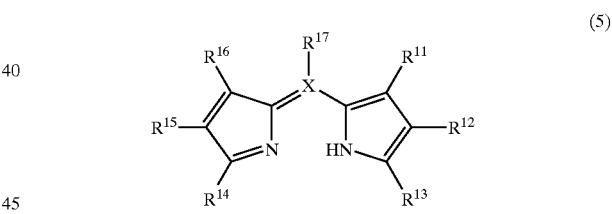

At least one of $R^{11}$ to $R^{17}$ has an aromatic ring or form a fused ring with an adjacent substituent. The others are each a substituent selected from the group consisting of hydrogen, alkyl, cycloalkyl, aralkyl, alkenyl, cycloalkenyl, alkynyl, hydroxyl, mercapto, alkoxy, alkylthio, aryl ethers, aryl thioethers, aryl, heterocyclic, halogens, haloalkane, haloalkene, haloalkyne, cyano, aldehyde, carbonyl, carboxyl, esters, carbamoyl, amino, nitro, silyl, siloxanyl, and a fused aromatic ring and an alicyclic ring formed with adjacent substituents. X represents carbon or nitrogen. If X is nitrogen, $R^{17}$ does not exist. The metal of the metal complex is selected from the group consisting of boron, beryllium, magnesium, chromium, iron, nickel, copper, zinc, and platinum.

These substituents are the same as in formula (1). Preferably, the organic fluorescent materials have a high fluorescence quantum yield to ensure increased luminance. Preferably, the following complex represented by formula (6) is used as a metal complex of the organic fluorescent materials having the pyrromethene skeleton.

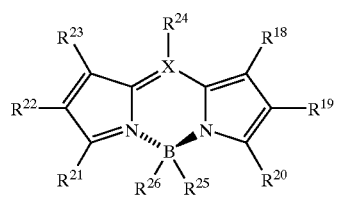

(6)

At least one of $R^{18}$ to $R^{24}$ has an aromatic ring or form a fused ring with an adjacent substituent. The others are each a substituent selected from the group consisting of hydrogen, alkyl, cycloalkyl, aralkyl, alkenyl, cycloalkenyl, alkynyl, hydroxyl, mercapto, alkoxy, alkylthio, aryl ethers, aryl thioethers, aryl, heterocyclic, halogens, haloalkane, haloalkene, haloalkyne, cyano, aldehyde, carbonyl, carboxyl, esters, carbamoyl, amino, nitro, silyl, siloxanyl, and a fused aromatic ring and an alicyclic ring formed with adjacent substituents. X represents carbon or nitrogen. If X is nitrogen, $R^{24}$ does not exist.

These substituents are the same as in formula (1).

More preferably, the pyrromethene metal complex represented by formula (1) is used to prevent the degradation of fluorescence intensity in a thin-film state and thus to generate light with high luminance.

Besides the metal complex represented by formula (1), exemplary metal complexes of the organic fluorescent materials having the pyrromethene skeleton include the following.

[63]

[64]

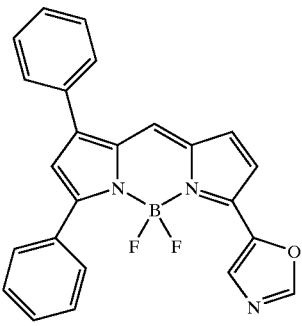

[65]

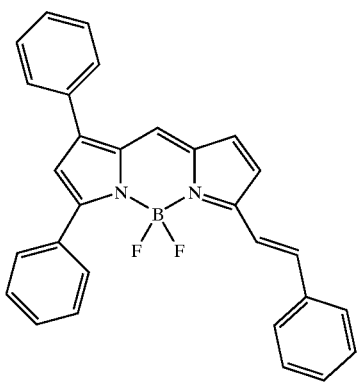

[66]

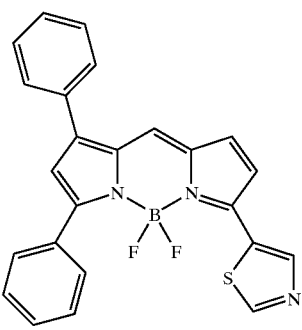

[67]

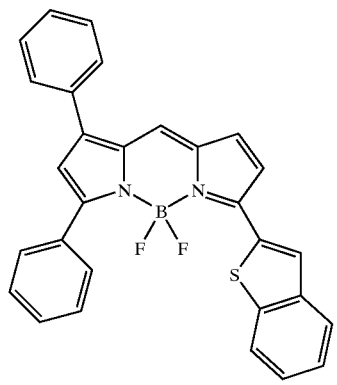

[68]

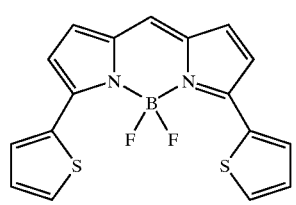

[69]

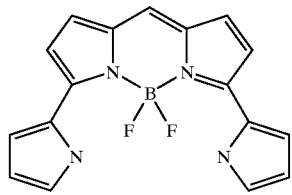
[70]
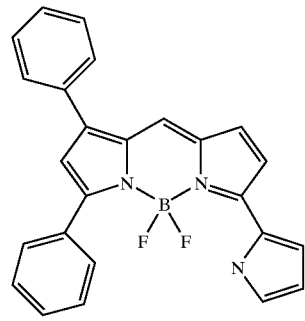
[75]
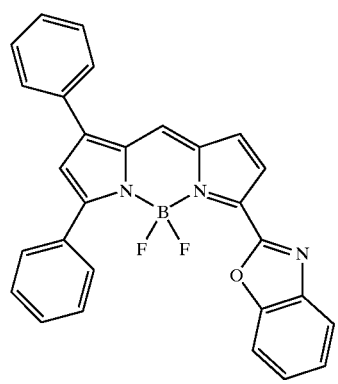
[71]
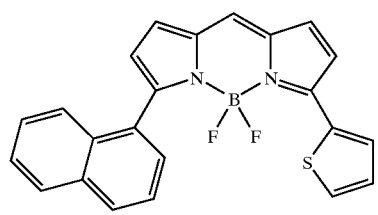
[76]
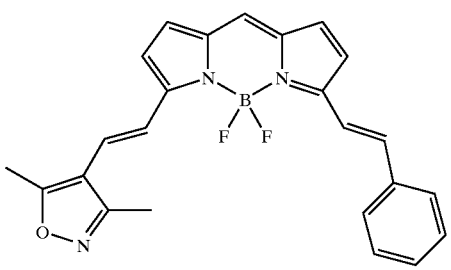
[77]
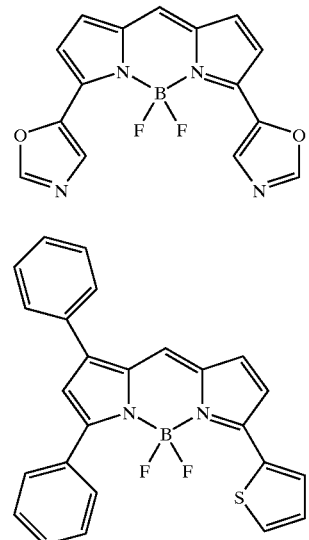
[72]
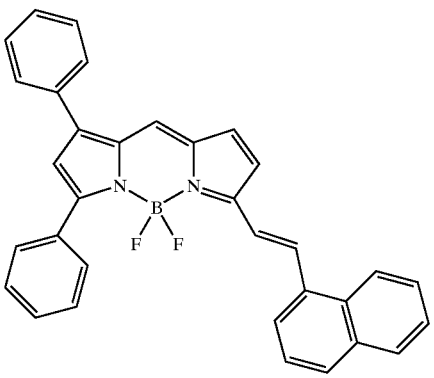
[78]
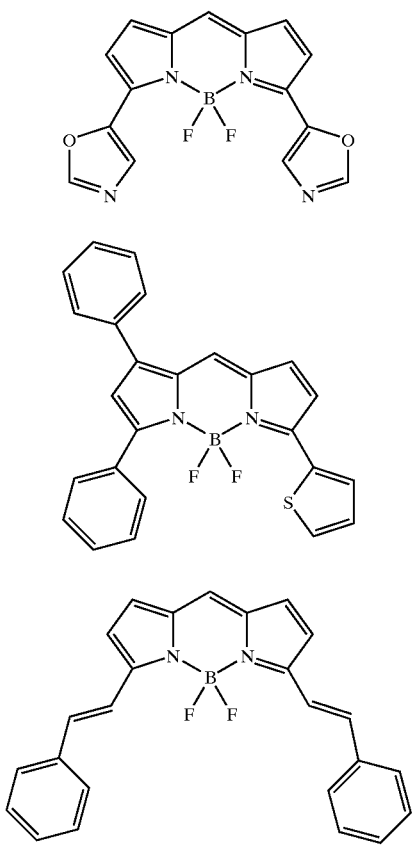
[73]
[74]
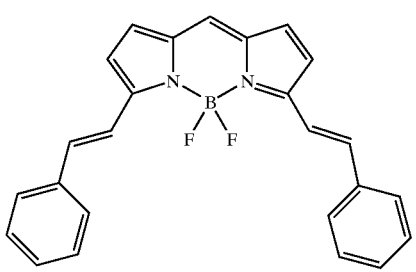
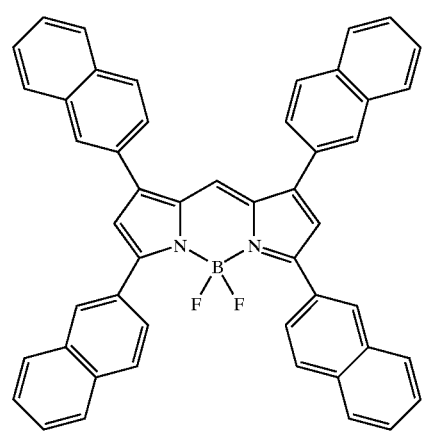
[79]

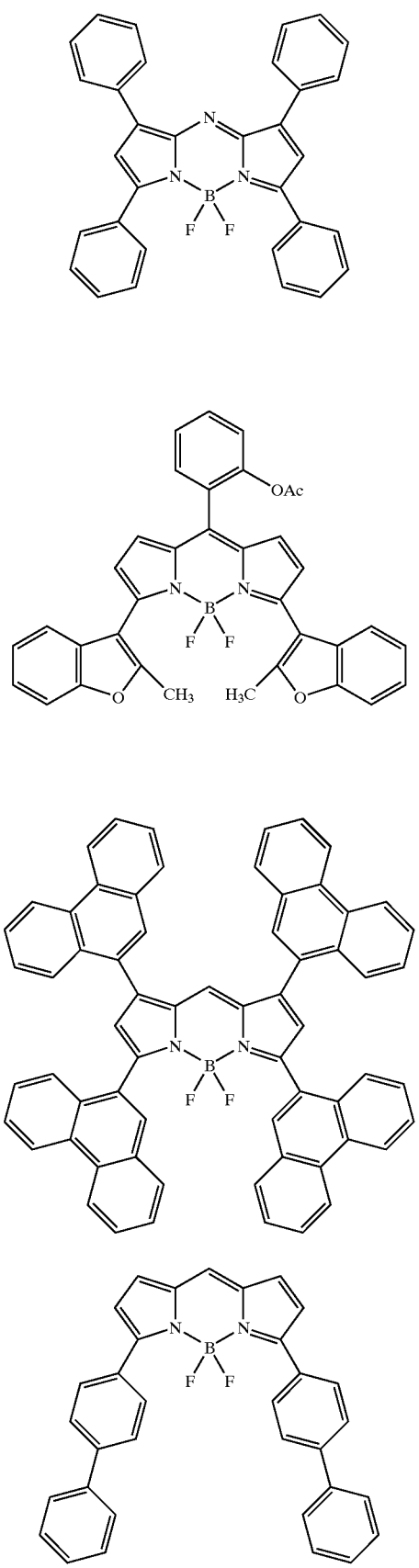
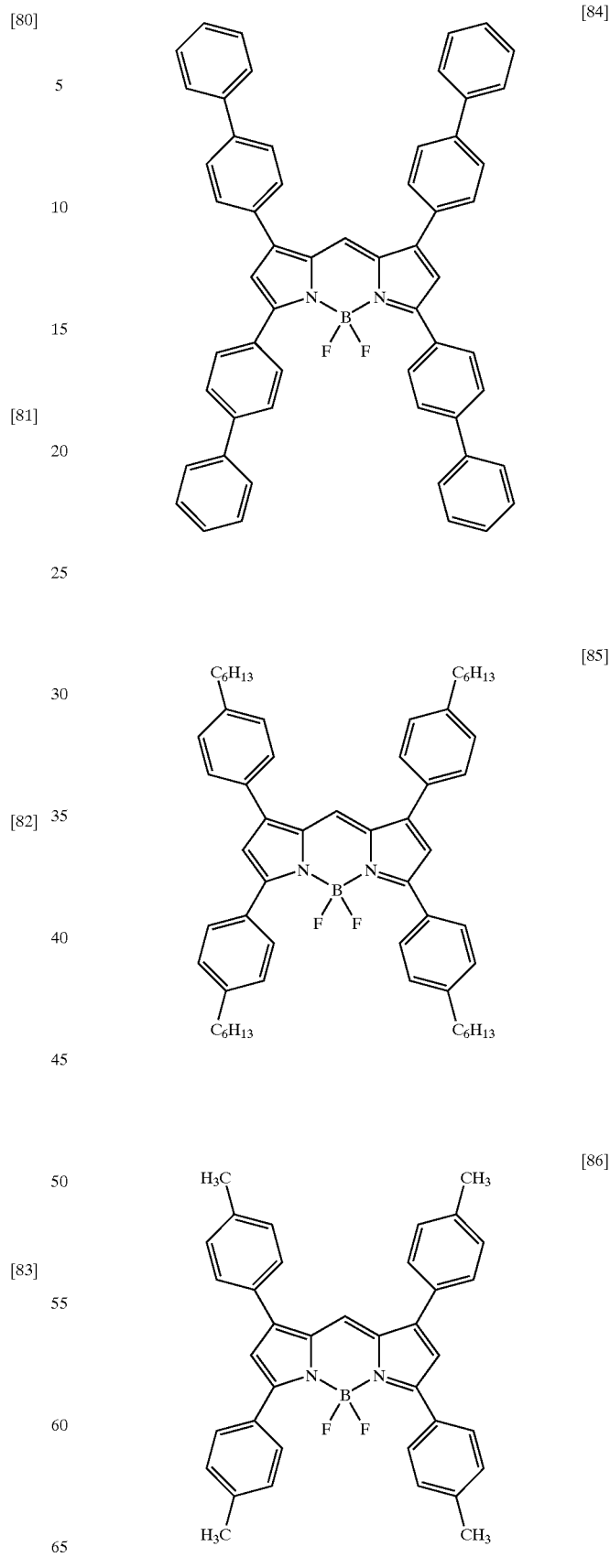

[87]
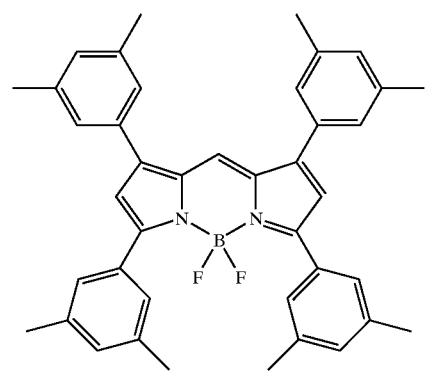
[88]
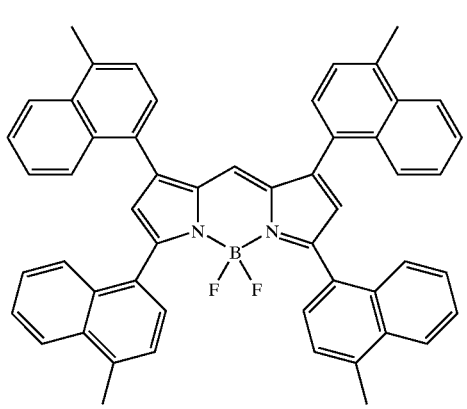
[89]
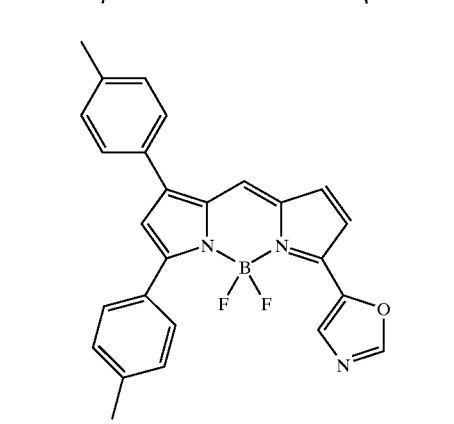
[90]
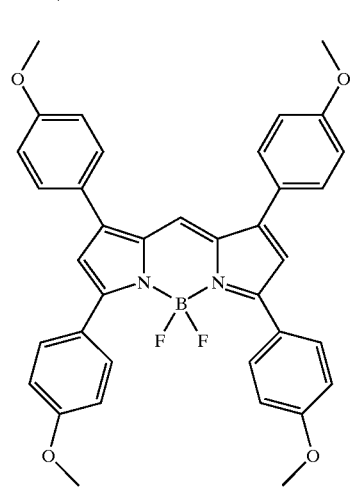
[91]
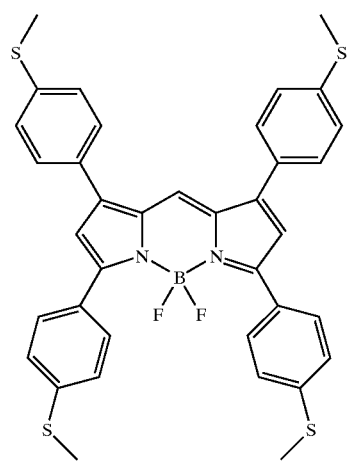
[92]
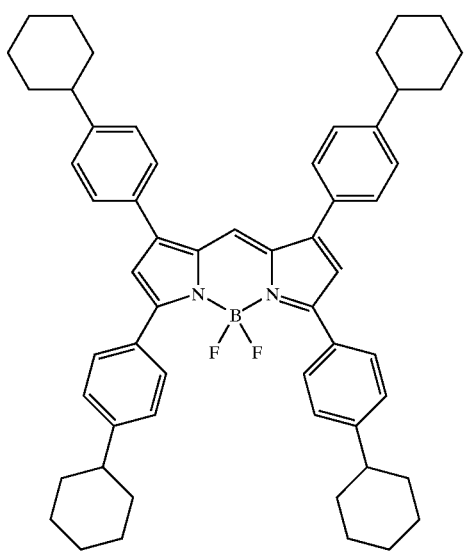
[93]
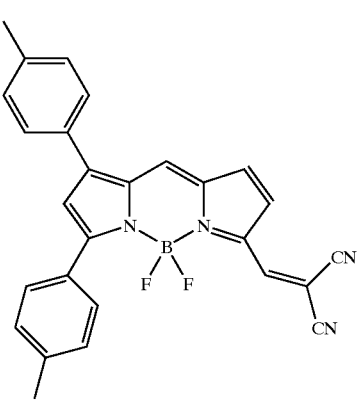

[94]
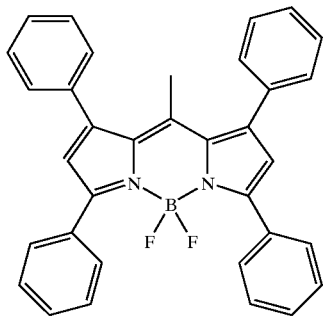
[99]
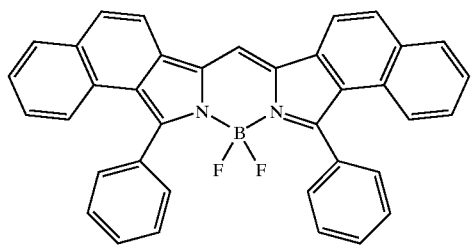
[95]
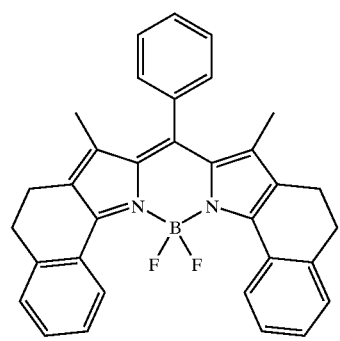
[100]
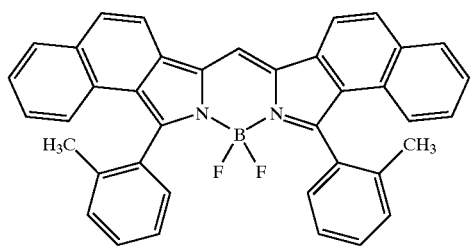
[96]
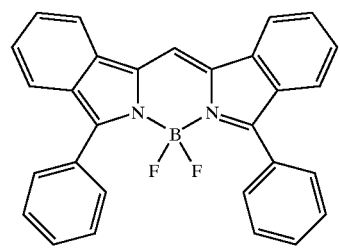
[101]
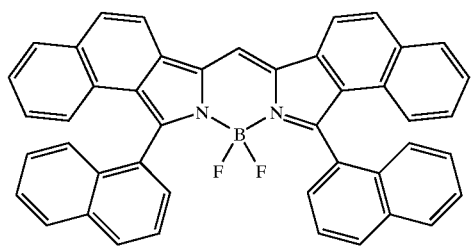
[97]
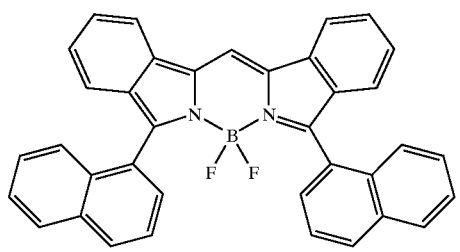
[102]
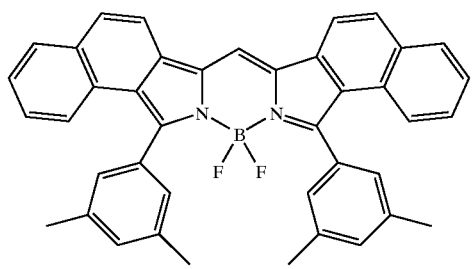
[98]
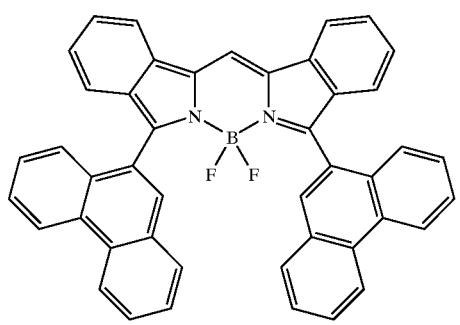
[103]
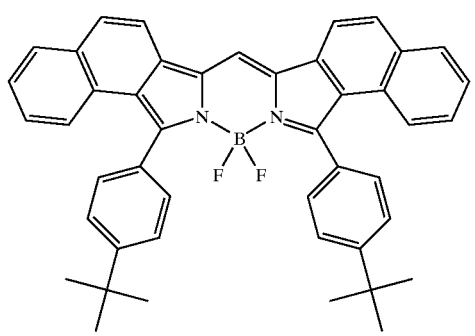

-continued

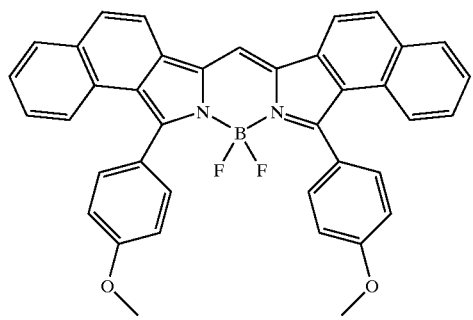
[104]

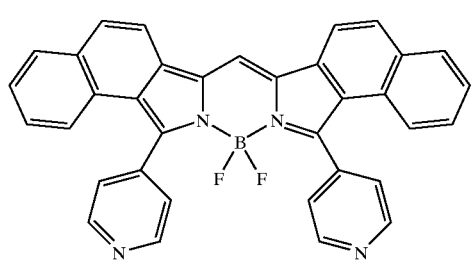
[105]

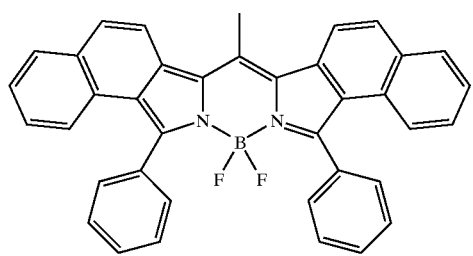
[106]

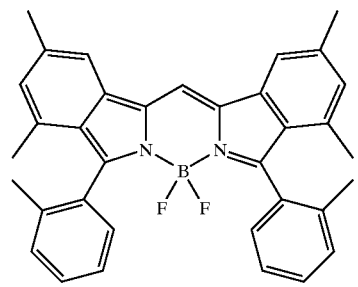
[107]

In order to transfer energy from a host material to dopant, it is important that the fluorescence spectrum of the host material overlaps the absorption spectrum (excitation spectrum) of the dopant. The fluorescent spectrum of a host, here, is measured when the host is in a thin-film state and the absorption (excitation) spectrum and the fluorescent spectrum of dopant are measured when the dopant is in a solution state. This is because the host is in a thin-film state and the dopant molecularly doped in the host is in almost the same state as in a solution, in the LED. If a material having excellent chromatic purity, such as the above-described substances having a pyrromethene skeleton and metal complexes thereof, is used as a dopant, the dopant exhibits a small Stokes shift (the difference between the peaks of the excitation spectrum and the fluorescent spectrum) of several to tens of nanometers. When the dopant is used for generating a red emission having a peak wavelength of 580 to 720 nm and high chromatic purity, the dopant exhibits an absorption (excitation) spectrum in the areas of yellow, golden yellow, orange, tango, and red (in the range of 540 to 720 nm). If a host material exhibits a fluorescent spectrum in a shorter wavelength band of yellowish green, green, blue green, blue, lavender, and purple than the yellow band and thus the overlapped spectrums is small, energy transfer becomes difficult and thus light may not be emitted from the dopant. If emitted, the light would be whitened due to partial emission from the host material and thus would not become red with high chromatic purity.

Accordingly, the host material preferably has a fluorescent peak wavelength of 540 to 720 nm, so that the dopant can emit light of 580 to 720 nm with high luminance and high chromatic purity. Substances having a yellow, golden yellow, an orange, a tango, and a red fluorescence correspond to such host materials. When a diketopyrrolo[3,4-c]pyrrole derivative represented by formula (1) is used as a host material, therefore, the derivative preferably has a yellow, a golden yellow, an orange, a tango, or a red fluorescence.

In the case of (b), the LED material comprises a diketopyrrolo[3,4-c]pyrrole derivative represented by formula (1).

It has been known that pyrromethene metal complexes are particularly used for dopant to generate light with high luminance and that red emission is generated by introducing aromatic rings to the 1-, 3-, 5-, and 7-positions of the pyrromethene skeleton of the complex. However, the known pyrromethene compounds are liable to cause concentration quenching, and therefore cannot lead to sufficient red emission. Introducing a substituent to the 8-position of the pyrromethene skeleton decreases the concentration quenching because of the advantageous stereostructual and electronical effects of the substituent. On the other hand, if the substituent at the 8-position can rotate, the fluorescence quantum yield of the pyrromethene metal complex is degraded. In the present invention, by introducing an aryl group to the 8-position of the pyrromethene skeleton to prevent the rotation thereof, a high fluorescence quantum yield and degraded concentration quenching can be achieved. This prevention of the rotation is ensured by $Ar^1$ and $Ar^4$ of formula (1) and $Ar^6$ and $Ar^9$ of formula (2), which are aryl groups. The pyrromethene metal complexes of the present invention may be used as a host, but preferably, they are used as a dopant because they have a high fluorescence quantum yield and a small half band width of the emission spectrum.

Since excessive doping causes concentration quenching, 10 weight percent of dopant is, preferably, used for the host material. More preferably, 2 weight percent of the dopant is used for the host material. The dopant may be provided by codeposition with the host material. Alternatively, the dopant and the host material are mixed with each other and then are simultaneously deposited. The dopant may be contained in part of the host material or the entirety of the host material. The dopant may be laminated as a layer or be dispersed in the host material. Since even an extremely small amount of a pyrromethene metal complex can emit light, the pyrromethene metal complex may be disposed between host layers. The dopant applied to the LED material is not limited to only one of the above-described pyrromethene metal complexes, and a plurality of pyrromethene metal complexes may be mixed. Alternatively, a pyrromethene metal complex may be mixed with at a known dopant. Exemplary known dopants which can be mixed include naphthalimido derivatives such as bis(diisopropylphenyl) perylenetetracarboxylic imido; perynone derivatives; rare earth complexes such as Eu complexes of which the ligand is acetylacetone or benzoylacetone and phenanthroline; 4-(dicyanomethylene)-2-methyl-6-(p-dimethylaminostyryl)-4H-pyran and the analogues thereof; metal phthalocyanine derivatives such as magnesium phthalocyanine and aluminum chlorophthalocyanine; rhodamines; deazaflavin derivatives; coumarin derivatives; quinacridone derivatives; phenoxazines; and oxazines.

Exemplary host materials include the diketopyrrolo[3,4-c]pyrrole derivatives having the specific substituents; other pyrrolopyrrole derivatives; fused aromatic ring compounds such as anthracene and pyrene; metal-chelated oxynoid compounds such as tris(8-quinolinolato)aluminum; bisstyryl derivatives such as bisstyrylanthracene derivatives and distyrylbenzene derivatives; tetraphenylbutadienes; coumarin derivatives; oxadiazoles; pyrrolopyridines; perynone derivatives; cyclopentadienes; thiadiazolopyridines; and polymers such as polyphenylene vinylenes, polyparaphenylenes, and polythiophenes.

An electron transporting material needs to efficiently transport electrons injected from the cathode between the electrodes where an electric field is applied. Preferably, the electron transporting material has a high electron injection efficiency and efficiently transports the injected electrons. Hence, the electron transporting material, preferably, has a high electron affinity and electron mobility with thermal and electrochemical stability. Preferably, the electron transporting material produces few impurities when it is prepared and used. Exemplary electron transporting materials include quinolinol metal complexes such as 8-hydroxyquinoline aluminum, tropolone metal complexes, flavonol metal complexes, perylenes, perynones, naphthalenes, coumarin derivatives, oxadiazoles, aldazines, bisstyryl derivatives, pyrazines, oligopyridines such as bipyridine and terpyridine, phenanthrolines, quinolines, and aromatic phosphorus oxides. These materials may be used independently or be mixed or deposited with other electron transporting materials.

In order to more efficiently generate pure red emission, the recombination of holes with electrons must occur with high probability in the emissive layer, but not in the other layers. When a diketopyrrolo[3,4-c]pyrrole derivative is used for a emissive material, preferably, the ionization potential of the electron transporting material is 5.9 eV or more. The electron transporting material needs to be stable against power distribution for long hours in order to maintain a stable red emission over time. On this account, the electron transporting material, preferably, has a molecular weight of 400 or more, more preferably of 500 or more, and further more preferably of 600 or more. This is because many of the materials having a molecular weight less than 400 are easily affected by heat. In order to form a heat-resistant electron transporting layer, it is important to consider the glass-transition temperature of materials. A material having a higher glass-transition temperature results in a more stable amorphous layer. Preferably, the electron transporting material has a glass-transition temperature of 90° C. or more, more preferably of 110° C., and further more preferably of 150° C. As such an electron transporting material, organic compounds having a structure in which a plurality of skeletons are combined with each other having a conjugated bond, an aromatic hydrocarbon group, an aromatic heterocyclic group, or a combination of these groups therebetween are preferably used. The skeletons of the above-described derivatives can be directly used as the skeleton of the electron transporting material. Preferably, the skeleton has at least one quinoline ring or phosphorus oxide.

The hole-blocking layer prevents holes from moving without the recombination of holes injected from the anode with electrons injected from the cathode between the electrodes where an electric field is applied. The hole-blocking layer increases the provability of the recombination, depending on materials of layers, and thus improves the luminance efficiency of the LED. For the material of the hole-blocking layer, therefore, a substance is selected which has a lower energy level of the highest occupied molecular orbital than that of the hole transporting material and which rarely produce an exciplex with an adjacent layer. Since materials capable of transporting electrons can efficiently block holes, the above-described electron transporting materials are preferably used as a material of the hole-blocking layer.

The hole transporting layer, the emissive layer, the electron transporting layer, and the hole-blocking layer are formed by depositing the respective materials independently or by mixing at least two materials. Alternatively, the materials may be dispersed in a binding polymer including solvent soluble resins such as polyvinyl chloride, polycarbonate, polystyrene, poly(N-vinylcarbazole), polymethylmethacrylate, polybutylmethacrylate, polyester, polysulfone, polyphenylene oxide, polybutadiene, hydrocarbon resin, ketone resin, phenoxy resin, polysulfone, polyamide, ethyl cellulose, vinyl acetate, ABS resin, and polyurethane and hardening resins such as phenol resin, xylene resin, petroleum resin, urea resin, melamine, unsaturated polyester, alkyd resin, epoxide resin, and silicone resin.

The substances in the present invention is formed by resistance heating evaporation, electron beam evaporation, sputtering, molecular deposition, coating, or the like, and the method is not limited to these. Generally, resistance heating evaporation and electron beam evaporation are preferable in view of the performance of the LED. The thickness of the substance is set between 1 to 1000 nm depending on the resistance thereof.

Mainly direct current is used as electrical energy, and pulse current or alternating current may be used. It is preferable to set a current value and voltage as low as possible with respect to power consumption and the lifetime of the device.

The LED of the present invention may be used for matrix-type displays and segment-type displays. In a matrix system, pixels of a display are arrayed in a matrix, and images including characters are displayed by aggregating the pixels. Size and shapes of the pixels depend on use. For example, square pixels having a side length of 300 μm or less are used for displaying images and characters on personal computers, monitors, and TVs. Pixels having a side length of the order of millimeters are used for large-screen displays such as instruction panels. In the case of monochrome displays, single color pixels are arrayed. In the case of color displays, red, green, and blue pixels are arrayed in typically a stripe arrangement or a delta arrangement. Matrix-type displays may be driven by a line-sequential system or an active matrix system. While the line-sequential system has a simple structure, the active matrix system can have an advantage in driving performance. These driving systems are selected according to use.

In the segment system, a pixel pattern is formed so that predetermined information is displayed and thus light is emitted at predetermined areas. Exemplary segment-type displays include hour plates of digital clocks, temperature indicators, operation indicators of audiovisual apparatuses and electromagnetic cooking devices, and indicator panels of automobiles. The matrix system and the segment system may coexist in a display panel.

EXAMPLES

Examples and comparative examples of the present invention will now be described. The present invention is not limited to the following examples. Compound numbers shown in Examples each designate a compound represented by the above described formula of the same number. The structures of compounds were analyzed by the following.

$^1$H-NMR analysis was performed in a heavy chloroform solution with Superconductive FTNMR EX-270 produced by JEOL.

Elemental analysis was performed with CHN Corder MT-3 produced by Yanaco, with Ion Chromatography DX320 produced by Dionex, and Sequential ICP Emission Spectrochemical system SPS4000 produced by Seiko Instruments.

Mass spectrums were measured with Mass Spectrometer JMS-DX303 produced by JEOL.

Absorption spectra and fluorescence spectra were measured in $4 \times 10^{-6}$ mol/L of dichloromethane with Spectrophotometer U-3200 produced by Hitachi and Spectrofluorometer F-2500 produced by Hitachi, respectively.

Example 1
Synthesis of Compound [1]

In 30 mL of 1,2-dichloroethane, 1.3 g of 2-benzoyl-3,5-bis(4-n-hexylphenyl)pyrrole, 1 g of 2,4-bis(4-n-hexylphenyl)pyrrole, and 0.47 mL of phosphorous oxychloride were reacted with one another under reflux for 12 hours. After cooling, 3.6 mL of diisopropylethylamine and 2.6 mL of boron trifluoride diethylether complex were added and stirred for 6 hours. After 50 mL of water was added, extraction was performed with dichloromethane. The extract was concentrated and refined through a column chromatography with silica gel and thus results in 1 g of purplish red powder. The following is the results of $^1$H-NMR analysis.

$^1$H-NMR (CDCl$_3$ (δ=ppm)): 0.90(t, 12H), 1.29–1.65(m, 32H), 2.39(t, 4H), 2.64(t, 4H), 6.44(t, 2H), 6.49(s, 2H), 6.60–6.63(m, 9H), 6.83(d. 2H), 7.25(d, 4H), 7.82(d, 4H).

Elemental analysis was performed on the assumption that the composition formula of the powder was $C_{63}H_{75}N_2F_2B$. The results are as follows. Values in parentheses are theoretical values.

C: 83.5% (83.2%), H: 8.4% (8.3%), N: 3.2% (3.1%), F: 3.2% (4.2%), B: 1.2% (1.2%).

According to mass spectrometry, the main molecular ion peak of the object was m/Z=908. Thus, the resulting purplish red powder was identified as Compound [1]. This Compound [1] exhibited the following photophysical properties.

Absorption spectrum: λmax 568 nm (solvent: dichloromethane)

Fluorescence spectrum: λmax 613 nm (solvent: dichloromethane)

An LED using Compound [1] was prepared. An ITO transparent conductive layer deposited on a glass substrate, having a thickness of 150 nm (produced by electron beam evaporation by Asahi Glass, 15 Ω/□) was cut into 30 mm×40 mm and then was subjected to etching. This ITO plate was subjected to ultrasonic cleanings successively using acetone and plate cleaner Semicoclean 56 (produced by Furuuchi Chemical) for 15 minutes each, and then rinsed with ultrapure water. Subsequently, the ITO plate is subjected to ultrasonic cleaning in isopropyl alcohol for 15 minutes, then immersed in hot methanol for 15 minutes, and was followed by drying. The ITO plate was subjected to a UV-ozone treatment for one hour on the eve of the process of manufacturing the LED. Then, the ITO plate was placed in a vacuum vapor deposition apparatus and the apparatus was evacuated to a pressure of $5 \times 10^{-5}$ Pa or below. On the ITO plate, 4,4'-bis(N-(m-tolyl)-N-phenylamino)biphenyl was deposited to a thickness of 50 nm to form a hole transporting layer by vacuum evaporation. Next, 1,4-diketo-2,5-bis(3,5-dimethylbenzyl)-3,6-bis(4-methylphenyl)pyrrolo[3,4-c]pyrrole as a host material and Compound [1] as a dopant are simultaneously deposited so as to form a layer having a thickness of 15 nm and a dopant content of 1 weight percent, and the host material was further deposited so as to have a thickness of 35 nm. Next, 0.5 nm in thickness of lithium and 150 nm in thickness of silver were deposited to form the cathode. Thus, an LED of 5 mm×5 mm was completed. The thicknesses described above were measured by a quartz crystal oscillator thickness meter. The resulting LED generated a red emission having a peak wavelength of 618 nm and a luminance efficiency of 4.2 cd/A.

Example 2
Synthesis of Compound [2]

In the same procedure as in Compound [1], 1.2 g of 2-benzoyl-3,5-diphenylpyrrole were reacted with 0.8 g of 2,4-diphenylpyrrole to produce 1.4 g of red powder. The results of $^1$H-NMR analysis is as follows.

$^1$H-NMR(CDCl$_3$ (δ=ppm)): 6.46(t, 2H), 6.25(s, 2H), 6.67–6.88(m, 11H), 7.43(m, 6H), 7.90(d. 4H).

Elemental analysis was performed on the assumption that the composition formula of the powder was $C_{39}H_{27}N_2F_2B$. The results are as follows. Values in parentheses are theoretical values.

C: 82.3% (81.8%), H: 4.8% (4.7%), N: 4.9% (4.9%), F: 6.6% (6.6%), B: 1.9% (2.0%).

According to mass spectrometry, the main molecular ion peak of the object was m/Z=572. Thus, the resulting red powder was identified as Compound [2]. This Compound [2] exhibited the following photophysical properties.

Absorption spectrum: λmax 556 nm (solvent: dichloromethane)

Fluorescence spectrum: λmax 600 nm (solvent: dichloromethane)

An LED using Compound [2] as a dopant was prepared in exactly the same procedure as in Example 1 other than the dopant used. This resulting LED generated a vermilion emission having a peak wavelength of 608 nm and a luminance efficiency of 2.6 cd/A.

Example 3
Synthesis of Compound [3]

In the same procedure as in Compound [1], 0.4 g of 2-(2-methylbenzoyl)-3,5-bis(4-n-hexylphenyl)pyrrole were reacted with 0.25 g of 2,4-bis(4-n-hexylphenyl)pyrrole to produce 0.1 g of purplish red powder. The results of $^1$H-NMR analysis are as follows.

$^1$H-NMR(CDCl$_3$ (δ=ppm)): 0.88(t, 12H), 1.29–1.67(m, 32H), 2.39(t, 4H), 2.63(t, 4H), 3.51(s, 3H), 6.00(d, 2H), 6.51(s, 2H), 6.63–6.73(m, 10H), 7.23(d, 4H), 7.81(d, 4H).

Elemental analysis was performed on the assumption that the composition formula of the powder was $C_{64}H_{77}N_2F_2B$. The results are as follows. Values in parentheses are theoretical values.

C: 83.3% (83.3%), H: 8.4% (8.4%), N: 3.1% (3.0%), F: 3.2% (4.1%), B: 1.2% (1.2%).

According to mass spectrometry, the main molecular ion peak of the object was m/Z=922. Thus, the resulting purplish red powder was identified as Compound [3]. This Compound [3] exhibited the following photophysical properties.

Absorption spectrum: λmax 568 nm (solvent: dichloromethane)

Fluorescence spectrum: λmax 613 nm (solvent: dichloromethane)

An LED using Compound [3] as a dopant was prepared in exactly the same procedure as in Example 1 other than the dopant used. This resulting LED generated a red emission having a peak wavelength of 618 nm and a luminance efficiency of 4.0 cd/A.

Example 4

Synthesis of Compound [4]

In the same procedure as in Compound [1], 0.5 g of 2-(4-phenylbenzoyl)-3,5-bis(4-n-hexylphenyl)pyrrole were reacted with 0.25 g of 2,4-bis(4-n-hexylphenyl)pyrrole to produce 0.18 g of purplish red powder. The results of $^1$H-NMR analysis are as follows.

$^1$H-NMR(CDCl$_3$ (δ=ppm)): 0.84(t, 12H), 1.07–1.65(m, 32H), 2.25(t, 4H), 2.64(t, 4H), 6.53(s, 2H), 6.61–6.69(m, 11H), 6.88(d, 2H), 7.23(d, 4H), 7.24–7.37(m, 5H), 7.83(d, 4H).

Elemental analysis was performed on the assumption that the composition formula of the powder was $C_{69}H_{79}N_2F_2B$. The results are as follows. Values in parentheses are theoretical values.

C: 84.3% (84.1%), H: 8.1% (8.0%), N: 2.9% (2.8%), F: 3.0% (3.9%), B: 1.2% (1.2%).

According to mass spectrometry, the main molecular ion peak of the object was m/Z=984. Thus, the resulting purplish red powder was identified as Compound [4]. This Compound [4] exhibited the following photophysical properties.

Absorption spectrum: λmax 569 nm (solvent: dichloromethane)

Fluorescence spectrum: λmax 615 nm (solvent: dichloromethane)

An LED using Compound [4] as a dopant was prepared in exactly the same procedure as in Example 1 other than the dopant used. This resulting LED generated a red emission having a peak wavelength of 618 nm and a luminance efficiency of 3.8 cd/A.

Example 5

Synthesis of Compound [5]

In the same procedure as in Compound [1], 0.45 g of 2-(4-methoxybenzoyl)-3,5-bis(4-n-hexylphenyl)pyrrole were reacted with 0.25 g of 2,4-bis(4-n-hexylphenyl)pyrrole to produce 0.15 g of purplish red powder. The results of $^1$H-NMR analysis are as follows.

$^1$H-NMR(CDCl$_3$ (δ=ppm)): 0.91(t, 12H), 1.28–1.67(m, 32H), 2.00(s, 3H), 2.38(t, 4H), 2.63(t, 4H), 6.21(d, 1H), 6.43(s, 2H), 6.46(d, 2H), 6.63(m, 8H), 6.80(d, 1H), 7.25(d, 4H), 7.82 (d, 4H).

Elemental analysis was performed on the assumption that the composition formula of the powder was $C_{64}H_{77}N_2OF_2B$. The results are as follows. Values in parentheses are theoretical values.

C: 82.1% (81.9%), H: 8.3% (8.2%), N: 3.1% (3.0%), O: 1.8% (1.7%), F: 3.0% (4.0%), B: 1.2% (1.2%).

According to mass spectrometry, the main molecular ion peak of the object was m/Z=938. Thus, the resulting purplish red powder was identified as Compound [5]. This Compound [5] exhibited the following photophysical properties.

Absorption spectrum: λmax 566 nm (solvent: dichloromethane)

Fluorescence spectrum: λmax 611 nm (solvent: dichloromethane)

An LED using Compound [5] as a dopant was prepared in exactly the same procedure as in Example 1 other than the dopant used. This resulting LED generated a red emission having a peak wavelength of 615 nm and a luminance efficiency of 4.0 cd/A.

Example 6

Synthesis of Compound [6]

In the same procedure as in Compound [1], 0.4 g of 2-(4-cyanobenzoyl)-3,5-bis(4-n-hexylphenyl)pyrrole were reacted with 0.25 g of 2,4-bis(4-n-hexylphenyl)pyrrole to produce 0.3 g of auburn powder. The results of $^1$H-NMR analysis are as follows.

$^1$H-NMR(CDCl$_3$ (δ=ppm)): 0.91(t, 12H), 1.33–1.65(m, 32H), 2.44(t, 4H), 2.64(t, 4H), 6.52(s, 2H), 6.59(d, 2H), 6.70–6.75(m, 8H), 6.93(d, 2H), 7.25(d, 4H), 7.83(d, 4H).

Elemental analysis was performed on the assumption that the composition formula of the powder was $C_{64}H_{74}N_3F_2B$. The results are as follows. Values in parentheses are theoretical values.

C: 82.6% (82.3%), H: 7.9% (7.9%), N: 4.6% (4.5%), F: 3.3% (4.1%), B: 1.2% (1.2%).

According to mass spectrometry, the main molecular ion peak of the object was m/Z=933. Thus, the resulting auburn powder was identified as Compound [6]. This Compound [6] exhibited the following photophysical properties.

Absorption spectrum: λmax 576 nm (solvent: dichloromethane)

Fluorescence spectrum: λmax 626 nm (solvent: dichloromethane)

Example 7

Synthesis of Compound [7]

In the same procedure as in Compound [1], 0.5 g of 2-(1-naphthoyl)-3,5-bis(4-n-hexylphenyl)pyrrole were reacted with 0.25 g of 2,4-bis(4-n-hexylphenyl)pyrrole to produce 0.2 g of purple powder. The results of $^1$H-NMR analysis are as follows.

$^1$H-NMR(CDCl$_3$ (δ=ppm)): 0.93(t, 12H), 1.25–1.65(m, 32H), 2.21(t, 4H), 2.64(t, 4H), 6.27(m, 8H), 6.40(s, 2H), 6.64(t, 1H), 7.00(dd, 2H), 7.24(d, 4H), 7.24–7.34(m, 3H), 7.80–7.87(m, 5H).

Elemental analysis was performed on the assumption that the composition formula of the powder was $C_{67}H_{77}N_2F_2B$. The results are as follows. Values in parentheses are theoretical values.

C: 84.3% (83.9%), H: 8.1% (8.0%), N: 2.9% (2.9%), F: 3.1% (4.0%), B: 1.1% (1.2%).

According to mass spectrometry, the main molecular ion peak of the object was m/Z=958. Thus, the resulting purple powder was identified as Compound [7]. This Compound [7] exhibited the following photophysical properties.

Absorption spectrum: λmax 571 nm (solvent: dichloromethane)

Fluorescence spectrum: λmax 616 nm (solvent: dichloromethane)

An LED using Compound [7] as a dopant was prepared in exactly the same procedure as in Example 1 other than the dopant used. This resulting LED generated a red emission having a peak wavelength of 619 nm and a luminance efficiency of 4.2 cd/A.

Example 8

Synthesis of Compound [8]

In the same procedure as in Compound [1], 0.4 g of 2-benzoyl-3,5-bis(4-methoxyphenyl)pyrrole were reacted with 0.25 g of 2,4-bis(4-methoxyphenyl)pyrrole to produce 0.2 g of blue-purple powder. The results of $^1$H-NMR analysis are as follows.

¹H-NMR(CDCl₃ (δ=ppm)): 3.67(s, 3H), 3.86(s, 3H), 6.38 (d, 2H), 6.47(s, 2H), 6.54(t, 2H), 6.64–6.75(m, 5H), 6.85(d, 2H), 6.96(d, 4H), 7.89(d, 4H).

Elemental analysis was performed on the assumption that the composition formula of the powder was $C_{43}H_{35}N_2O_4F_2B$. The results are as follows. Values in parentheses are theoretical values.

C: 75.0% (74.6%), H: 5.2% (5.1%), N: 4.2% (4.0%), O: 9.3% (9.2%), F: 4.4% (5.5%), B: 1.6% (1.6%).

According to mass spectrometry, the main molecular ion peak of the object was m/Z=692. Thus, the resulting blue-purple powder was identified as Compound [8]. This Compound [8] exhibited the following photophysical properties.

Absorption spectrum: λmax 584 nm (solvent: dichloromethane)

Fluorescence spectrum: λmax 632 nm (solvent: dichloromethane)

An LED using Compound [8] as a dopant was prepared in exactly the same procedure as in Example 1 other than the dopant used. This resulting LED generated a red emission having a peak wavelength of 641 nm and a luminance efficiency of 2.7 cd/A.

Example 9

Synthesis of Compound [9]

In the same procedure as in Compound [1], 0.35 g of 2-benzoyl-3,5-bis(4-n-amyloxyphenyl)pyrrole were reacted with 0.25 g of 2,4-bis(4-n-amyloxyphenyl)pyrrole to produce 0.1 g of blue-purple powder. The results of ¹H-NMR analysis are as follows.

¹H-NMR(CDCl₃ (δ=ppm)): 0.94(t, 12H), 1.38–1.41(m, 16H), 1.68–1.83(m, 8H), 3.80(t, 4H), 4.00(t, 4H), 6.36(d, 2H), 6.46(s, 2H), 6.53(t, 2H), 6.62–6.73(m, 5H), 6.85(d, 2H), 6.94(d, 4H), 7.86(d, 4H).

Elemental analysis was performed on the assumption that the composition formula of the powder was $C_{59}H_{67}N_2O_4F_2B$. The results are as follows. Values in parentheses are theoretical values.

C: 77.5% (77.3%), H: 7.5% (7.5%), N: 3.2% (3.1%), O: 7.1% (7.0%), F: 3.1% (4.1%), B: 1.2% (1.2%).

According to mass spectrometry, the main molecular ion peak of the object was m/Z=916. Thus, the resulting blue-purple powder was identified as Compound [9]. This Compound [9] exhibited the following photophysical properties.

Absorption spectrum: λmax 587 nm (solvent: dichloromethane)

Fluorescence spectrum: λmax 636 nm (solvent: dichloromethane)

Example 10

Synthesis of Compound [10]

In the same procedure as in Compound [1], 0.6 g of 2-(1-naphtoyl)-3,5-bis(4-methylphenyl)pyrrole were reacted with 0.25 g of 2,4-bis(4-methylphenyl)pyrrole to produce 0.55 g of purple powder. The results of ¹H-NMR analysis are as follows.

¹H-NMR (CDCl₃ (δ=ppm)): 2.00(s, 6H), 2.40(s, 6H), 6.26(m, 8H), 6.39(s, 2H), 6.65(t, 1H), 7.00(d, 1H), 7.12(d, 1H), 7.24(d, 4H), 7.24–7.33(m, 3H), 7.77–7.86(m, 5H).

Elemental analysis was performed on the assumption that the composition formula of the powder was $C_{47}H_{37}N_2F_2B$. The results are as follows. Values in parentheses are theoretical values.

C: 83.5% (83.2%), H: 5.6% (5.5%), N: 4.3% (4.1%), F: 4.8% (5.6%), B: 1.5% (1.6%).

According to mass spectrometry, the main molecular ion peak of the object was m/Z=678. Thus, the resulting purple powder was identified as Compound [10]. This Compound [10] exhibited the following photophysical properties.

Absorption spectrum: λmax 575 nm (solvent: dichloromethane)

Fluorescence spectrum: λmax 613 nm (solvent: dichloromethane)

An LED using Compound [10] as a dopant was prepared in exactly the same procedure as in Example 1 other than the dopant used. This resulting LED generated a red emission having a peak wavelength of 620 nm and a luminance efficiency of 3.0 cd/A.

Example 11

Synthesis of Compound [11]

In the same procedure as in Compound [1], 0.35 g of 2-benzoyl-3,5-bis(4-(2,4-dimethylphenyl)phenyl) pyrrole were reacted with 0.25 g of 2,4-bis(4-(2,4-dimethylphenyl) phenyl)pyrrole to produce 0.15 g of purple powder. The results of ¹H-NMR analysis are as follows.

¹H-NMR (CDCl₃ (δ=ppm)): 2.18(s, 6H), 2.32(s, 6H), 2.36(ss, 12H), 6.67(s, 2H), 6.81(d, 8H), 6.94–7.07(m, 11H), 7.11(d, 2H), 7.43(d, 4H), 8.01(d, 4H).

Elemental analysis was performed on the assumption that the composition formula of the powder was $C_{71}H_{59}N_2F_2B$. The results are as follows. Values in parentheses are theoretical values.

C: 86.4% (86.2%), H: 6.0% (6.0%), N: 2.9% (2.8%), F: 3.0% (3.9%), B: 1.2% (1.1%).

According to mass spectrometry, the main molecular ion peak of the object was m/Z=988. Thus, the resulting purple powder was identified as Compound [11]. This Compound [11] exhibited the following photophysical properties.

Absorption spectrum: λmax 576 nm (solvent: dichloromethane)

Fluorescence spectrum: λmax 626 nm (solvent: dichloromethane)

Example 12

Synthesis of Compound [12]

In the same procedure as in Compound [1], 0.4 g of 2-(1-naphtoyl)-3,5-bis(4-methylphenyl)pyrrole were reacted with 0.25 g of 2,4-bis(4-methoxyphenyl)pyrrole to produce 0.1 g of purple powder. The results of ¹H-NMR analysis are as follows.

¹H-NMR (CDCl₃ (δ=ppm)): 1.97(s, 3H), 2.40(s, 3H), 3.54(s, 3H), 3.86(s, 3H), 5.99(d, 2H), 6.25(s, 4H), 6.30–6.39 (m, 8H), 6.69(t, 1H), 6.97(d, 3H), 7.14(d, 1H), 7.26(d, 2H), 7.26–7.37(m, 3H), 7.78–7.95(m, 5H).

Elemental analysis was performed on the assumption that the composition formula of the powder was $C_{47}H_{37}N_2O_2F_2B$. The results are as follows. Values in parentheses are theoretical values.

C: 79.6% (79.4%), H: 5.1% (5.2%), N: 4.0% (3.9%), O: 4.6% (4.5%), F: 4.6% (5.4%), B: 1.6% (1.6%).

According to mass spectrometry, the main molecular ion peak of the object was m/Z=710. Thus, the resulting purple powder was identified as Compound [12]. This Compound [12] exhibited the following photophysical properties.

Absorption spectrum: λmax 577 nm (solvent: dichloromethane)

Fluorescence spectrum: λmax 624 nm (solvent: dichloromethane)

An LED using Compound [12] as a dopant was prepared in exactly the same procedure as in Example 1 other than the dopant used. This resulting LED generated a red emission having a peak wavelength of 628 nm and a luminance efficiency of 2.9 cd/A.

Example 13

Synthesis of Compound [53]

In the same procedure as in Compound [1], 0.4 g of 2-benzoyl-3,5-bis(4-n-butylphenyl)pyrrole were reacted with 0.25 g of 2,4-bis(4-n-butylphenyl)pyrrole to produce 0.27 g of red powder. The results of $^1$H-NMR analysis are as follows.

$^1$H-NMR (CDCl$_3$ (δ=ppm)): 1.97(s, 3H), 2.40(s, 3H), 3.54(s, 3H), 3.86(s, 3H), 5.99(d, 2H), 6.25(s, 4H), 6.30–6.39 (m, 8H), 6.69(t, 1H), 6.97(d, 3H), 7.14(d, 1H), 7.26(d, 2H), 7.26–7.37 (m, 3H), 7.78–7.95 (m, 5H).

Elemental analysis was performed on the assumption that the composition formula of the powder was $C_{55}H_{59}N_2F_2B$. The results are as follows. Values in parentheses are theoretical values.

C: 83.1% (82.9%), H: 7.5% (7.4%), N: 3.6% (3.5%), F: 4.0% (4.8%), B: 1.3% (1.4%).

According to mass spectrometry, the main molecular ion peak of the object was m/Z=796. Thus, the resulting red powder was identified as Compound [53]. This Compound [53] exhibited the following photophysical properties.

Absorption spectrum: λmax 569 nm (solvent: dichloromethane)

Fluorescence spectrum: λmax 611 nm (solvent: dichloromethane)

An LED using Compound [53] as a dopant was prepared in exactly the same procedure as in Example 1 other than the dopant used. This resulting LED generated a red emission having a peak wavelength of 617 nm and a luminance efficiency of 5.0 cd/A.

Example 14

Synthesis of Compound [59]

In 30 mL of absolute tetrahydrofuran, 0.5 g of compound [10] was dissolved. Subsequently, 1.88 mL of phenylmagnesium bromide (1.0 mol/L in tetrahydrofuran) was dropped into the tetrahydrofuran solution at 20° C. and then was reacted at 60° C. for 9 hours. After cooling, 50 mL of water was added and then extraction was performed with dichloromethane. The extract was concentrated and refined through a column chromatography with silica gel and thus results in 0.32 g of purplish red powder. The following is the results of $^1$H-NMR analysis.

$^1$H-NMR (CDCl$_3$ (δ=ppm)): 1.97(s, 3H), 2.40(s, 3H), 3.54(s, 3H), 3.86(s, 3H), 5.99(d, 2H), 6.25(s, 4H), 6.30–6.39 (m, 8H), 6.69(t, 1H), 6.97(d, 3H), 7.14(d, 1H), 7.26(d, 2H), 7.26–7.37(m, 3H), 7.78–7.95(m, 5H).

Elemental analysis was performed on the assumption that the composition formula of the powder was $C_{59}H_{47}N_2B$. The results are as follows. Values in parentheses are theoretical values.

C: 89.3% (89.2%), H: 6.0% (5.9%), N: 3.5% (3.5%), B: 1.2% (1.4%).

According to mass spectrometry, the main molecular ion peak of the object was m/Z=794. Thus, the resulting purplish red powder was identified as Compound [59]. This Compound [59] exhibited the following photophysical properties.

Absorption spectrum: λmax 568 nm (solvent: dichloromethane)

Fluorescence spectrum: λmax 613 nm (solvent: dichloromethane)

An LED using Compound [59] as a dopant was prepared in exactly the same procedure as in Example 1 other than the dopant used. This resulting LED generated a red emission having a peak wavelength of 616 nm and a luminance efficiency of 3.8 cd/A.

Example 15

For preparing an LED, the same procedure was taken until the hole transporting layer was deposited, and then the compound [53] was deposited to a thickness of 50 nm. Next, 0.5 nm in thickness of lithium and 150 nm in thickness of silver were successively deposited to form the cathode. Thus, an LED of 5 mm×5 mm was completed. This resulting LED generated a red emission having a peak wavelength of 622 nm and a luminance efficiency of 2.5 cd/A.

Example 16

An LED using Compound [63] as a dopant was prepared in exactly the same procedure as in Example 1 other than the dopant used. This resulting LED generated a red emission having a peak wavelength of 609 nm and a luminance efficiency of 1.6 cd/A.

Example 17

An LED using Compound [85] as dopant was prepared in exactly the same procedure as in Example 1 other than the dopant used. This resulting LED generated a red emission having a peak wavelength of 628 nm and a luminance efficiency of 1.1 cd/A.

Example 18

For preparing an LED, the same procedure as in Example 1 was taken until the hole transporting layer was deposited. Then, 1,4-diketo-2,5-bis(3,5-dimethylbenzyl)-3,6-bis(4-methylphenyl)pyrrolo[3,4-c]pyrrole as a host material and 9-diethylamino-5H-benzo(a)phenoxazine-5-one (the fluorescent peak wavelength was 610 nm in dichloromethane) as a dopant were simultaneously deposited so as to form a emissive layer having a thickness of 25 nm and a dopant content of 0.5 weight percent. Next, 2,9-dimethyl-4,7-diphenyl-1,10-phenanthroline (BCP) was deposited to form the electron transporting layer having a thickness of 25 nm. Finally, 0.5 nm in thickness of lithium and 150 nm in thickness of silver were deposited to form the cathode and thus an LED of 5 mm×5 mm was completed. This resulting LED generated a red emission having an emission peak wavelength of 609 nm and a spectrum half band width of 71 nm depending on the dopant. The red emission exhibited a luminance of 3000 cd/m$^2$ under an applied voltage of 16 V.

Examples 19 to 25 and 28 to 29 and Comparative Example 1

LEDs were prepared in the same procedure as in Example 18 except that compounds shown in Table 1 were used as a hole transporting material, a host material, dopant, and a cathode material. The results are shown in Table 1. HTM1 used in Example 25 is the following compound:

TABLE 1

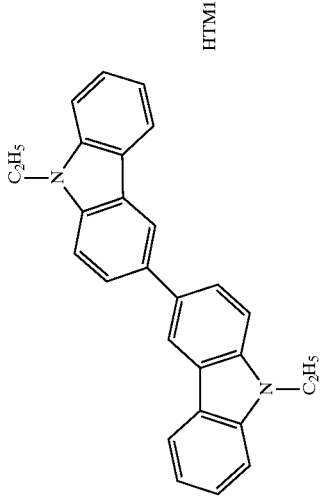

HTM1

| | emissive layer | | | | | | | | |
|---|---|---|---|---|---|---|---|---|---|
| | Hole transporting layer | Host material | Dopant | Fluorescent peak wavelength in CH2Cl2 (nm) | Electron transporting layer | Cathode | Emission peak wavelength (nm) | Spectrum half band width (nm) | applied voltage (V) | Luminance (cd/m²) |
| Example 18 | 4,4'-bis(N-(m-tolyl)-N-phenylamino)biphenyl | 1,4-diketo-2,5-bis(3,5-dimethylbenzyl)-3,6-bis(4-methylphenyl)pyrrolo[3,4-c]pyrrole | 9-diethylamino-5H-benzo(a)phenoxazine-5-one | 610 | BCP | Li 0.5 nm Ag 150 nm | 609 | 71 | 16 | 3000 |
| Example 19 | 4,4'-bis(N-(m-tolyl)-N-phenylamino)biphenyl | 1,4-diketo-2,5-bis(3,5-dimethylbenzyl)-3,6-bis(4-methylphenyl)pyrrolo[3,4-c]pyrrole | 3-ethyl-2-[3-(3-ethyl-2-benzothiazolinylidene)-1-propenyl]benzothiazolium iodide | 596 | BCP | Li 0.5 nm Ag 150 nm | 602 | 45 | 16 | 1200 |
| Example 20 | 4,4'-bis(N-(m-tolyl)-N-phenylamino)biphenyl | 1,4-diketo-2,5-bis(3,5-dimethylbenzyl)-3,6-bis(4-methylphenyl)pyrrolo[3,4-c]pyrrole | 4-(dicyanomethylene)-2-methyl-6-(1,1,7,7-tetramethyljulolidyl-9-enyl)-4H-pyran | 625 | BCP | Li 0.5 nm Ag 150 nm | 609 | 88 | 16 | 1500 |
| Example 21 | 4,4'-bis(N-(m-tolyl)-N-phenylamino)biphenyl | 1,4-diketo-2,5-bis(3,5-dimethylbenzyl)-3,6-bis(4-methylphenyl)pyrrolo[3,4-c]pyrrole | Compound [99] | 629 | BCP | Li 0.5 nm Ag 150 nm | 636 | 33 | 12 | 10000 |
| Example 22 | 4,4'-bis(N-(m-tolyl)-N-phenylamino)biphenyl | 1,4-diketo-2,5-bis(3,5-dimethylbenzyl)-3,6-bis(4-methylphenyl)pyrrolo[3,4-c]pyrrole | Compound [63] | 605 | BCP | Li 0.5 nm Ag 150 nm | 617 | 42 | 16 | 3000 |
| Comparative Example 1 | 4,4'-bis(N-(m-tolyl)-N-phenylamino)biphenyl | 1,4-diketo-2,5-dimethyl-3,6-diphenylpirrolo[3,4-c]pyrrole | Compound [63] | 605 | BCP | Li 0.5 nm Ag 150 nm | 609 | 52 | 16 | 900 |
| Example 23 | 4,4'-bis(N-(m-tolyl)-N-phenylamino)biphenyl | 1,4-diketo-2,5-bis(3,5-dimethylbenzyl)-3,6-bis(4-methylphenyl)pyrrolo[3,4-c]pyrrole | Compound [66] | 625 | BCP | Li 0.5 nm Ag 150 nm | 632 | 40 | 19 | 3200 |
| Example 24 | 4,4'-bis(N-(m-tolyl)-N-phenylamino)biphenyl | 1,4-diketo-2,5-bis(3,5-dimethylbenzyl)-3,6-bis(4-methylphenyl)pyrrolo[3,4-c]pyrrole | Compound [65] | 606 | BCP | Li 0.5 nm | 612 | 40 | 17 | 4200 |

TABLE 1-continued

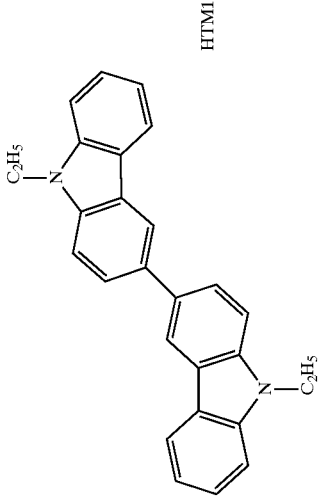

HTM1

| | | emissive layer | | | | | | | |
|---|---|---|---|---|---|---|---|---|---|
| | Hole transporting layer | Host material | Dopant | Fluorescent peak wavelength in CH2Cl2 (nm) | Electron transporting layer | Cathode | Emission peak wavelength (nm) | Spectrum half band width (nm) | applied voltage (V) | Luminance (cd/m²) |
| | phenylamino)biphenyl | dimethylbenzyl)-3,6-bis(4-methylphenyl)pyrrolo[3,4-c]pyrrole | | | | Ag 150 nm | | | | |
| Example 25 | HTM1 | 1,4-diketo-2,5-bis(3,5-dimethylbenzyl)-3,6-bis(4-methylphenyl)pyrrolo[3,4-c]pyrrole | Compound[65] | 606 | BCP | Li 0.5 nm Ag 150 nm | | | | |
| Example 28 | 4,4'-bis(N-(m-tolyl)-N-phenylamino)biphenyl | 1,4-diketo-2,5-bis(3,5-dimethylbenzyl)-3,6-bis(4-methylphenyl)pyrrolo[3,4-c]pyrrole | Compound[73] | 630 | BCP | Li 0.5 nm Ag 150 nm | 629 | 38 | 15 | 3600 |
| Example 29 | 4,4'-bis(N-(m-tolyl)-N-phenylamino)biphenyl | 1,4-diketo-2,5-bis(3,5-dimethylbenzyl)-3,6-bis(4-methylphenyl)pyrrolo[3,4-c]pyrrole | Compound[69] | 641 | BCP | Li 0.5 nm Ag 150 nm | 645 | 32 | 17 | 2900 |

Example 26

An LED was prepared in the same procedure as in Example 24 except that 10 nm in thickness of copper phthalocyanine (CuPc) as a first hole transporting layer and HTM1 as a second hole transporting layer were successively deposited. This resulting LED generated a red emission having an emission peak wavelength of 612 nm and a spectrum half band width of 40 nm according to the compound [65]. The red emission exhibited a luminance of 6400 cd/m$^2$ under an applied voltage of 14 V.

Example 27

For preparing an LED, the compound [100], which has a fluorescent peak wavelength of 619 nm in dichloromethane solution, was used as a dopant to form the emissive layer. Subsequently, 20 nm in thickness of the host material used in the emissive layer and 5 nm in thickness of BCP were successively used to form the electron transporting layer. Aluminum was used for the cathode instead of silver. Other processes were the same as in Example 18. This resulting LED generated a red emission having an emission peak wavelength of 629 nm and a spectrum half band width of 28 nm according to the compound [100]. The red emission exhibited a luminance of 7500 cd/m$^2$ under an applied voltage of 14 V.

Examples 30 to 47

LEDs were prepared in the same procedure as in Example 27 except that compounds shown in Tables 2 and 3 were used as a hole transporting material, a host material, and a dopant. The results are shown in Tables 2 and 3.

TABLE 2

| | Hole transporting layer | Host material | Dopant | Fluorescent peak wavelength in CH2Cl2 (nm) |
|---|---|---|---|---|
| Example 27 | 4,4'-bis(N-(m-tolyl)-N-phenylamino)biphenyl | 1,4-diketo-2,5-bis(3,5-dimethylbenzyl)-3,6-bis(4-methylphenyl)pyrrolo[3,4-c]pyrrole | Compound [100] | 619 |
| Example 30 | 4,4'-bis(N-(m-tolyl)-N-phenylamino)biphenyl | 1,4-diketo-2,5-bis(3,5-dimethylbenzyl)-3,6-bis(4-methylphenyl)pyrrolo[3,4-c]pyrrole | Compound [86] | 617 |
| Example 31 | 4,4'-bis(N-(m-tolyl)-N-phenylamino)biphenyl | 1,4-diketo-2,5-bis(3-methylbenzyl)-3,6-bis(4-biphenyl)pyrrolo[3,4-c]pyrrole | Compound [99] | 629 |
| Example 32 | 4,4'-bis(N-(m-tolyl)-N-phenylamino)biphenyl | 1,4-diketo-2,5-bis(3-methylbenzyl)-3,6-bis(4-biphenyl)pyrrolo[3,4-c]pyrrole | Compound [100] | 619 |
| Example 33 | 4,4'-bis(N-(m-tolyl)-N-phenylamino)biphenyl | 1,4-diketo-2,5-bis(2-methylbenzyl)-3,6-bis(2-naphthyl)pyrrolo[3,4-c]pyrrole | Compound [99] | 629 |
| Example 34 | 4,4'-bis(N-(m-tolyl)-N-phenylamino)biphenyl | 1,4-diketo-2,5-bis(3,5-dimethylbenzyl)-3,6-bis(2-(6-methoxynaphthyl))pyrrolo[3,4-c]pyrrole | Compound [99] | 629 |
| Example 35 | 4,4'-bis(N-(m-tolyl)-N-phenylamino)biphenyl | 1,4-diketo-2,5-bis(3,5-di-tert-butylbenzyl)-3,6-bis(2-naphthyl)pyrrolo[3,4-c]pyrrole | Compound [99] | 629 |
| Example 36 | 4,4'-bis(N-(m-tolyl)-N-phenylamino)biphenyl | 1,4-diketo-2,5-bis(3,5-di-tert-butylbenzyl)-3,6-bis(4-methylphenyl)pyrrol[3,4-c]pyrrole | Compound [99] | 629 |
| Example 37 | 4,4'-bis(N-(m-tolyl)-N-phenylamino)biphenyl | 1,4-diketo-2,5-bis(3,5-di-tert-butylbenzyl)-3,6-bis(4-methylphenyl)pyrrolo[3,4-c]pyrrole | Compound [86] | 617 |

| | Electron transporting layer | Cathode | Emission peak wavelength (nm) | Spectrum half band width (nm) | applied voltage (V) | Luminance (cd/m$^2$) |
|---|---|---|---|---|---|---|
| Example 27 | Host material 20 nm | BCP 5 nm | Li 0.5 nm Al 150 nm | 629 | 28 | 14 | 7500 |
| Example 30 | Host material 20 nm | BCP 5 nm | Li 0.5 nm Al 150 nm | 628 | 43 | 13 | 9500 |
| Example 31 | Host material 20 nm | BCP 5 nm | Li 0.5 nm Al 150 nm | 639 | 28 | 14 | 1700 |
| Example 32 | Host material 20 nm | BCP 5 nm | Li 0.5 nm Al 150 nm | 633 | 28 | 13 | 5300 |
| Example 33 | Host material 20 nm | BCP 5 nm | Li 0.5 nm Al 150 nm | 642 | 33 | 14 | 2700 |
| Example 34 | Host material 20 nm | BCP 5 nm | Li 0.5 nm Al 150 nm | 637 | 33 | 14 | 1000 |
| Example 35 | Host material 20 nm | BCP 5 nm | Li 0.5 nm Al 150 nm | 637 | 33 | 16 | 3500 |
| Example 36 | Host material 20 nm | BCP 5 nm | Li 0.5 nm Al 150 nm | 631 | 33 | 15 | 3100 |

TABLE 2-continued

| | | | | | | | |
|---|---|---|---|---|---|---|---|
| Example 37 | Host material 20 nm | BCP 5 nm | Li 0.5 nm Al 150 nm | 624 | 43 | 14 | 4400 |

TABLE 3

| | | emissive layer | | |
|---|---|---|---|---|
| | Hole transporting layer | Host material | Dopant | Fluorescent peak wavelength in CH2Cl2nm) |
| Example 38 | 4,4'-bis(N-(m-tolyl)-N-phenylamino)biphenyl | 1,4-diketo-2,5-bis(3,5-di-tert-butylbenzyl)-3,6-bis(4-biphenyl)pyrrolo[3,4-c]pyrrole | Compound [99] | 629 |
| Example 39 | 4,4'-bis(N-(m-tolyl)-N-phenylamino)biphenyl | 1,4-diketo-2,5-bis(3,5-di-tert-butylbenzyl)-3,6-bis(4-biphenyl)pyrrolo[3,4-c]pyrrole | Compound [100] | 619 |
| Example 40 | 4,4'-bis(N-(m-tolyl)-N-phenylamino)biphenyl | 1,4-diketo-2,5-bis(3,5-di-tert-butylbenzyl)-3,6-bis(4-biphenyl)pyrrolo[3,4-c]pyrrole | Compound [73] | 630 |
| Example 41 | 4,4'-bis(N-(m-tolyl)-N-phenylamino)biphenyl | 1,4-diketo-2,5-bis(3,5-di-tert-butylbenzyl)-3,6-bis(4-biphenyl)pyrrolo[3,4-c]pyrrole | Compound [69] | 630 |
| Example 42 | 4,4'-bis(N-(m-tolyl)-N-phenylamino)biphenyl | 1,4-diketo-2,5-bis(3,5-di-tert-butylbenzyl)-3,6-bis(3-methylphenyl)pyrrolo[3,4-c]pyrrole | Compound [99] | 629 |
| Example 43 | 4,4'-bis(N-(m-tolyl)-N-phenylamino)biphenyl | 1,4-diketo-2,5-bis(3,5-di-tert-butylbenzyl)-3,6-bis(3-methoxyphenyl)pyrrolo[3,4-c]pyrrole | Compound [99] | 629 |
| Example 44 | 4,4'-bis(N-(m-tolyl)-N-phenylamino)biphenyl | 1,4-diketo-2,5-bis(3,5-di-tert-butylbenzyl)-3,6-bis(4-chlorophenyl)pyrrolo[3,4-c]pyrrole | Compound [99] | 629 |
| Example 45 | 4,4'-bis(N-(m-tolyl)-N-phenylamino)biphenyl | 1,4-diketo-2,5-bis(3,5-di-tert-butylbenzyl)-3,6-bis(4-trans-stilbene)pyrrolo[3,4-c]pyrrole | Compound [99] | 629 |
| Example 46 | | 1,4-diketo-2,5-bis(3,5-di-tert-butylbenzyl)-3,6-bis(4-trans-stilbene)pyrrolo[3,4-c]pyrrole | Compound [73] | 630 |
| Example 47 | 4,4'-bis(N-(m-tolyl)-N-phenylamino)biphenyl | 1,4-diketo-2,5-bis(3,5-di-tert-butylbenzyl)-3,6-bis(4-trans-stilbene)pyrrolo[3,4-c]pyrrole | Compound [69] | 641 |

| | Electron transporting layer | Cathode | Emission peak wavelength (nm) | Spectrum half band width (nm) | applied voltage (V) | Luminance (cd/m$^2$) |
|---|---|---|---|---|---|---|
| Example 38 | Host material 20 nm | BCP 5 nm | Li 0.5 nm Al 150 nm | 638 | 33 | 15 | 5200 |
| Example 39 | Host material 20 nm | BCP 5 nm | Li 0.5 nm Al 150 nm | 628 | 28 | 16 | 7500 |
| Example 40 | Host material 20 nm | BCP 5 nm | Li 0.5 nm Al 150 nm | 628 | 38 | 18 | 2500 |
| Example 41 | Host material 20 nm | BCP 5 nm | Li 0.5 nm Al 150 nm | 645 | 32 | 16 | 1800 |
| Example 42 | Host material 20 nm | BCP 5 nm | Li 0.5 nm Al 150 nm | 631 | 33 | 15 | 2300 |
| Example 43 | Host material 20 nm | BCP 5 nm | Li 0.5 nm Al 150 nm | 640 | 33 | 15 | 3400 |
| Example 44 | Host material 20 nm | BCP 5 nm | Li 0.5 nm Al 150 nm | 640 | 33 | 15 | 4200 |
| Example 45 | Host material 20 nm | BCP 5 nm | Li 0.5 nm Al 150 nm | 637 | 33 | 17 | 1900 |
| Example 46 | Host material 20 nm | BCP 5 nm | Li 0.5 nm Al 150 nm | 630 | 38 | 22 | 1200 |
| Example 47 | Host material 20 nm | BCP 5 nm | Li 0.5 nm Al 150 nm | 648 | 32 | 18 | 1100 |

Example 48

For preparing an LED, 1,4-diketo-2,5-bis(2-phenybenzyl)-3,6-bis(4-methylphenyl)pyrrolo[3,4-c] pyrrole was used as a host material. Other processes were the same as in Example 21. This resulting LED generated a red emission having an emission peak wavelength of 639 nm and a spectrum half band width of 33 nm according to the compound [99]. The red emission exhibited a luminance of 2000 cd/m$^2$ under an applied voltage of 13 V.

Example 49

For preparing an LED, 1,4-diketo-2,5-bis(3,5-dimethylbenzyl)-3,6-bis(4-ethylphenyl)pyrrolo[3,4-c]pyrrole and the compound [1], which had a fluorescent peak wavelength of 613 nm in dichloromethane solution, were used as a host material and a dopant, respectively. Other processes were the same as in Example 28. This resulting LED generated a red emission having an emission peak wavelength of 618 nm and a spectrum half band width of 48 nm according to the compound [1]. The red emission exhibited a luminance of 8000 cd/m$^2$ under an applied voltage of 14 V.

First, CuPc was deposited to a thickness of 10 nm to form a first hole transporting layer, and then N,N'-diphenyl-N-N'-di(naphthalene-1-yl)-1,1'-dipheny-4,4'-diamine(α-NPD) was deposited to a thickness of 50 nm to form a second hole transporting layer. The electron transporting layer was formed of ETM1. Other processes were the same as in Example 49. ETM1 has an ionization potential of 5.99 eV (measured with Atmospheric Ultra-violet Photoelectron Spectrometer produced by Riken Keiki) and a molecular weight of 401. This resulting LED generated a red emission having an emission peak wavelength of 618 nm and a spectrum half band width of 48 nm according to the compound [1]. The red emission exhibited a luminance of 9000 cd/m$^2$ under an applied voltage of 15 V.

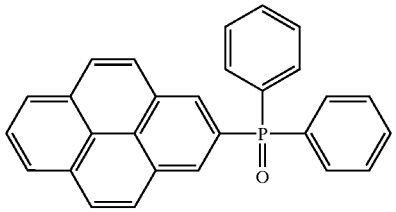

ETM1

Examples 51 to 53

LEDs were prepared in the same procedure as in Example 49 except that the compounds shown in Table 4 were used for the electron transporting layer. The results are shown in table 4. ETM2, ETM3, and ETM4 shown in Table 4 are as follows:

TABLE 4

| | Hole transportation layer | Host material | Dopant | Fluorescent peak wavelength in CH2Cl2 nm | Electron transportation layer | | | | Emission | | | applied voltage (V) | luminance (cd/m²) |
|---|---|---|---|---|---|---|---|---|---|---|---|---|---|
| | | | | | | Ionization potential (eV) | Molecular weight | Tg (° C.) | Cathode | peak wavelength (nm) | Spectrum half band width (nm) | | |
| Example 49 | 4,4'-bis(N-(m-tolyl)-N-phenylamino)biphenyl | 1,4-diketo-2,5-bis(3,6-dimethylbenzyl)-3,6-bis(4-ethylphenyl)pyrrolo[3,4-c]pyrrole | Compound [1] | 613 | BCP | 5.85 | 360 | ≦77 | Li 0.5 nm Al 150 nm | 618 | 48 | 14 | 8000 |
| Example 51 | 4,4'-bis(N-(m-tolyl)-N-phenylamino)biphenyl | 1,4-diketo-2,5-bis(3,6-dimethylbenzyl)-3,6-bis(4-ethylphenyl)pyrrolo[3,4-c]pyrrole | Compound [1] | 613 | ETM2 | 5.97 | 609 | 112 | Li 0.5 nm Al 150 nm | 618 | 48 | 15 | 8000 |
| Example 52 | 4,4'-bis(N-(m-tolyl)-N-phenylamino)biphenyl | 1,4-diketo-2,5-bis(3,6-dimethylbenzyl)-3,6-bis(4-ethylphenyl)pyrrolo[3,4-c]pyrrole | Compound [1] | 613 | ETM3 | 6.07 | 670 | 165 | Li 0.5 nm Al 150 nm | 618 | 48 | 15 | 10000 |
| Example 53 | 4,4'-bis(N-(m-tolyl)-N-phenylamino)biphenyl | 1,4-diketo-2,5-bis(3,6-dimethylbenzyl)-3,6-bis(4-ethylphenyl)pyrrolo[3,4-c]pyrrole | Compound [1] | 613 | ETM4 | 6.07 | 672 | 219 | Li 0.5 nm Al 150 nm | 618 | 48 | 14 | 11000 |
| Example 54 | 4,4'-bis(N-(m-tolyl)-N-phenylamino)biphenyl | 1,4-diketo-2,5-bis(3,6-diethyl-3,6-bis(1-naphthyl)pyrrolo[3,4-c]pyrrole | Compound [53] | 611 | ETM4 | 6.07 | 672 | 219 | Li 0.5 nm Al 150 nm | 615 | 43 | 14 | 12000 |
| Example 55 | 4,4'-bis(N-(m-tolyl)-N-phenylamino)biphenyl | 1,4-diketo-2,5-bis(3,6-dimethyl-3,6-bis(1-naphthyl)pyrrolo[3,4-c]pyrrole | Compound [53] | 613 | ETM4 | 6.07 | 672 | 219 | Li 0.5 nm Al 150 nm | 615 | 43 | 15 | 16000 |
| Example 56 | 4,4'-bis(N-(m-tolyl)-N-phenylamino)biphenyl | 1,4-diketo-2,5-bis(4-methylbenzyl)-3,6-bis(4-p-tolylnaphthalene-1-yl)pyrrolo[3,4-c]pyrrole | Compound [53] | 613 | ETM4 | 6.07 | 672 | 219 | Li 0.5 nm Al 150 nm | 616 | 43 | 13 | 9000 |
| Example 57 | 4,4'-bis(N-(m-tolyl)-N-phenylamino)biphenyl | 1,4-diketo-2,5-dimethyl-3,6-bis(4-p-tolylnapthalene-1-yl)pyrrolo[3,4-c]pyrrole | Compound [53] | 613 | ETM2 | 6.07 | 672 | 219 | Li 0.5 nm Al 150 nm | 616 | 43 | 15 | 15000 |

Example 54
Synthesis of 1,4-diketo-2,5-diethyl-3,6-bis(1-naphthyl)pyrrolo[3,4-c]pyrrole In 36 mL of t-amyl alcohol, 7.3 g of potassium-t-butoxide were solved, and then 10 g of 1-naphthonitrile were added stirring the solution at 90° C. Into the solution, 6.7 mL of diisopropyl succinate were dropped taking time for 2 hours and were placed under reflux for one day. Next, 30 mL of methanol and 4.4 mL of acetic acid were added at 60° C. and then refluxed for 30 minutes. After cooling, the product was separated out through a filter and subsequently rinsed with methanol, thus resulting in a red powder. Next, 2.89 g of the resulting red powder were dissolved in 80 mL of DMF, and 2.1 g of potassium-t-butoxide were added and stirred for one hour. Then, 1.5 mL of methyl iodide was added and stirred at 65° C. for one day. After 50 mL of water was added, extraction was performed with dichloromethane. The extract was concentrated and refined through a column chromatography with silica gel and thus results in 1.5 g of yellow powder. The following is the results of $^1$H-NMR analysis.

$^1$H-NMR (CDCl$_3$ (δ=ppm)): 0.93(tt, 6H), 3.35(qq, 2H), 3.70(qq, 2H), 7.58–7.68(m, 6H), 7.76(t, 2H), 7.90(m, 4H), 8.02(d, 2H).

Elemental analysis was performed on the assumption that the composition formula of the powder was $C_{30}H_{24}N_2O_2$. The results are as follows. Values in parentheses are theoretical values.

C: 81.2% (81.1%), H: 5.3% (5.4%), N: 6.3% (6.3%), O: 7.2% (7.2%).

According to mass spectrometry, the main molecular ion peak of the object powder was m/Z=444. Thus, the resulting yellow powder was identified as 1,4-diketo-2,5-diethyl-3,6-bis(1-naphthyl)pyrrolo[3,4-c]pyrrole.

Subsequently, an LED was prepared using this 1,4-diketo-2,5-diethyl-3,6-bis(1-naphthyl)pyrrolo[3,4-c]pyrrole as a host material and the compound [53] as a dopant. Other processes were the same as in Example 53. This resulting LED generated a red emission having an emission peak wavelength of 615 nm and a spectrum half band width of 43 nm according to the compound [53]. The red emission exhibited a luminance of 12000 cd/m$^2$ under an applied voltage of 14 V.

Example 55

Using 1,4-diketo-2,5-dimethyl-3,6-bis(1-naphthyl)pyrrolo[3,4-c]pyrrole as a host material, an LED was prepared. Other processes were the same as in Example 54. This resulting LED generated a red emission having an emission peak wavelength of 615 nm and a spectrum half band width of 43 nm according to the compound [53]. The red emission exhibited a luminance of 16000 cd/m$^2$ under an applied voltage of 15 V.

Example 56
Synthesis of 1,4-diketo-2,5-bis(4-methylbenzyl)-3,6-bis(4-p-tolylnaphthalene-1-yl)pyrrolo[3,4-c]pyrrole Instead of 1-naphthonitrile and methyl iodide, 4-p-tolyl-1-naphthonitrile and 4-methylbenzyl bromide were used, respectively. Other processes were the same as in Example 54. Thus, 1.2 g of orange powder were obtained. The following is the results of $^1$H-NMR analysis.

$^1$H-NMR (CDCl$_3$(δ=ppm)): 2.20(s, 6H), 2.49(s, 6H), 4.38 (t, 2H), 4.93(t, 2H), 6.69(t, 4H), 6.88(t, 4H), 7.35(d, 4H), 7.42–7.64(m, 12H), 8.00(t, 4H).

Elemental analysis was performed on the assumption that the composition formula of the powder was $C_{56}H_{44}N_2O_2$. The results are as follows. Values in parentheses are theoretical values.

C: 86.6% (86.6%), H: 5.7% (5.7%), N: 3.5% (3.6%), O: 4.1% (4.1%).

According to mass spectrometry, the main molecular ion peak of the object was m/Z=776. Thus, the resulting orange powder was identified as 1,4-diketo-2,5-bis(4-methylbenzyl)-3,6-bis(4-p-tolylnaphthalene-1-yl)pyrrolo[3,4-c]pyrrole.

Subsequently, an LED was prepared using this 1,4-diketo-2,5-bis(4-methylbenzyl)-3,6-bis(4-p-tolylnaphthalene-1-yl)pyrrolo[3,4-c]pyrrole as a host material. Other processes were the same as in Example 54. This resulting LED generated a red emission having an emission peak wavelength of 616 nm and a spectrum half band width of 43 nm according to the compound [53]. The red emission exhibited a luminance of 9000 cd/m$^2$ under an applied voltage of 13 V.

Example 57
synthesis of 1,4-diketo-2,5-dimethyl-3,6-bis(4-p-tolylnaphthalene-1-yl)pyrrolo[3,4-c]pyrrole Instead of 1-naphthonitrile and methyl iodide, 4-p-tolyl-1-naphthonitrile and methyl iodide were used, respectively. Other processes were the same as in Example 54. Thus, 1.4 g of orange powder were obtained. The following is the results of $^1$H-NMR analysis.

$^1$H-NMR (CDCl$_3$ (δ=ppm)): 2.49(s, 6H), 3.05(s, 6H), 7.35(d, 4H), 7.44–7.65(m, 10H), 7.98(d, 2H), 8.02(dd, 4H).

Elemental analysis was performed on the assumption that the composition formula of the powder was $C_{42}H_{32}N_2O_2$. The results are as follows. Values in parentheses are theoretical values.

C: 84.6% (84.6%), H: 5.4% (5.4%), N: 4.7% (4.7%), O: 5.3% (5.4%).

According to mass spectrometry, the main molecular ion peak of the object was m/Z=596. Thus, the resulting orange powder was identified as 1,4-diketo-2,5-dimethyl-3,6-bis(4-p-tolylnaphthalene-1-yl)pyrrolo[3,4-c]pyrrole.

Subsequently, an LED was prepared using this 1,4-diketo-2,5-dimethyl-3,6-bis(4-p-tolylnaphthalene-1-yl)pyrrolo[3,4-c]pyrrole as a host material. Other processes were the same as in Example 54. This resulting LED generated a red emission having an emission peak wavelength of 616 nm and a spectrum half band width of 43 nm according to the compound [53]. The red emission exhibited a luminance of 15000 cd/m$^2$ under an applied voltage of 15 V.

Example 58

Using 1,4-diketo-2,5-dimethyl-3-(1-naphthyl)-6-(3,5-bis(1-naphthyl)phenyl)pyrrolo[3,4-c]pyrrole as a host material and the compound [1] as a dopant, an LED was prepared. Other processes were the same as in Example 54. This resulting LED generated a red emission having an emission peak wavelength of 616 nm and a spectrum half band width of 48 nm according to the compound [1]. The red emission exhibited a luminance of 9000 cd/m$^2$ under an applied voltage of 13 V.

Example 59
Synthesis of 1,4-diketo-2,5-bis(4-methylbenzyl)-3,6-bis(1-phenanthryl)pyrrolo[3,4-c]pyrrole Instead of 1-naphthonitrile and methyl iodide, 1-phenanthrenecarbonitrile and 4-methylbenzyl bromide were used, respectively. Other processes were the same as in Example 54. Thus, 0.9 g of orange powder were obtained. The following is the results of $^1$H-NMR analysis.

$^1$H-NMR (CDCl$_3$ (δ=ppm)): 2.18(ss, 6H), 4.40(t, 2H), 4.90(t, 2H), 6.64(t, 4H), 6.79(t, 4H), 7.62–7.86(m, 12H), 7.96(t, 2H), 8.79(t, 4H).

Elemental analysis was performed on the assumption that the composition formula of the powder was $C_{50}H_{36}N_2O_2$. The results are as follows. Values in parentheses are theoretical values.

C: 86.3% (86.2%), H: 5.2% (5.2%), N: 3.9% (4.0%), O: 4.5% (4.6%).

According to mass spectrometry, the main molecular ion peak of the object was m/Z=696. Thus, the resulting orange powder was identified as 1,4-diketo-2,5-bis(4-methylbenzyl)-3,6-bis(1-phenanthryl)pyrrolo[3,4-c]pyrrole.

Subsequently, an LED was prepared using this 1,4-diketo-2,5-bis(4-methylbenzyl)-3,6-bis(1-phenanthryl)pyrrolo[3,4-c]pyrrole as a host material. Other processes were the same as in Example 54. This resulting LED generated a red emission having an emission peak wavelength of 616 nm and a spectrum half band width of 43 nm according to the compound [53]. The red emission exhibited a luminance of 13000 cd/m² under an applied voltage of 15 V.

Example 60

Using 1,4-diketo-2,5-dimethyl-3,6-bis(1-phenanthryl)pyrrolo[3,4-c]pyrrole as a host material, an LED was prepared. Other processes were the same as in Example 54. This resulting LED generated a red emission having an emission peak wavelength of 616 nm and a spectrum half band width of 43 nm according to the compound [53]. The red emission exhibited a luminance of 17000 cd/m² under an applied voltage of 14 V.

the dopant used. This resulting LED generated a red emission having an emission peak wavelength of 627 nm and a luminance efficiency of 1.0 cd/A.

Example 62

An ITO transparent conductive layer deposited on a glass substrate, having a thickness of 150 nm (produced by electron beam evaporation by Asahi Glass, 15 Ω/□), was cut into 30 mm×40 mm and then was patterned with 32 stripes having a pitch of 300 μm (a width of the remaining ITO of 270 μm) by photolithography. The ITO stripes diverge up to a pitch of 1.27 mm (an opening width of 800 μm) in a longitudinal direction of the stripes in order to facilitate the electrical connection with external. The ITO plate was subjected to ultrasonic cleanings successively using acetone and cleaner Semicoclean 56 (produced by Furuuchi Chemical) for 15 minutes each, and then rinsed with ultra-pure water. Subsequently, the ITO plate was subjected to ultrasonic cleaning in isopropyl alcohol for 15 minutes, then immersed in hot methanol for 15 minutes, and was followed by drying. The ITO plate was subjected to a UV-ozone treatment for one hour on the eve of the process of manufacturing an LED. Then, the ITO plate was placed in a vacuum vapor deposition apparatus and the apparatus was evacuated to a pressure of $5\times10^{-4}$ Pa or below. On the ITO plate, 100 nm in thickness of TPD was deposited. Next, 1,4-diketo-2,5-bis(3,5-dimethylbenzyl)-3,6-bis(4-ethylphenyl)pyrrolo[3,4-c]pyrrole as a host material and

TABLE 5

| | Hole transporting layer | emissive layer | | |
|---|---|---|---|---|
| | | Host material | Dopant | Fluorescent peak wavelength in CH2Cl2nm) |
| Example 58 | 4,4'-bis(N-(m-tolyl)-N-phenylamino)biphenyl | 1,4-diketo-2,5-dimethyl-3-(1-naphthyl)-6-(3,5-bis(1-naphthyl)phenyl)pyrrolo[3,4-c]pyrrole | Compound [1] | 613 |
| Example 59 | 4,4'-bis(N-(m-tolyl)-N-phenylamino)biphenyl | 1,4-diketo-2,5-bis(4-methylbenzyl)-3,6-bis(1-phenanthryl)pyrrolo[3,4-c]pyrrole | Compound [53] | 613 |
| Example 60 | 4,4'-bis(N-(m-tolyl)-N-phenylamino)biphenyl | 1,4-diketo-2,5-dimethyl-3,6-bis(1-phenanthryl) pyrrolo[3,4-c]pyrrole | Compound [53] | 613 |

| | Electron transporting layer | | | | Emission | | | |
|---|---|---|---|---|---|---|---|---|
| | Ionization potential (eV) | Molecular weight | Tg (° C.) | Cathode | peak wavelength (nm) | Spectrum half band width (nm) | applied voltage (V) | Luminance (cd/m²) |
| ETM4 | 6.07 | 672 | 219 | Li 0.5 nm Al 150 nm | 616 | 48 | 13 | 9000 |
| ETM4 | 6.07 | 672 | 219 | Li 0.5 nm Al 150 nm | 616 | 43 | 15 | 13000 |
| ETM4 | 6.07 | 672 | 219 | Li 0.5 nm Al 150 nm | 616 | 43 | 14 | 17000 |

Example 61

Using tris(5,7-diphenyl-8-quinolinolato)aluminum (III) as a host material, an LED was prepared in the same procedure as in Example 1 other than the host material used. This resulting LED generated a red emission having an emission peak wavelength of 613 nm and a luminance efficiency of 3.2 cd/A.

Comparative Example 2

Using the compound [86] as the dopant, an LED was prepared in the same procedure as in Example 61 other than Compound [1] as a dopant were simultaneously deposited so as to form a layer having a thickness of 50 nm and a dopant content of 0.6 weight percent, and ETM2 was further deposited so as to have a thickness of 50 nm. Next, a mask which had been provided with 16 openings having a width of 250 μm (a remaining portion width of 50 μm and a pitch of 300 μm) on a Kovar plate by wet etching was fitting to the substrate, in vacuum, so that the openings of the mask orthogonally crossed the ITO stripes. The mask and the ITO plate adhesively came into contact with each other by magnet at the backside. Then, 50 nm in thickness of magnesium and 150 nm in thickness of aluminum are disposed and thus a 32×16 dot matrix device was completed. By driving this device by a matrix system, characters could be displayed without cross talk.

What is claimed is:

1. A pyrromethene metal complex represented by formula (1):

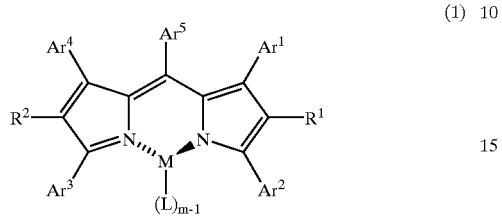

Wherein $R^1$, $R^2$, and L are each a substituent selected from the group consisting of hydrogen, alkyl, cycloalkyl, aralkyl, alkenyl, cycloalkenyl, alkynyl, hydroxyl, mercapto, alkoxy, alkylthio, aryl ether, aryl thioether, aryl, heterocyclic, halogen, haloalkane, haloalkene, haloalkyne, cyano, aldehyde, carbonyl, carboxyl, ester, carbamoyl, amino, nitro, silyl, siloxanyl, and a fused aromatic ring and an alicyclic ring formed with adjacent substituents, and $R^1$, $R^2$, and L may be the same or different; M is a metal having a valence of m and is selected from the group consisting of boron, beryllium, magnesium, chromium, iron, nickel, copper, zinc, and platinum; and $Ar^1$ to $Ar^5$ are aryl.

2. A pyrromethene metal complex according to claim 1, wherein at least one of $Ar^1$ to $Ar^4$ is an aryl group having an alkyl group with a carbon number of 4 or more.

3. A light emitting device composition comprising a pyrromethene metal complex as set forth in claim 1.

4. A pyrromethene metal complex represented by formula (2):

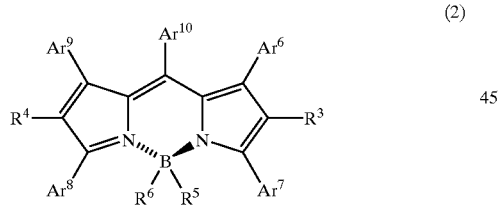

Wherein $R^3$ to $R^6$ are each a substituent selected from the group consisting of hydrogen, alkyl, cycloalkyl, aralkyl, alkenyl, cycloalkenyl, alkynyl, hydroxyl, mercapto, alkoxy, alkylthio, aryl ether, aryl thioether, aryl, heterocyclic, halogen, haloalkane, haloalkene, haloalkyne, cyano, aldehyde, carbonyl, carboxyl, ester, carbamoyl, amino, nitro, silyl, siloxanyl, and a fused aromatic ring and an alicyclic ring formed with adjacent substituents, and $R^3$ to $R^6$ may be the same or different; and $Ar^6$ to $Ar^{10}$ are aryl.

5. A pyrromethene metal complex according to claim 4, wherein both $R^5$ and $R^6$ are fluorine.

6. A light emitting device wherein a substance which bring about light emission is present between an anode and a cathode, the light emitting device generates a emission having an emission peak wavelength in the range of 580 to 720 nm by electrical energy, and the substance which bring about light emission contains a pyrromethene metal complex represented by formula (1), wherein formula (1) is:

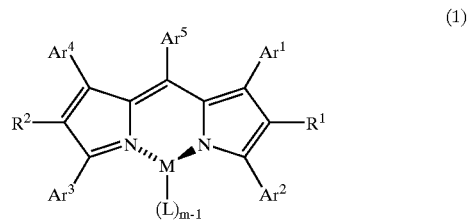

wherein $R^1$, $R^2$, and L are each a substituent selected from the group consisting of hydrogen, alkyl, cycloalkyl, aralkyl, alkenyl, cycloalkenyl, alkynyl, hydroxyl, mercapto, alkoxy, alkylthio, aryl ether, aryl thioether, aryl, heterocyclic, halogen, haloalkane, haloalkene, haloalkyne, cyano, aldehyde, carbonyl, carboxyl, ester, carbamoyl, amino, nitro, silyl, siloxanyl, and a fused aromatic ring and an alicyclic ring formed with adjacent substituents, and $R^1$, $R^2$, and L may be the same or different; M is a metal having a valence of m and is selected from the group consisting of boron, beryllium, magnesium, chromium, iron, nickel, copper, zinc, and platinum; and $Ar^1$ to $Ar^5$ are aryl.

7. A light emitting device according to claim 6, wherein the substance which bring about emission further comprises a diketopyrrolo[3,4-c]pyrrole derivative represented by formula (3):

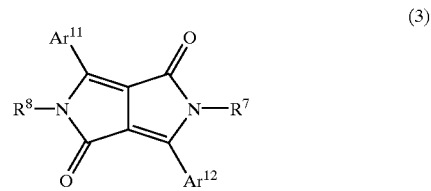

wherein $R^7$ and $R^8$ may be the same or different and are each a substituent selected from the group consisting of alkyl having carbon numbers of 1 to 25 and substituents represented by formula (4):

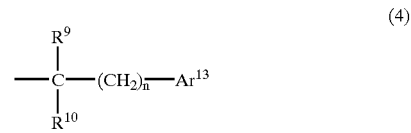

wherein $R^9$ and $R^{10}$ are each a substituent selected from the group consisting of hydrogen, alkyl having carbon numbers of 1 to 4, phenyl having no substituent or having alkyl having carbon numbers of 1 to 3 therein, and $R^9$ and $R^{10}$ may be the same or different; $Ar^{13}$ is a substituent selected from the group consisting of phenyl and naphthyl having alkyl or alkoxy or halogen or phenyl and naphthyl; n is a whole number 0 to 4; and $Ar^{11}$ and $Ar^{12}$ are each a substituent selected from the group consisting of phenyl having a substituent, naphthyl, styryl and carbazolyl and $Ar^{11}$ and $Ar^{12}$ may be the same or different, and when both $Ar^{11}$ and $Ar^{12}$ are 1-naphtyl having no substituent $R^7$ and $R^8$ are the same or different and are each an alkyl substituent having a carbon number 1 to 25.

8. A light emitting device according to claim 7, wherein the substance which bring about emission further comprises emissive materials and a hole transporting material and an electron transporting material, and wherein the emissive materials comprising the diketopyrrole[3,4-c]pyrrole derivative is represented by formula (3) and the pyrromethene metal complex represented by formula (1).

9. A light emitting device according to claim 8, wherein the diketopyrrole[3,4-c]pyrrole derivative represented by formula 3 is a host material and the pyrromethane complex represented by formula (1) is a dopant.

* * * * *